US011584712B2

(12) United States Patent
Toscano et al.

(10) Patent No.: US 11,584,712 B2
(45) Date of Patent: Feb. 21, 2023

(54) ALKYLAMINE-SUBSTITUTED PERTHIOCARBAMATES AS DUAL PRECURSORS TO HYDROPERSULFIDE AND CARBONYL SULFIDE

(71) Applicant: The Johns Hopkins University, Baltimore, MD (US)

(72) Inventors: John Pasquale Toscano, Baltimore, MD (US); Vinayak S. Khodade, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 171 days.

(21) Appl. No.: 17/166,434

(22) Filed: Feb. 3, 2021

(65) Prior Publication Data

US 2021/0238134 A1   Aug. 5, 2021

Related U.S. Application Data

(60) Provisional application No. 62/969,348, filed on Feb. 3, 2020.

(51) Int. Cl.
*C07C 333/04* (2006.01)
*C07C 321/14* (2006.01)
*A61P 9/10* (2006.01)

(52) U.S. Cl.
CPC .............. *C07C 333/04* (2013.01); *A61P 9/10* (2018.01); *C07C 321/14* (2013.01)

(58) Field of Classification Search
None
See application file for complete search history.

(56) References Cited

U.S. PATENT DOCUMENTS 4,798,824 A    1/1989 Belzer et al.

OTHER PUBLICATIONS

Akaike et al., Cysteinyl-tRNA synthetase governs cysteine polysulfidation and mitochondrial bioenergetics. Nat Commun. Oct. 27, 2017;8(1):1177.
Aldini et al., N-Acetylcysteine as an antioxidant and disulphide breaking agent: the reasons why. Free Radic Res. Jul. 2018;52(7):751-762.
Álvarez et al., Chemical Biology of Hydropersulfides and Related Species: Possible Roles in Cellular Protection and Redox Signaling. Antioxid Redox Signal. Oct. 1, 2017;27(10):622-633.
Artaud et al., A persulfide analogue of the nitrosothiol SNAP: formation, characterization and reactivity. Chembiochem. Nov. 3, 2014;15(16):2361-4.
Bajic et al., Glutathione "Redox Homeostasis" and Its Relation to Cardiovascular Disease. Oxid Med Cell Longev. May 9, 2019;2019:5028181. 14 pages.
Bell et al., Retrograde heart perfusion: the Langendorff technique of isolated heart perfusion. J Mol Cell Cardiol. Jun. 2011;50(6):940-50.
Berge et al, Pharmaceutical salts. J Pharm Sci. Jan. 1977;66(1):1-19.
Bianco et al., The chemical biology of the persulfide (RSSH)/perthiyl (RSS•) redox couple and possible role in biological redox signaling. Free Radic Biol Med. Dec. 2016;101:20-31.
Bianco et al., The reaction of hydrogen sulfide with disulfides: formation of a stable trisulfide and implications for biological systems. Br J Pharmacol. Feb. 2019;176(4):671-683.
Blencowe et al., Self-immolative linkers in polymeric delivery systems. Polym. Chem. 2011, 2, 773-790.
Bogdándi et al., Speciation of reactive sulfur species and their reactions with alkylating agents: do we have any clue about what is present inside the cell? Br J Pharmacol. Feb. 2019;176(4):646-670.
Bora et al., A Vinyl-Boronate Ester-Based Persulfide Donor Controllable by Hydrogen Peroxide, a Reactive Oxygen Species (ROS). Org Lett. Dec. 21, 2018;20(24):7916-7920.
Branzoli et al., Evidence for an active site persulfide residue in rabbit liver aldehyde oxidase. J Biol Chem. Jul. 25, 1974;249(14):4346-9.
Chauhan et al., Carbonyl Sulfide (COS) Donor Induced Protein Persulfidation Protects against Oxidative Stress. Chem Asian J. Dec. 13, 2019;14(24):4717-4724.
Chauvin et al., Hydropersulfides: H-Atom Transfer Agents Par Excellence. J Am Chem Soc. May 10, 2017;139(18):6484-6493.
Chengelis et al., Studies of carbonyl sulfide toxicity: Metabolism by carbonic anhydrase. Toxicol Appl Pharmacol. Aug. 1980;55(1):198-202.
Cline et al., Detection of nitroxyl (HNO) by membrane inlet mass spectrometry. Free Radic Biol Med. May 15, 2011;50(10):1274-9.
Cuevasanta et al., Kinetics of formation and reactivity of the persulfide in the one-cysteine peroxiredoxin from *Mycobacterium tuberculosis*. J Biol Chem. Sep. 13, 2019;294(37):13593-13605.
Cuevasanta et al., Reaction of Hydrogen Sulfide with Disulfide and Sulfenic Acid to Form the Strongly Nucleophilic Persulfide. J Biol Chem. Nov. 6, 2015;290(45):26866-26880.
Devine et al., From Cells to Mice to Target: Characterization of NEU-1053 (SB-443342) and Its Analogues for Treatment of Human African Trypanosomiasis. ACS Infect Dis. Mar. 10, 2017;3(3):225-236.
Dóka et al., A novel persulfide detection method reveals protein persulfide- and polysulfide-reducing functions of thioredoxin and glutathione systems. Sci Adv. Jan. 22, 2016;2(1):e1500968.
Effros et al., In vivo myocardial cell pH in the dog. Response to ischemia and infusion of alkali. J Clin Invest. May 1975;55(5):1100-10.
Filipovic et al., Chemical Biology of H 2 S Signaling through Persulfidation. Chem Rev. Feb. 14, 2018;118(3):1253-1337.
Filipovic et al., Reaction of Hydrogen Sulfide with Disulfide and Sulfenic Acid to Form the Strongly Nucleophilic Persulfide. J Biol Chem. Nov. 6, 2015;290(45):26866-26880.
Fukuto et al., Biological hydropersulfides and related polysulfides—a new concept and perspective in redox biology. FEBS Lett. Jun. 2018;592(12):2140-2152.
Gadalla et al., Hydrogen sulfide as a gasotransmitter. J Neurochem. Apr. 2010;113(1):14-26.

(Continued)

*Primary Examiner* — Golam M Shameem
(74) *Attorney, Agent, or Firm* — Casimir Jones, S.C.; Jeffrey W. Childers

(57) ABSTRACT

Alkylamine-substituted perthiocarbamates capable of controllable release of hydropersulfides (RSSH) and carbonyl sulfide (COS) and their use in treating or preventing ischemia-reperfusion injury are described.

9 Claims, 26 Drawing Sheets

(56) References Cited

OTHER PUBLICATIONS

Gomes et al., Cyclization-activated prodrugs. Molecules. Nov. 12, 2007;12(11):2484-506.
Greene et al., Protective Groups in Organic Synthesis, 3rd ed. John Wiley & Sons. 1999. TOC only. 3 pages.
Hamid et al., Polysulfide stabilization by tyrosine and hydroxypheny-containing derivatives that is important for a reactive sulfur metabolomics analysis. Redox Biol. Feb. 2019;21:101096. 7 pages.
Hofgaard et al., Protection by 6-aminonicotinamide against oxidative stress in cardiac cells. Pharmacol Res. Oct. 2006;54(4):303-10.
Ida et al., Reactive cysteine persulfides and S-polythiolation regulate oxidative stress and redox signaling. Proc Natl Acad Sci U S A. May 27, 2014;111(21):7606-11.
Ishiyama et al., A highly water-soluble disulfonated tetrazolium salt as a chromogenic indicator for NADH as well as cell viability. Talanta. Jul. 1997;44(7):1299-305.
Jones et al., Fluorescence microplate-based assay for tumor necrosis factor activity using SYTOX Green stain. Anal Biochem. Jun. 1, 2001;293(1):8-15.
Ju et al., $H_2$S-Mediated Protein S-Sulfhydration: A Prediction for Its Formation and Regulation. Molecules. Aug. 11, 2017;22(8):1334.
Kang et al., O→S Relay Deprotection: A General Approach to Controllable Donors of Reactive Sulfur Species. Angew Chem Int Ed Engl. May 14, 2018;57(20):5893-5897.
Khodade et al., Development of S-Substituted Thioisothioureas as Efficient Hydropersulfide Precursors. J Am Chem Soc. Dec. 19, 2018;140(50):17333-17337.
Kull et al., Mixturs of quaternary ammonium compounds and long-chain fatty acids as antifungal agents. Appl Microbiol. Nov. 1961;9(6):538-41.
Kunikata et al., Metabolomic profiling of reactive persulfides and polysulfides in the aqueous and vitreous humors. Sci Rep. Feb. 7, 2017;7:41984. 10 pages.
Li et al., A convenient synthesis of amino acid methyl esters. Molecules. May 8, 2008;13(5):1111-9.
Lin et al., The Uptake and Release of Polysulfur Cysteine Species by Cells: Physiological and Toxicological Implications. Chem Res Toxicol. Mar. 18, 2019;32(3):447-455.
Longen et al., Quantitative Persulfide Site Identification (qPerS-SID) Reveals Protein Targets of H2S Releasing Donors in Mammalian Cells. Sci Rep. Jul. 14, 2016;6:29808. 12 pages.
Massey et al., On the mechanism of inactivation of xanthine oxidase by cyanide. J Biol Chem. Dec. 25, 1970;245(24):6595-8.
Meyer et al., A comparative study of the self-immolation of para-aminobenzylalcohol and hemithioaminal-based linkers in the context of protease-sensitive fluorogenic probes. Org Biomol Chem. Apr. 21, 2010;8(8):1777-80.
Millikin et al., The chemical biology of protein hydropersulfides: Studies of a possible protective function of biological hydropersulfide generation. Free Radic Biol Med. Aug. 2016;97:136-147.
Mustafa et al., H2S signals through protein S-sulfhydration. Sci Signal. Nov. 10, 2009;2(96):ra72. 15 pages.
Numakura et al., Production of reactive persulfide species in chronic obstructive pulmonary disease. Thorax. Dec. 2017;72(12):1074-1083.
Ono et al., Redox chemistry and chemical biology of H2S, hydropersulfides, and derived species: implications of their possible biological activity and utility. Free Radic Biol Med. Dec. 2014;77:82-94.
Pagliaro et al., Nitroxyl affords thiol-sensitive myocardial protective effects akin to early preconditioning. Free Radic Biol Med. Jan. 1, 2003;34(1):33-43.
Powell et al., A Persulfide Donor Responsive to Reactive Oxygen Species: Insights into Reactivity and Therapeutic Potential. Angew Chem Int Ed Engl. May 22, 2018;57(21):6324-6328.
Powell et al., Self-Amplified Depolymerization of Oligo(thiourethanes) for the Release of COS/H 2 S. Polym Chem. Jun. 21, 2019;10(23):2991-2995.
Powell et al., Therapeutic Delivery of H 2 S via COS: Small Molecule and Polymeric Donors with Benign Byproducts. J Am Chem Soc. Oct. 19, 2016;138(41):13477-13480.
Rossello et al., Characterization of the Langendorff Perfused Isolated Mouse Heart Model of Global Ischemia-Reperfusion Injury: Impact of Ischemia and Reperfusion Length on Infarct Size and LDH Release. J Cardiovasc Pharmacol Ther. May 2016;21(3):286-95.
Saari et al., Cyclization-activated prodrugs. Basic carbamates of 4-hydroxyanisole. J Med Chem. Jan. 1990;33(1):97-101.
Saund et al., The chemical biology of hydropersulfides (RSSH): Chemical stability, reactivity and redox roles. Arch Biochem Biophys. Dec. 15, 2015;588:15-24.
Sharma et al., Visible-Light-Triggered Uncaging of Carbonyl Sulfide for Hydrogen Sulfide (H 2 S) Release. Org Lett. Sep. 15, 2017;19(18):4822-4825.
Shibata et al., Human serum albumin hydropersulfide is a potent reactive oxygen species scavenger in oxidative stress conditions such as chronic kidney disease. Biochem Biophys Res Commun. Oct. 21, 2016;479(3):578-583.
Shinkai et al., Sulfane Sulfur in Toxicology: A Novel Defense System Against Electrophilic Stress. Toxicol Sci. Jul. 1, 2019;170(1):3-9.
Steiger et al., Emerging Roles of Carbonyl Sulfide in Chemical Biology: Sulfide Transporter or Gasotransmitter? Antioxid Redox Signal. Jun. 1, 2018;28(16):1516-1532.
Steiger et al., Self-lmmolative Thiocarbamates Provide Access to Triggered H2S Donors and Analyte Replacement Fluorescent Probes. J Am Chem Soc. Jun. 15, 2016;138(23):7256-9.
Sun et al., Additive cardioprotection by pharmacological postconditioning with hydrogen sulfide and nitric oxide donors in mouse heart: S-sulfhydration vs. S-nitrosylation. Cardiovasc Res. May 1, 2016;110(1):96-106.
Tominaga et al., A water-soluble tetrazolium salt useful for colorimetric cell viability assay. Anal. Commun. 1999, 36, 47-50.
Toohey. Persulfide sulfur is a growth factor for cells defective in sulfur metabolism. Biochem Cell Biol. Aug. 1986;64(8):758-65.
Wang et al., Plasma and dietary antioxidant status as cardiovascular disease risk factors: a review of human studies. Nutrients. Jul. 31, 2013;5(8):2969-3004.
Wright et al., Direct evidence for enzyme persulfide and disulfide intermediates during 4-thiouridine biosynthesis. Chem Commun (Camb). Aug. 7, 2006;(29):3104-6.
Yan et al., Changes in extracellular and intracellular pH in ischemic rabbit papillary muscle. Circ Res. Aug. 1992;71(2):460-70.
Yang et al., S-Persulfidation: Chemistry, Chemical Biology, and Significance in Health and Disease. Antioxid Redox Signal. Nov. 20, 2020;33(15):1092-1114.
Zhao et al., Cyclic Sulfenyl Thiocarbamates Release Carbonyl Sulfide and Hydrogen Sulfide Independently in Thiol-Promoted Pathways. J Am Chem Soc. Aug. 28, 2019;141(34):13610-13618.
Zhao et al., Fluorogenic hydrogen sulfide (H 2 S) donors based on sulfenyl thiocarbonates enable H 2 S tracking and quantification. Chem Sci. Dec. 10, 2018;10(6):1873-1878.
Zhao et al., Hydrogen Sulfide Donors Activated by Reactive Oxygen Species. Angew Chem Int Ed Engl. Nov. 14, 2016;55(47):14638-14642.
Zheng et al., An Esterase-Sensitive Prodrug Approach for Controllable Delivery of Persulfide Species. Angew Chem Int Ed Engl. Sep. 18, 2017;56(39):11749-11753.

pH-sensitive RSSH precursors
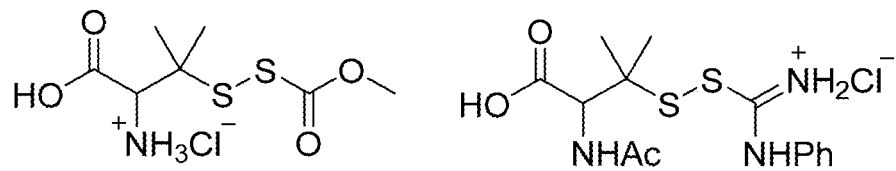
Esterase and fluoride-sensitive RSSH precursors
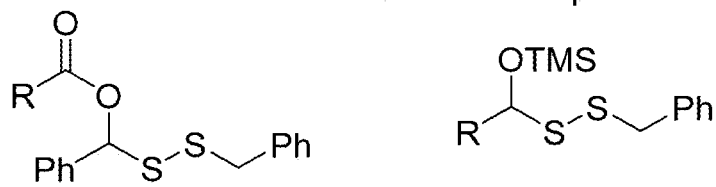
H₂O₂-triggered RSSH precursors
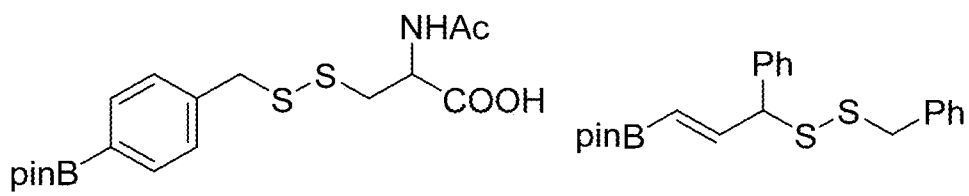
Thiol-triggered COS/H₂S donors
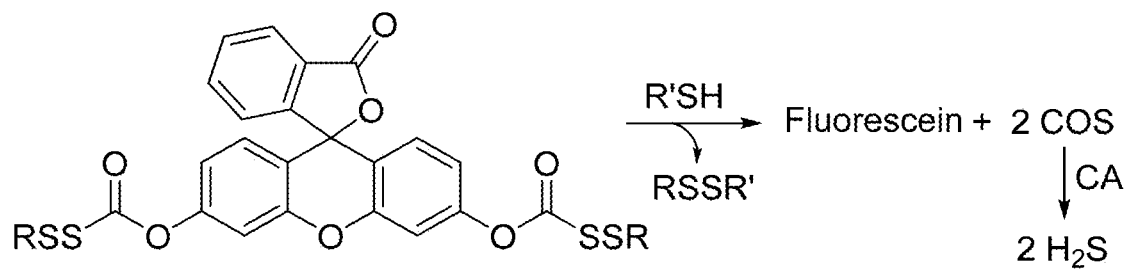
*Fig. 1 (prior art)*

| | R² | n | yield (%) |
|---|---|---|---|
| 7a | CH₃ | 1 | 96 |
| 7b | H | 1 | 97 |
| 7c | CH₃ | 2 | 94 |
| 7d | H | 2 | 96 |

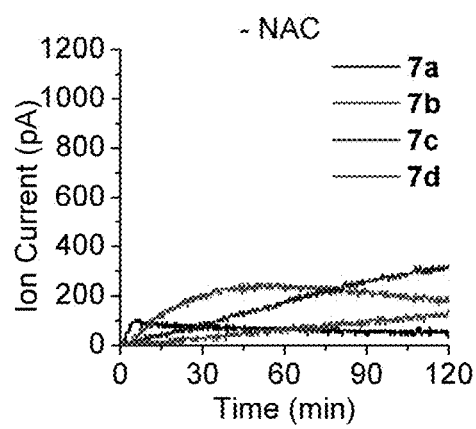
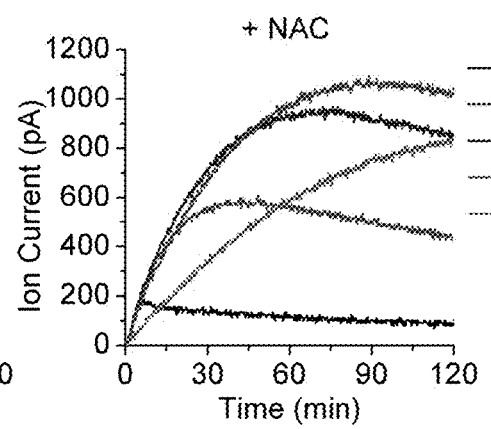
*Fig. 5a*  *Fig. 5b*

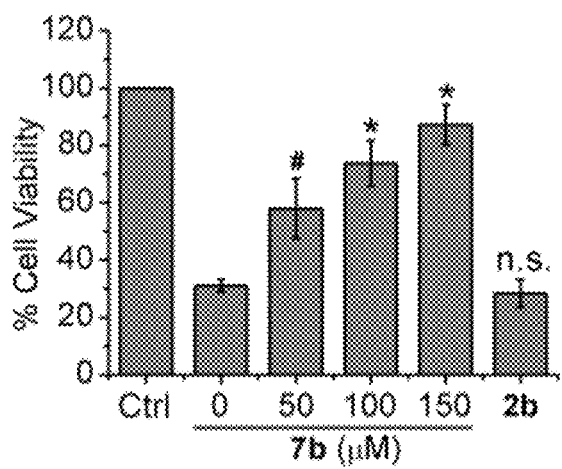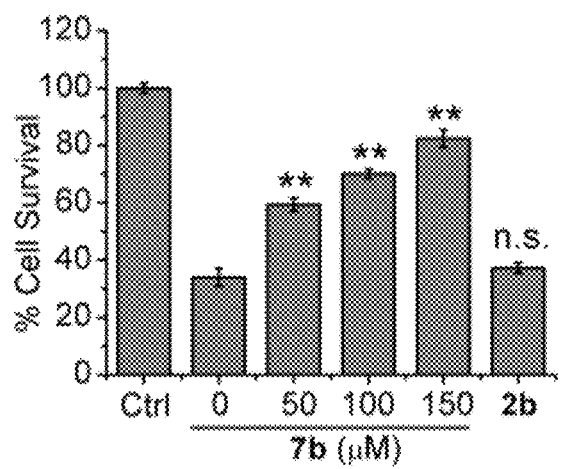
*Fig. 6a*          *Fig. 6b*

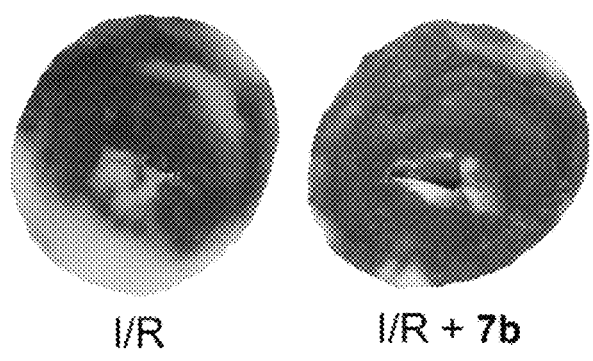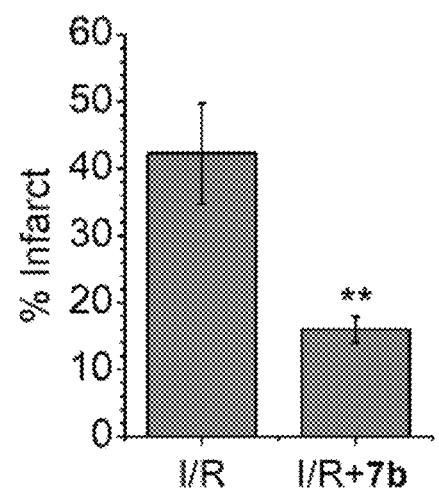
*Fig. 7a*  *Fig. 7b*

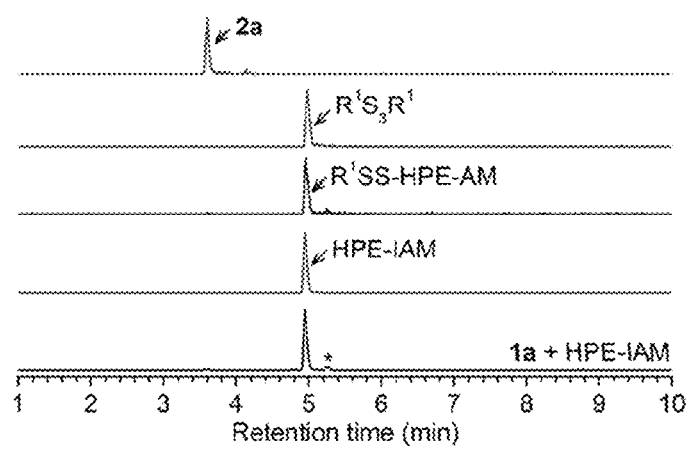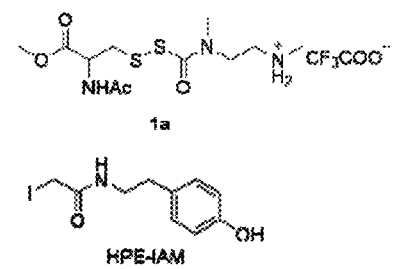
Fig. 8

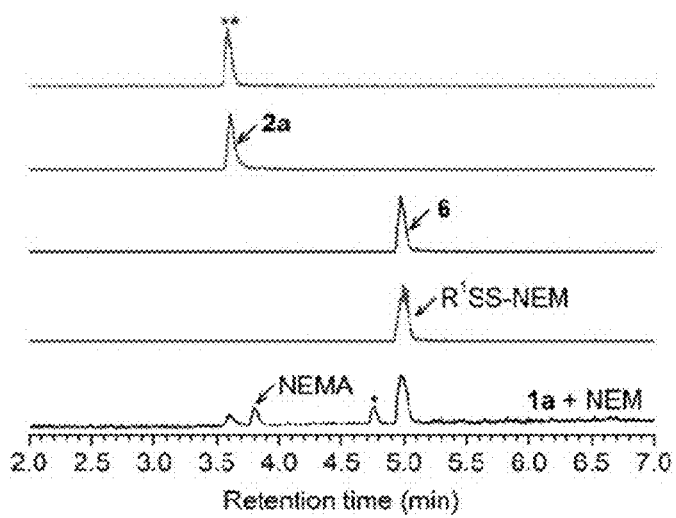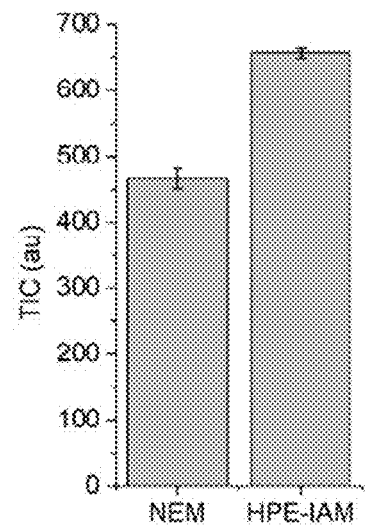
*Fig. 9a*  *Fig. 9b*

ALKYLAMINE-SUBSTITUTED PERTHIOCARBAMATES AS DUAL PRECURSORS TO HYDROPERSULFIDE AND CARBONYL SULFIDE

FEDERALLY SPONSORED RESEARCH OR DEVELOPMENT

This invention was made with government support under CHE1900285 awarded by the National Science Foundation. The government has certain rights in the invention.

BACKGROUND

The discovery of $H_2S$ as an endogenously produced signaling molecule has stimulated interest in $H_2S$-derived species as possible biological mediators. $H_2S$ signaling is proposed to occur via post-translational modification of protein cysteine residues (RSH) to form hydropersulfides (RSSH). Mustafa et al., 2009; Gadalla and Snyder, 2010; Filipovic et al., 2018; and Ju et al., 2017. Recent reports indicate that much of the biological effects attributed to $H_2S$ could instead be due to RSSH and polysulfides. Ida et al., 2014; Ono et al., 2014; and Toohey, 1986.

Several reports have shown that small molecule hydropersulfides, such as cysteine hydropersulfide (Cys-SSH), and glutathione hydropersulfide (GSSH), are ubiquitous and highly prevalent in mammalian cells, tissue, and plasma. Mustafa et al., 2009; Ida et al., 2014; Numakura et al., 2017; and Kunikata et al., 2017. Furthermore, numerous enzymes and proteins have been reported to have RSSH modifications at many cysteine residues. Massey and Edmondson, 1970; Branzoli and Massey, 1974; Dóka et al., 2016; Longen et al., 2016; and Wright et al., 2006. Recently, Akaike and co-workers have shown that Cys-SSH is biosynthesized and attached to tRNA by the cysteinyl tRNA synthetases (CARS), and subsequently is translationally incorporated into proteins. Akaike et al., 2017. The prevalent nature of RSSH in cells suggests that they could have important biological functions.

RSSH display distinct chemistry, which may be important for their biological utility. For example, RSSH are superior nucleophiles and more potent reductants than their corresponding thiols because of the presence of unshared electron pairs on the sulfur atom adjacent to the nucleophilic sulfur atom. Cuevasanta et al., 2015; Cuevasanta et al, 2019; and Saund et al., 2015. RSSH and related species have been proposed to behave as potent antioxidants and redox signaling intermediates. Ida et al., 2014; Ono et al., 2014; Numakura et al., 2017; Kunikata et al., 2017; Saund et al., 2015; Millikin et al., 2016; Shibata et al., 2016; Alvarez et al., 2017; and Yang et al., 2019. Recent reports have demonstrated that RSSH are efficient H-atom transfer agents toward alkyl, alkoxyl, peroxyl, and thiyl radicals, confirming their promise as potent antioxidants. Bianco et al., 2016; Chauvin et al., 2017. Unlike thiols, RSSH also can undergo transsulfuration reactions because of their electrophilic properties in the neutral state. Saund et al., 2015; Fukuto et al., 2018. The sulfane sulfur in RSSH can be reversibly transferred to other free thiols, such as glutathione (GSH) or cysteine (Cys-SH), to form GSSH or Cys-SSH, respectively. Furthermore, studies have suggested RSSH involvement in the detoxification of environmental electrophiles. Bianco et al., 2019; Lin et al., 2019; Shinkai and Kumagai, 2019. Yet, despite the increasing evidence of the role of RSSH in redox signaling, the biological functions of RSSH remain elusive. This deficiency is partly due to the instability of RSSH under physiological conditions.

Small molecule donors of reactive sulfur species are essential tools that can be used to elucidate their biological chemistry. To this end, several RSSH donors have been reported (FIG. 1, prior art). For example, precursors containing an activated disulfide bond have been developed to rearrange spontaneously at physiological pH thereby producing RSSH. Artaud and Galardon, 2014. A novel class of S-substituted-thioisothioureas was recently reported to be efficient RSSH precursors. Khodade and Toscano, 2018. Wang and co-workers have developed esterase-sensitive RSSH prodrugs and demonstrated their cardioprotective effects. Zheng et al., 2017. Similarly, Xian and co-workers have reported fluoride/acid-activated RSSH donors. Kang et al., 2018. Recently, $H_2O_2$-triggered self-immolative RSSH donors have been developed that exhibit cytoprotective effects against oxidative stress. Powell et al., 2018; Bora et al., 2018. These findings highlight the therapeutic potential of small molecule RSSH donors against oxidative stress-related diseases. Although chemical tools for RSSH generation have emerged, no convenient methodology for the controlled and extended release of RSSH over long time periods is currently available.

SUMMARY

In some aspects, the presently disclosed subject matter provides a compound of formula (I):

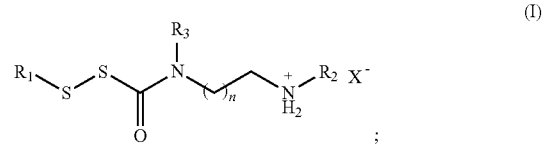

wherein: n is an integer selected from the group consisting of 0, 1, 2, 3, 4, 5, 6, 7, and 8; $R_1$ is selected from the group consisting of branched or unbranched alkyl, heterocycloalkyl, aryl, heteroaryl, a cysteine residue, a N-acetylcysteine residue, a homocysteine residue, a glutathione residue, and:

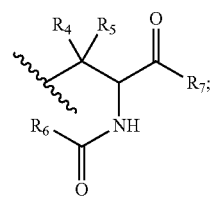

wherein: $R_4$ and $R_5$ are each independently selected from the group consisting of H, $C_1$-$C_4$ alkyl, and aryl; $R_6$ is $C_1$-$C_4$ alkyl or aryl; $R_7$ is —$OR_8$ or —$NR_9R_{10}$, wherein $R_8$, $R_9$, and $R_{10}$ are each independently selected from the group consisting of H, $C_1$-$C_4$ alkyl, and aryl; $R_2$ is selected from the group consisting of H, alkyl, aryl, and a functional group that responds to a stimulus selected from the group consisting of light, a redox reaction, and an enzymatic reaction; $R_3$ is selected from the group consisting of H, alkyl, and aryl; and $X^-$ is an anion.

In certain aspects, n is an integer selected from the group consisting of 1, 2, and 3.

In some aspects, the compound of formula (I) is:

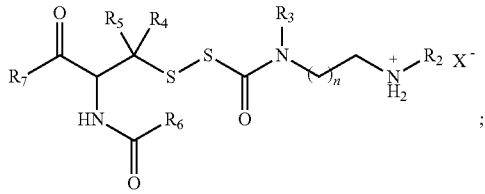

n is an integer selected from the group consisting of 1, 2, and 3; $R_4$ and $R_5$ are each independently H or $C_1$-$C_4$ alkyl; $R_6$ is $C_1$-$C_4$ alkyl or aryl; $R_7$ is —$OR_8$ or —$NR_9R_{10}$, wherein $R_8$, $R_9$, and $R_{10}$ are each independently selected from the group consisting of H, $C_1$-$C_4$ alkyl, and aryl; $R_2$ is selected from the group consisting of H, $C_1$-$C_4$ alkyl, and a functional group that responds to a stimulus selected from the group consisting of light, a redox reaction, and an enzymatic reaction; $R_3$ is selected from the group consisting of H, alkyl, and aryl; and $X^-$ is an anion.

In particular aspects, the compound of formula (I) is:

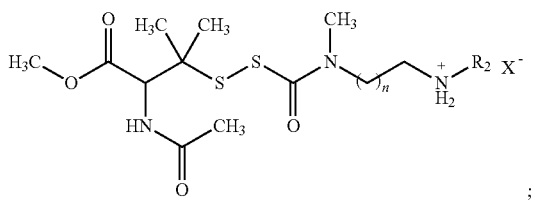

wherein: n is 1 or 2; and $R_2$ is H or $CH_3$.

In more particular aspects, the compound of formula (I) is selected from the group consisting of:

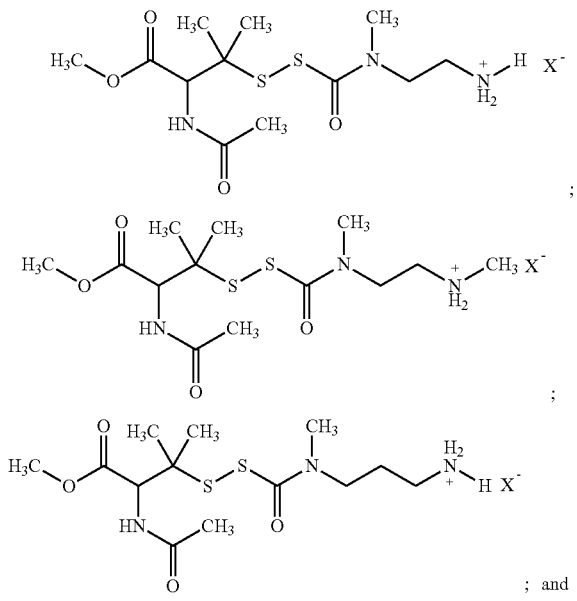

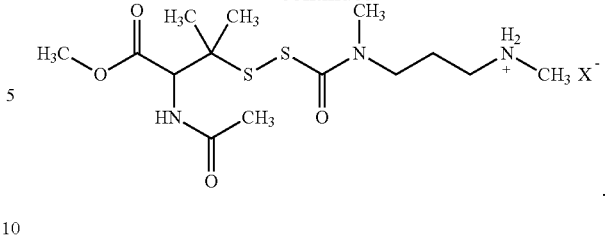

In certain aspects, $X^-$ is selected from the group consisting of $Cl^-$, $Br^-$, $(PO_4)^{3-}$, $CF_3COO^-$, $CH_3COO^-$, and $C_6H_5COO^-$. In more certain aspects, the compound of formula (I) is selected from the group consisting of:

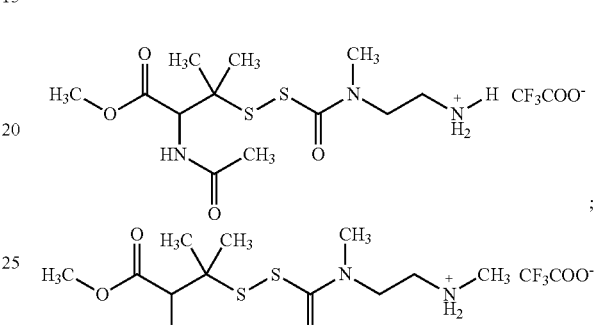

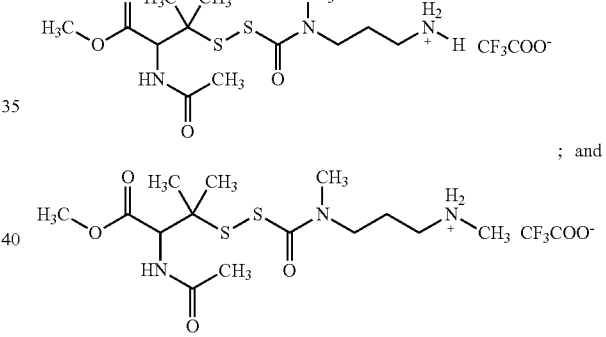

In some aspects, the presently disclosed subject matter provides a pharmaceutical composition comprising a compound of formula (I) and a pharmaceutically acceptable carrier.

In other aspects, the presently disclosed subject matter provides a kit comprising a compound of formula (I) or a pharmaceutical composition thereof.

In yet other aspects, the presently disclosed subject matter provides a method for treating a disorder, disease, or condition associated with oxidative stress in a subject in need of treatment thereof, the method comprising administering to the subject a therapeutically effective amount of a compound of formula (I) or a pharmaceutical composition thereof.

In particular aspects, the disorder, disease, or condition associated with oxidative stress comprises ischemia/reperfusion injury. In yet more particular aspects, the treating comprises preventing, reducing the occurrence of or severity of, or protecting against ischemia/reperfusion injury. In certain aspects, the ischemia/reperfusion injury comprises myocardial ischemia/reperfusion injury.

In other aspects, the presently disclosed subject matter provides a method for preventing or reducing ischemia/reperfusion injury to an organ to be transplanted, the method comprising administering to or contacting the organ with a therapeutically effective amount of a compound of formula (I) or a pharmaceutical composition thereof.

Certain aspects of the presently disclosed subject matter having been stated hereinabove, which are addressed in whole or in part by the presently disclosed subject matter, other aspects will become evident as the description proceeds when taken in connection with the accompanying Examples and Drawings as best described herein below.

BRIEF DESCRIPTION OF THE DRAWINGS

Figure 2:
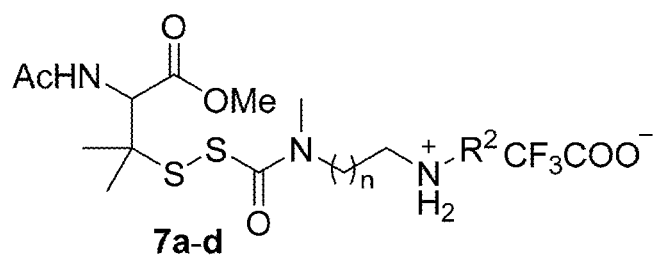

Having thus described the presently disclosed subject matter in general terms, reference will now be made to the accompanying Figures, which are not necessarily drawn to scale, and wherein:

FIG. 1 is selected small molecule RSSH and COS/H$_2$S donors (PRIOR ART);

FIG. 2 shows structures of RSSH precursors 7a-d with synthetic yields.

Figure 3A:
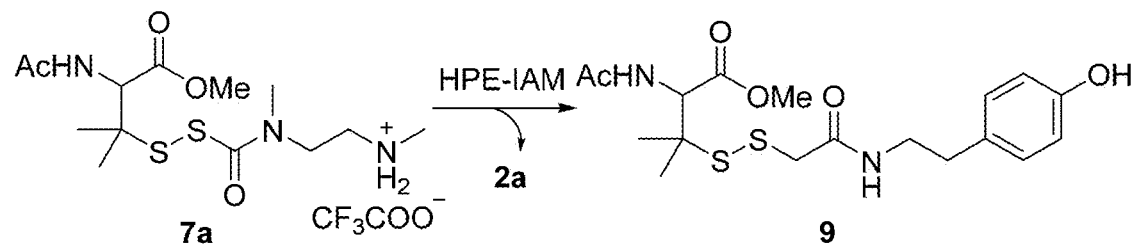
Figure 3B:
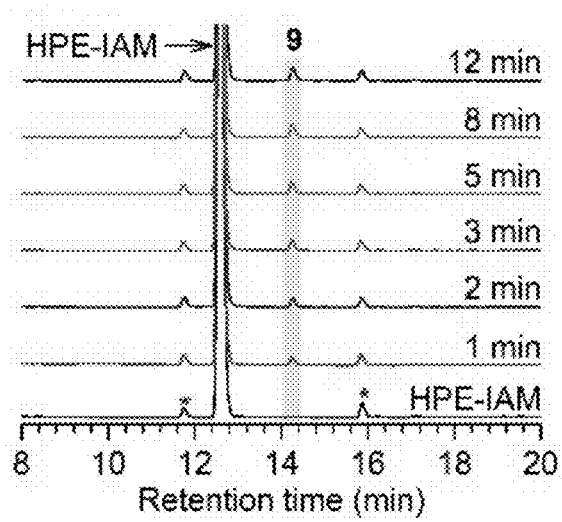
Figure 3C:
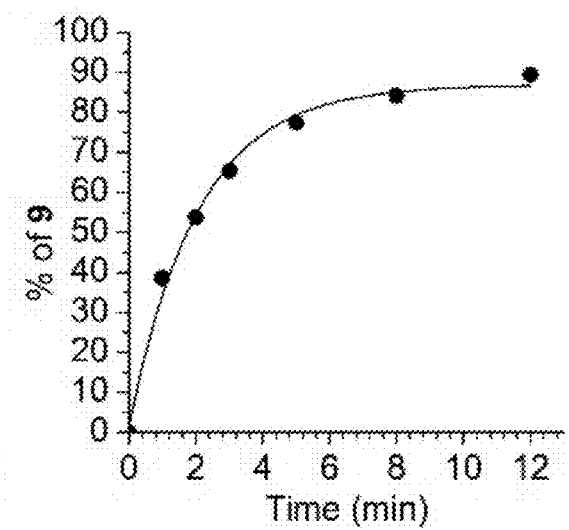
Figure 4:
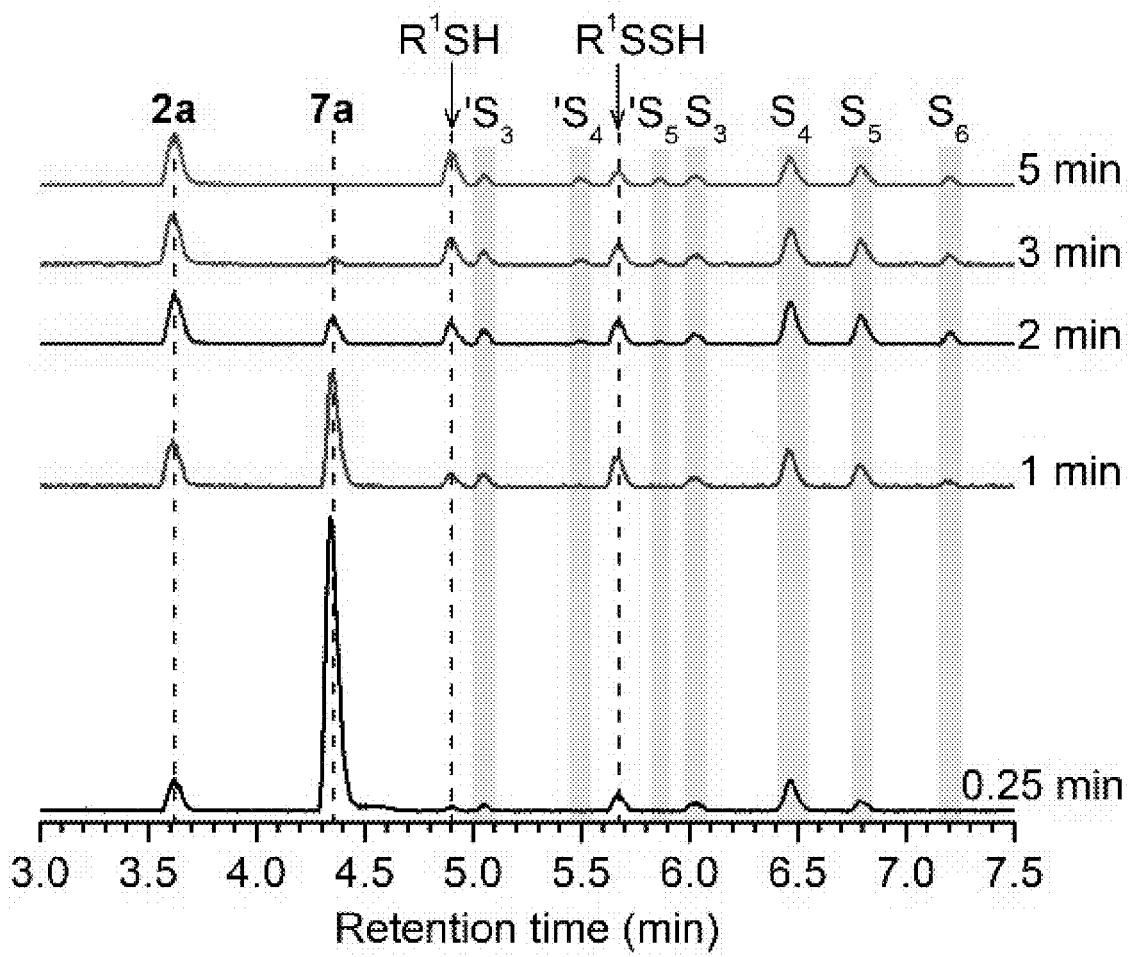
Figure 10:
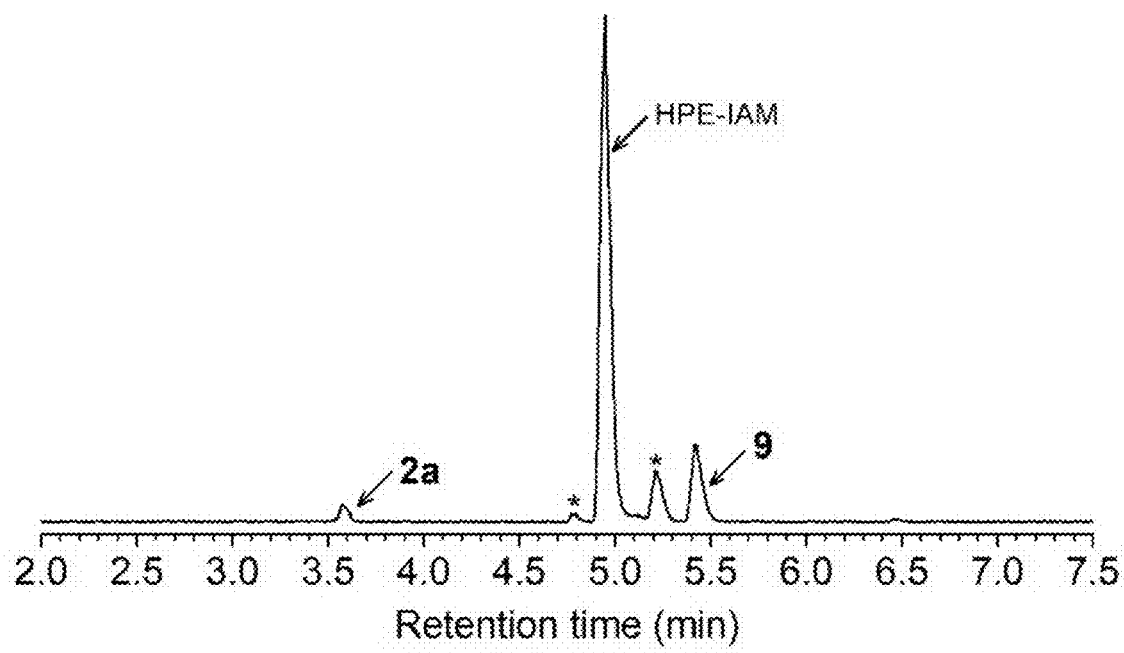
Figure 11:
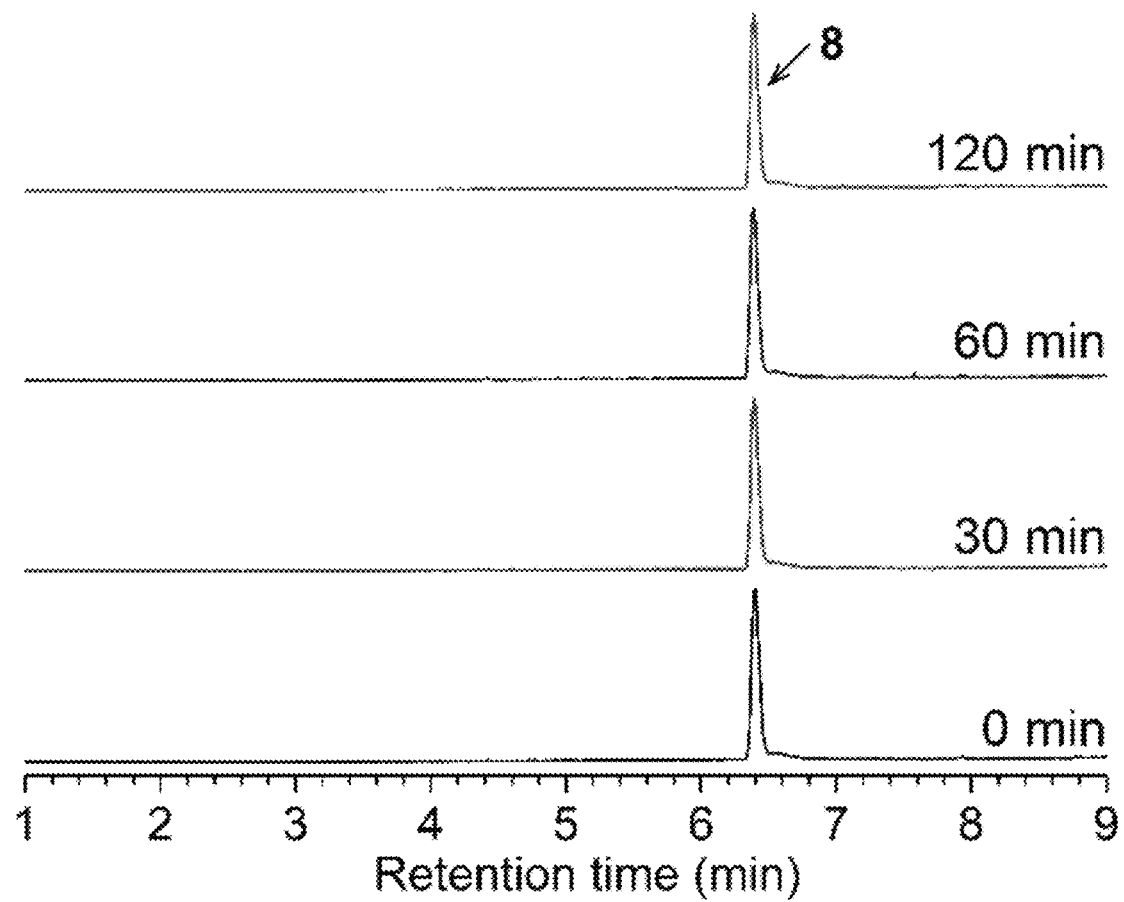
Figure 12:
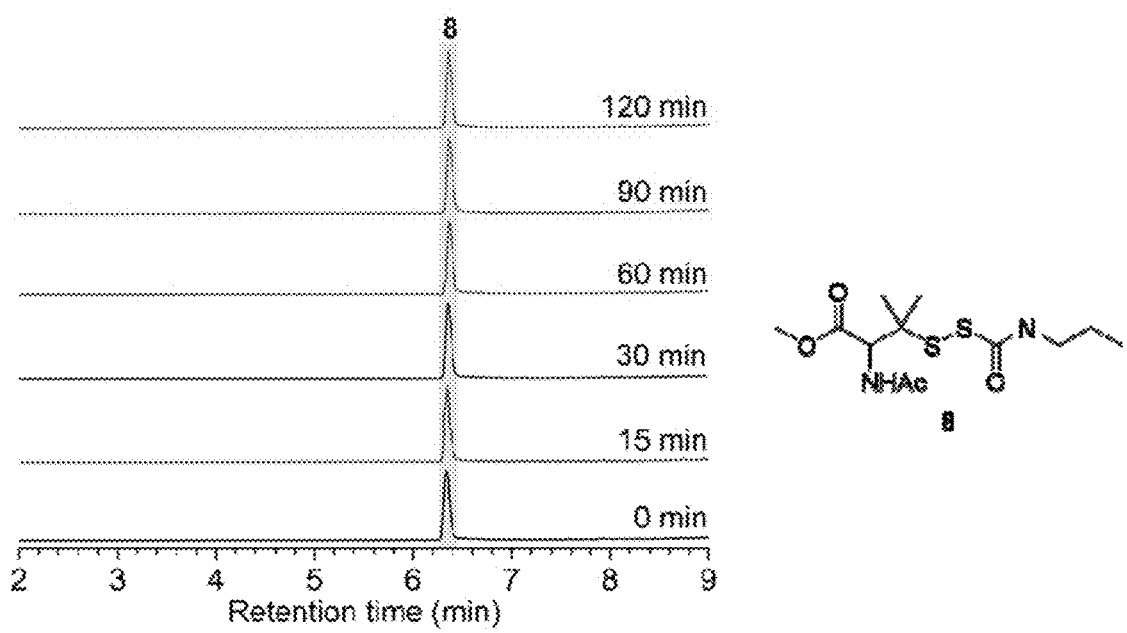
Figure 13:
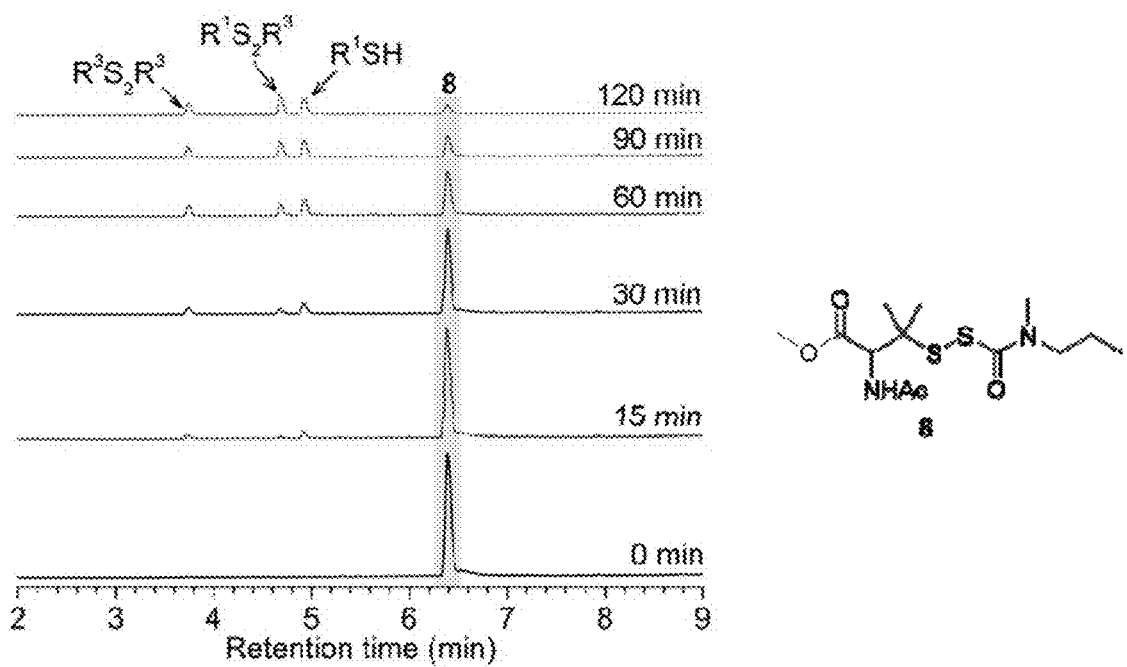
Figure 14:
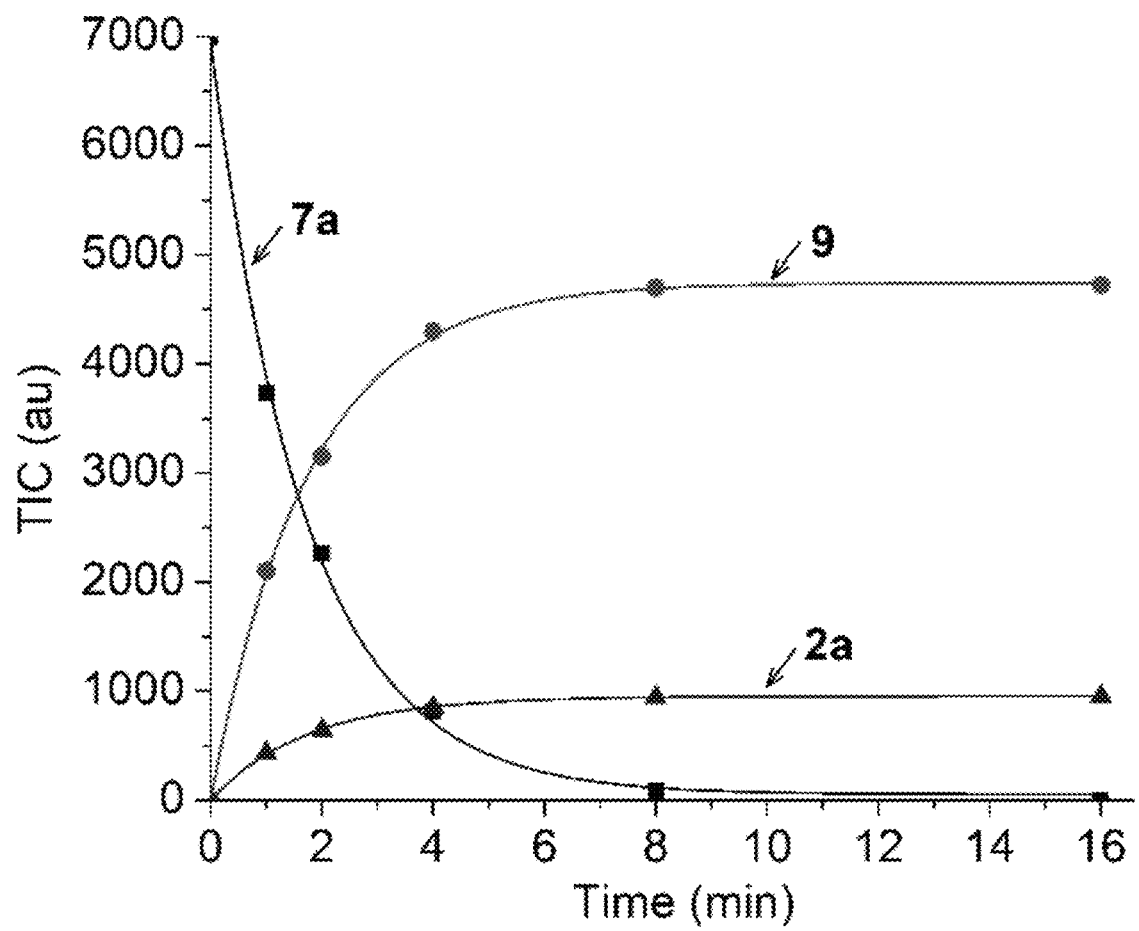
Figure 15:
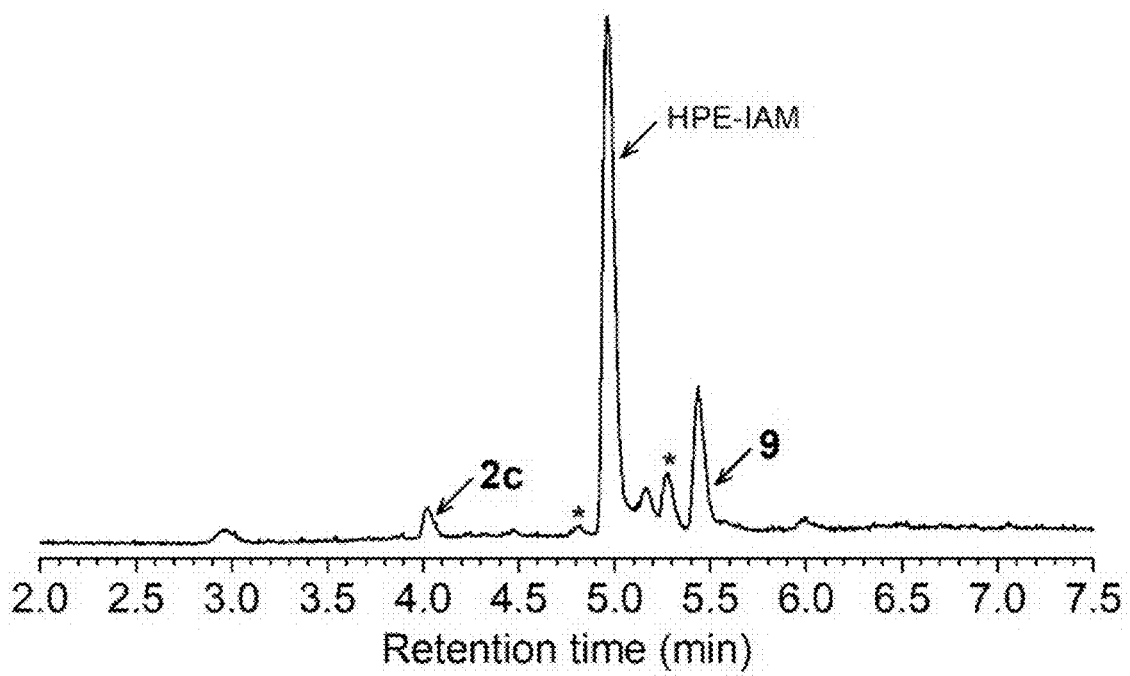
Figure 16:
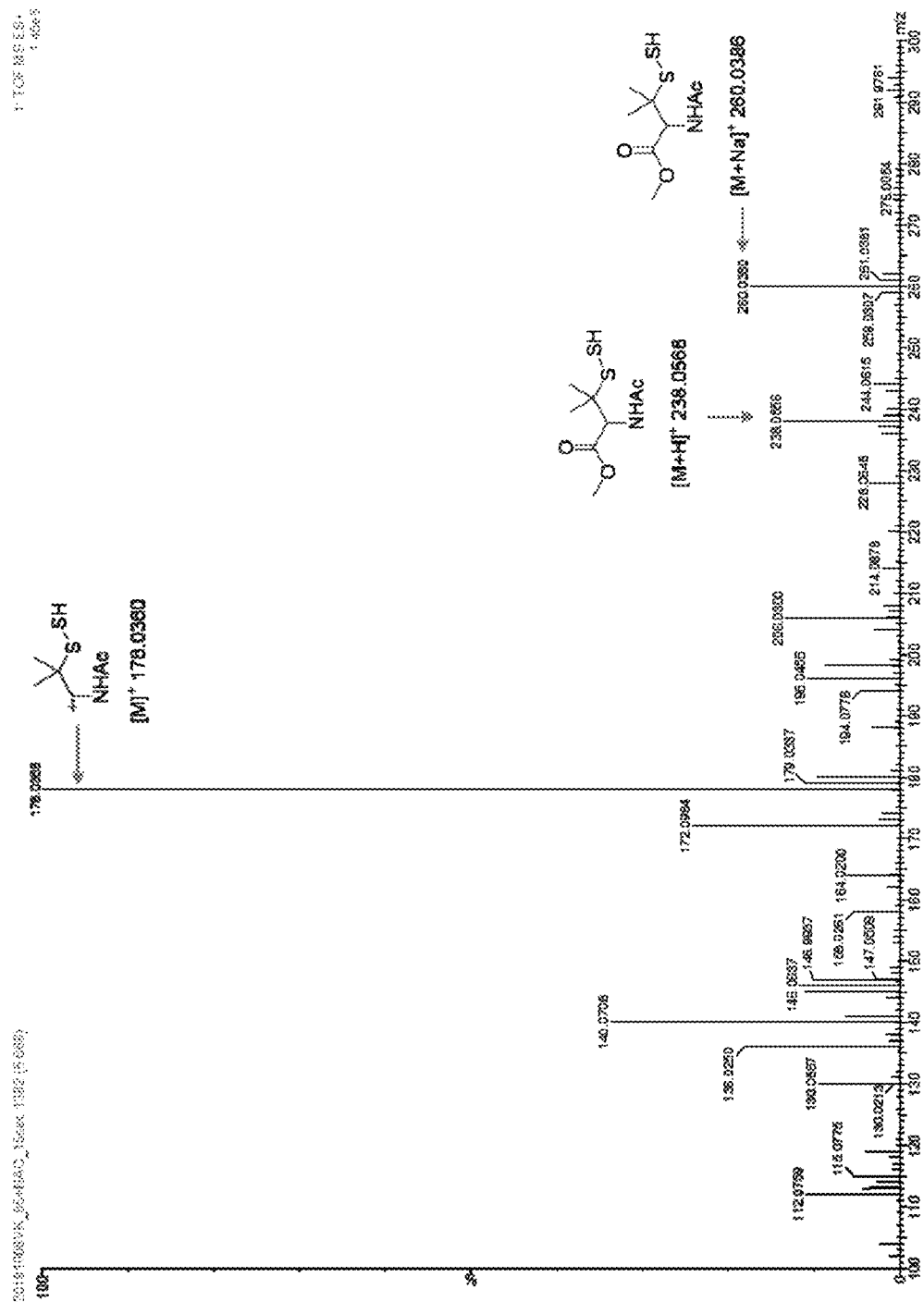
Figure 17:
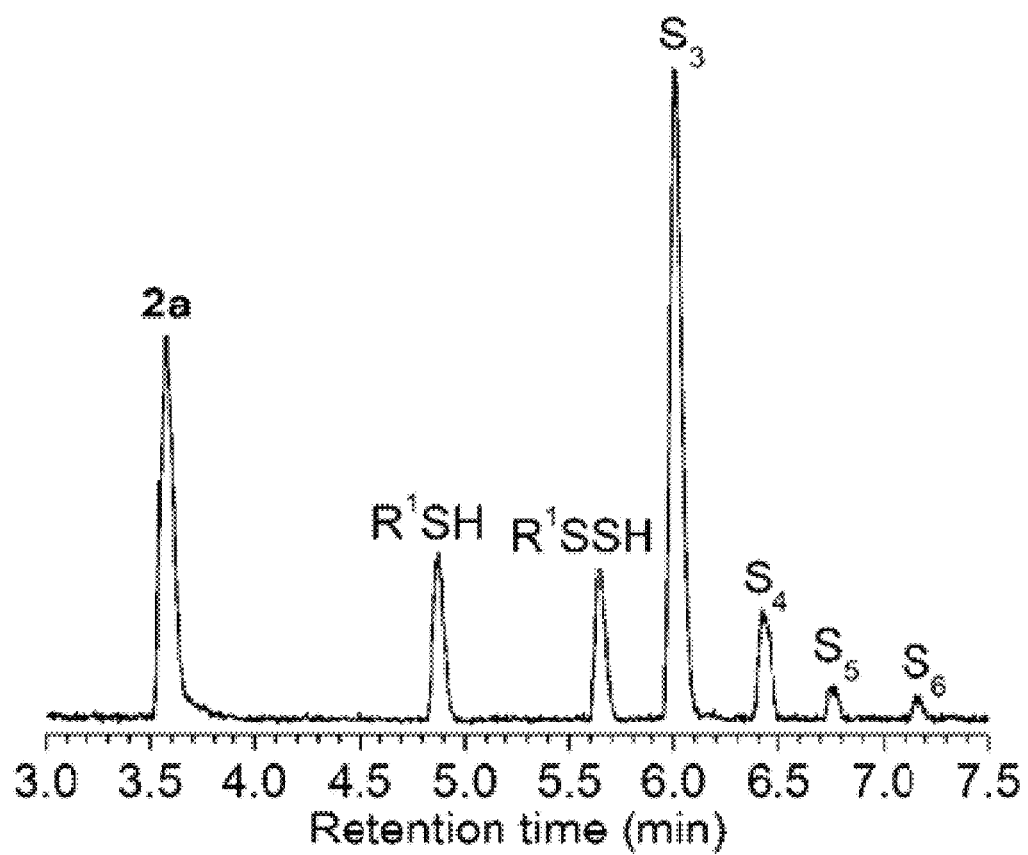
Figure 18:
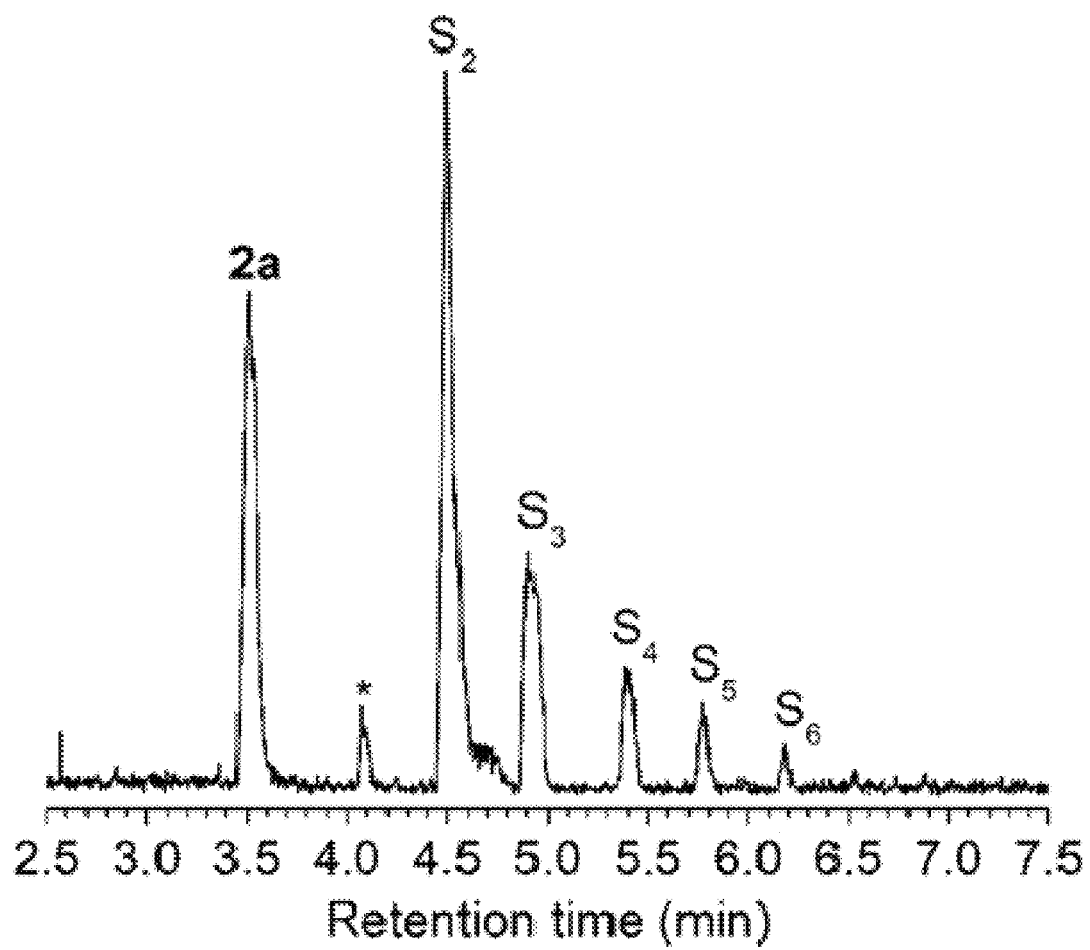
Figure 19:
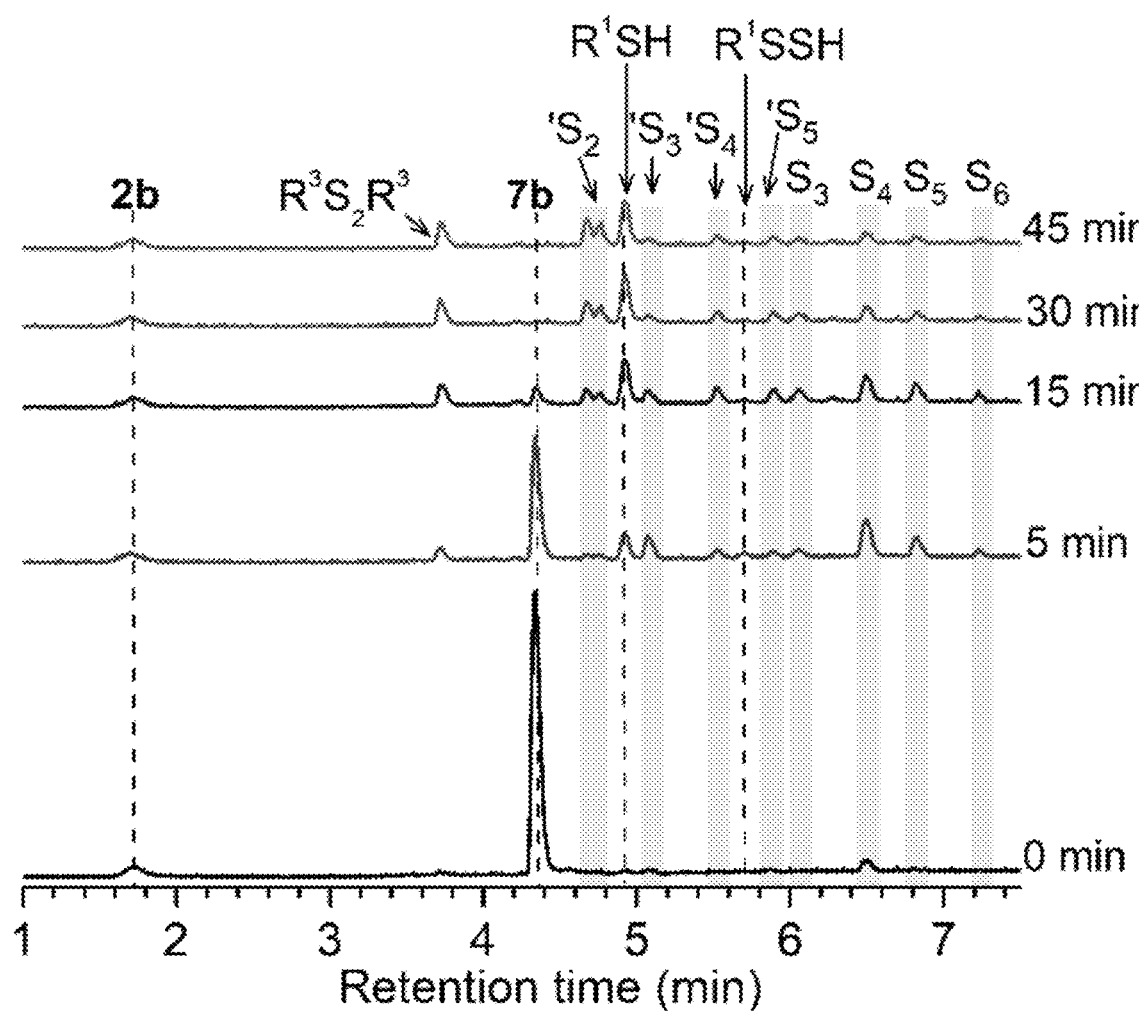
Figure 20:
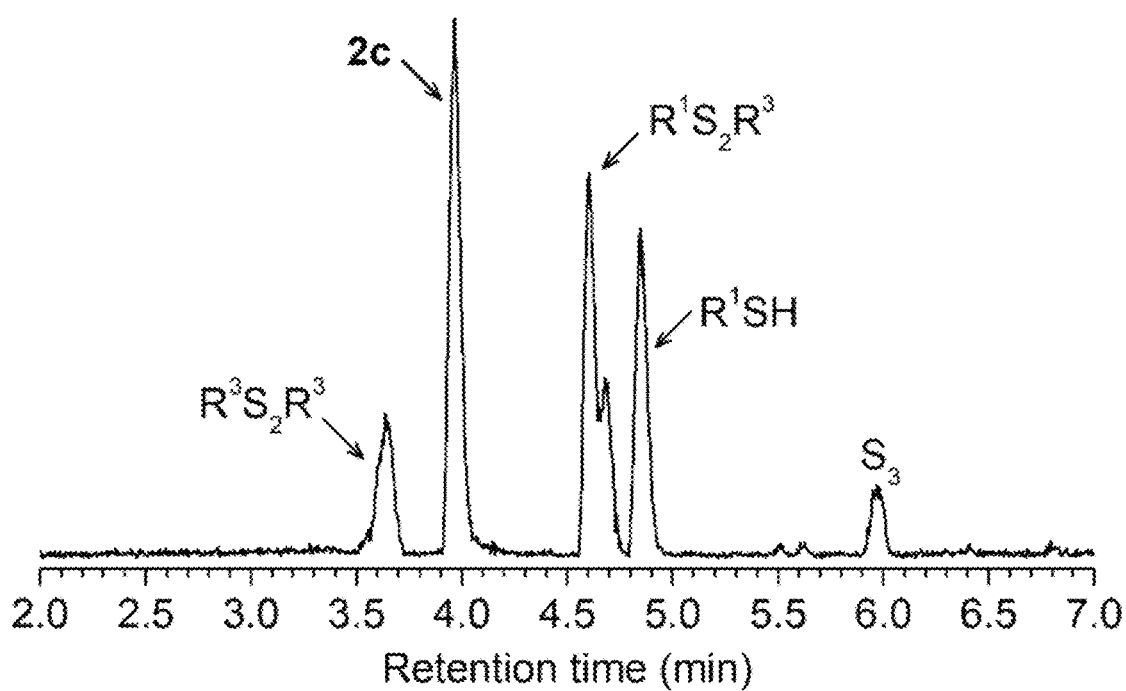
Figure 21:
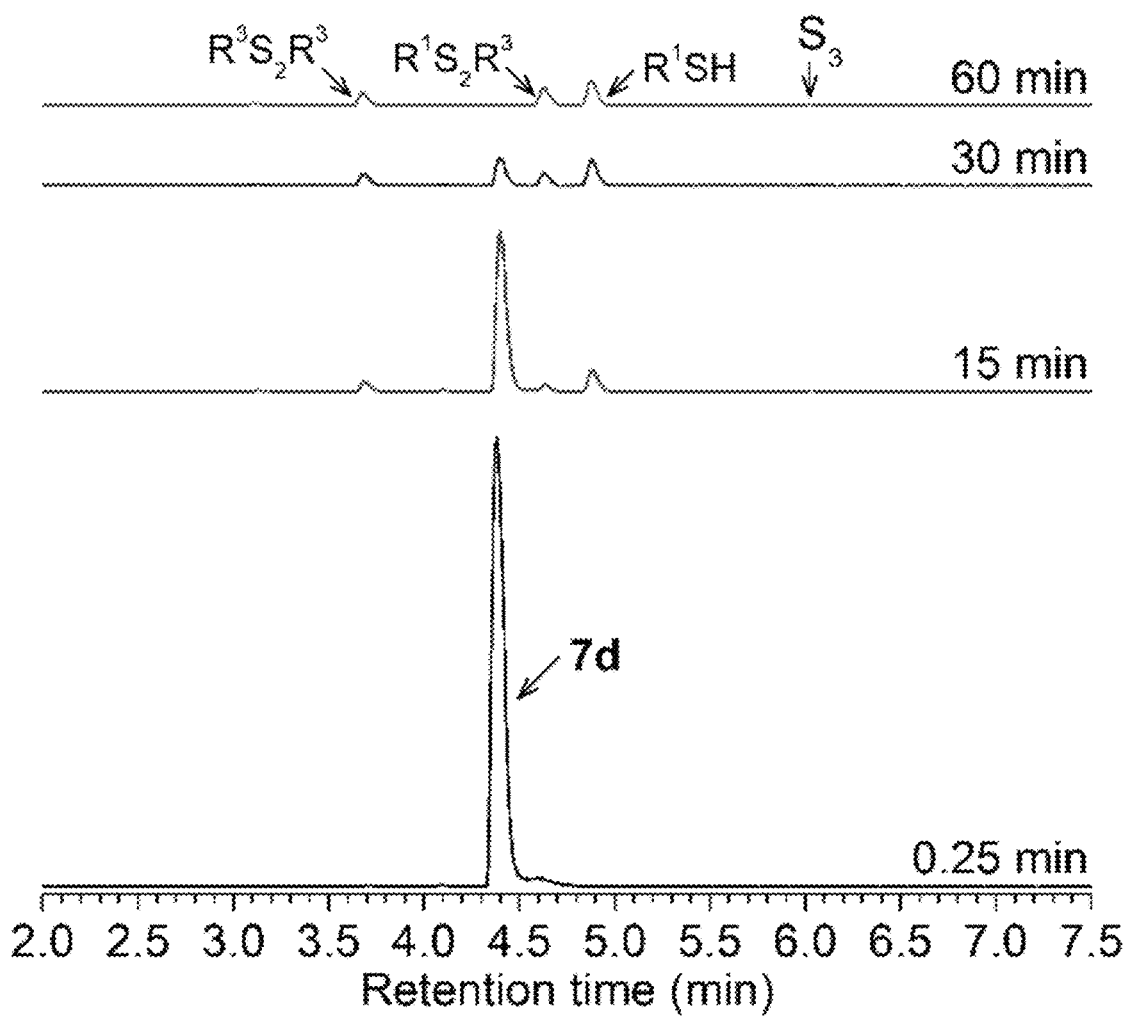
Figure 22:
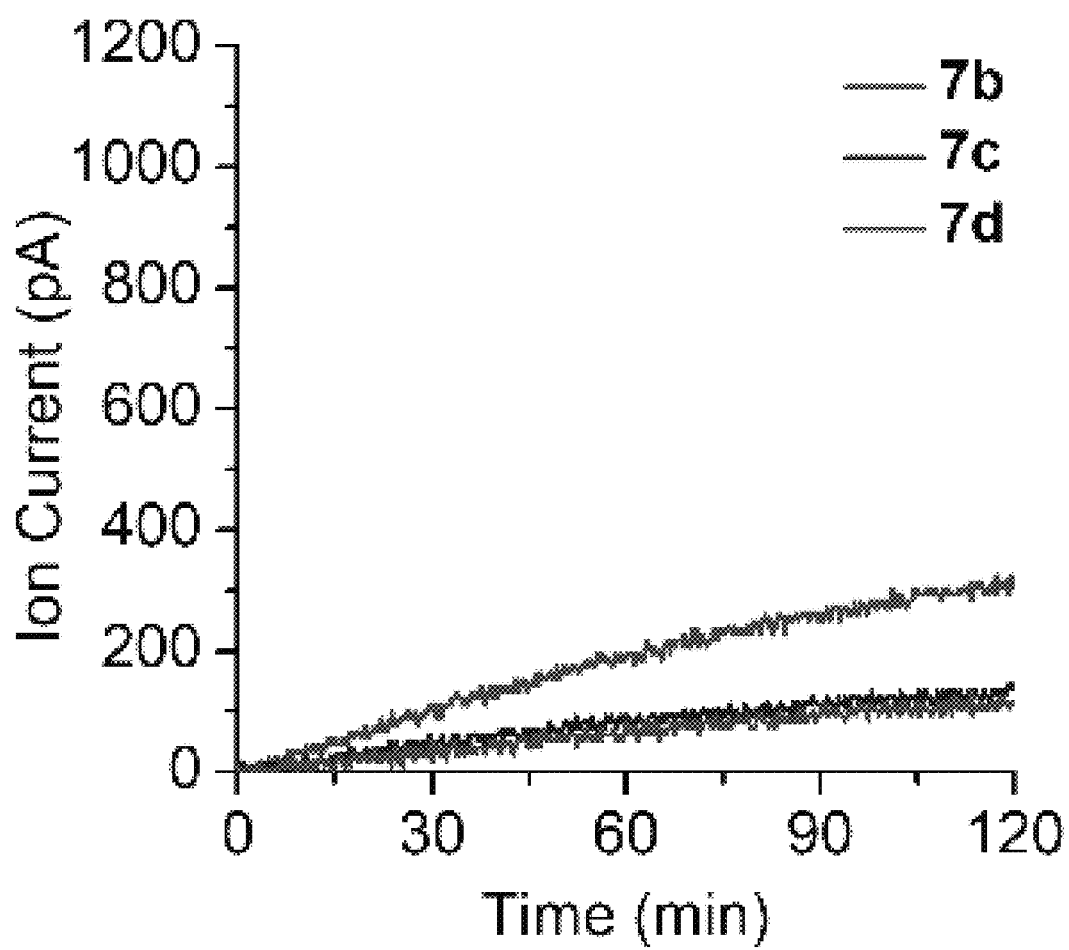
Figures 23A, 23B:
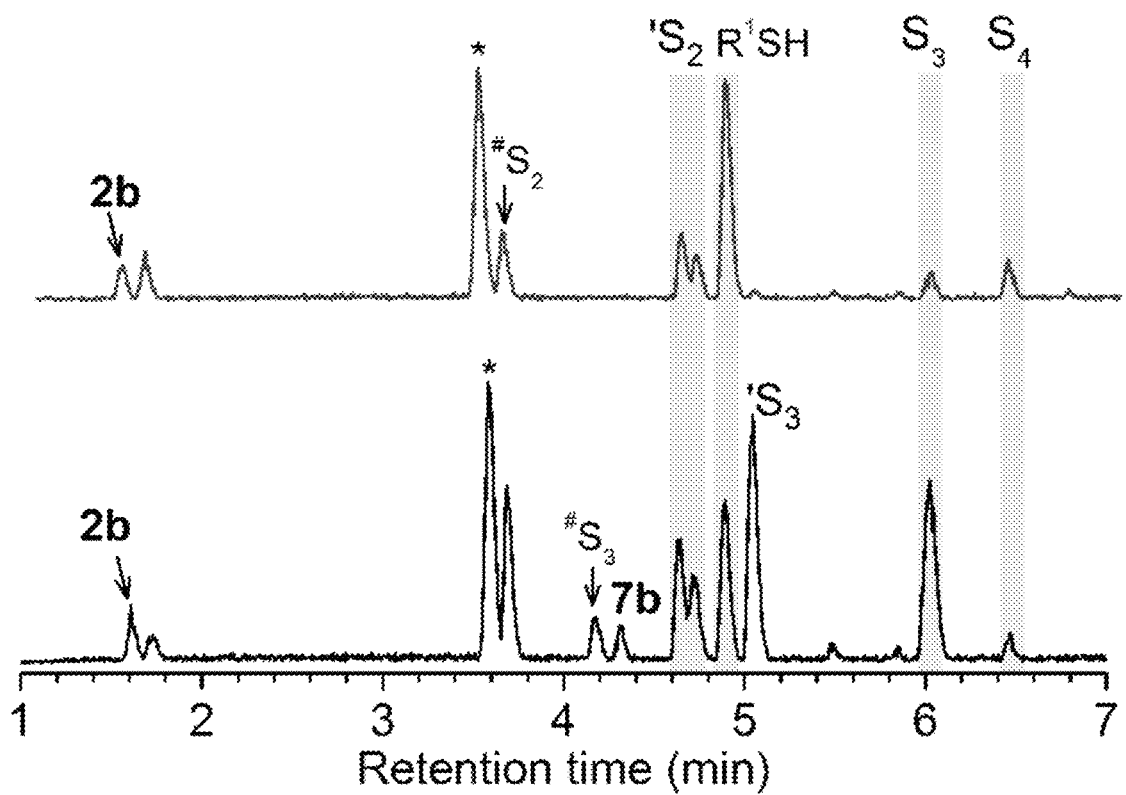
Figure 24:
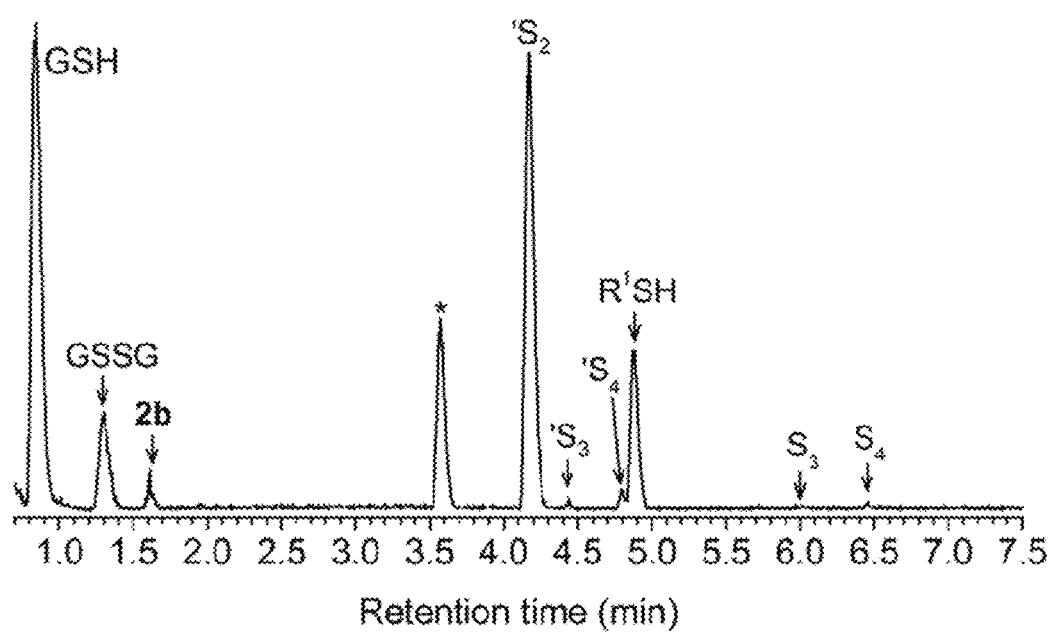
Figure 25:
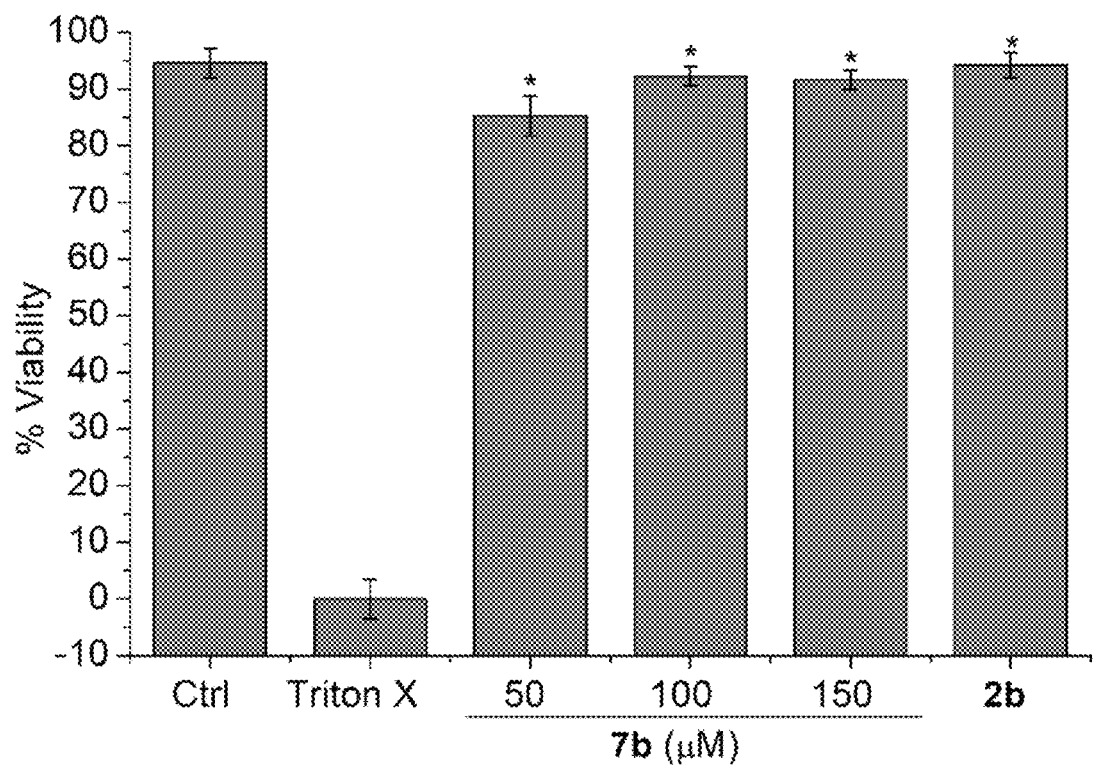
Figure 26:
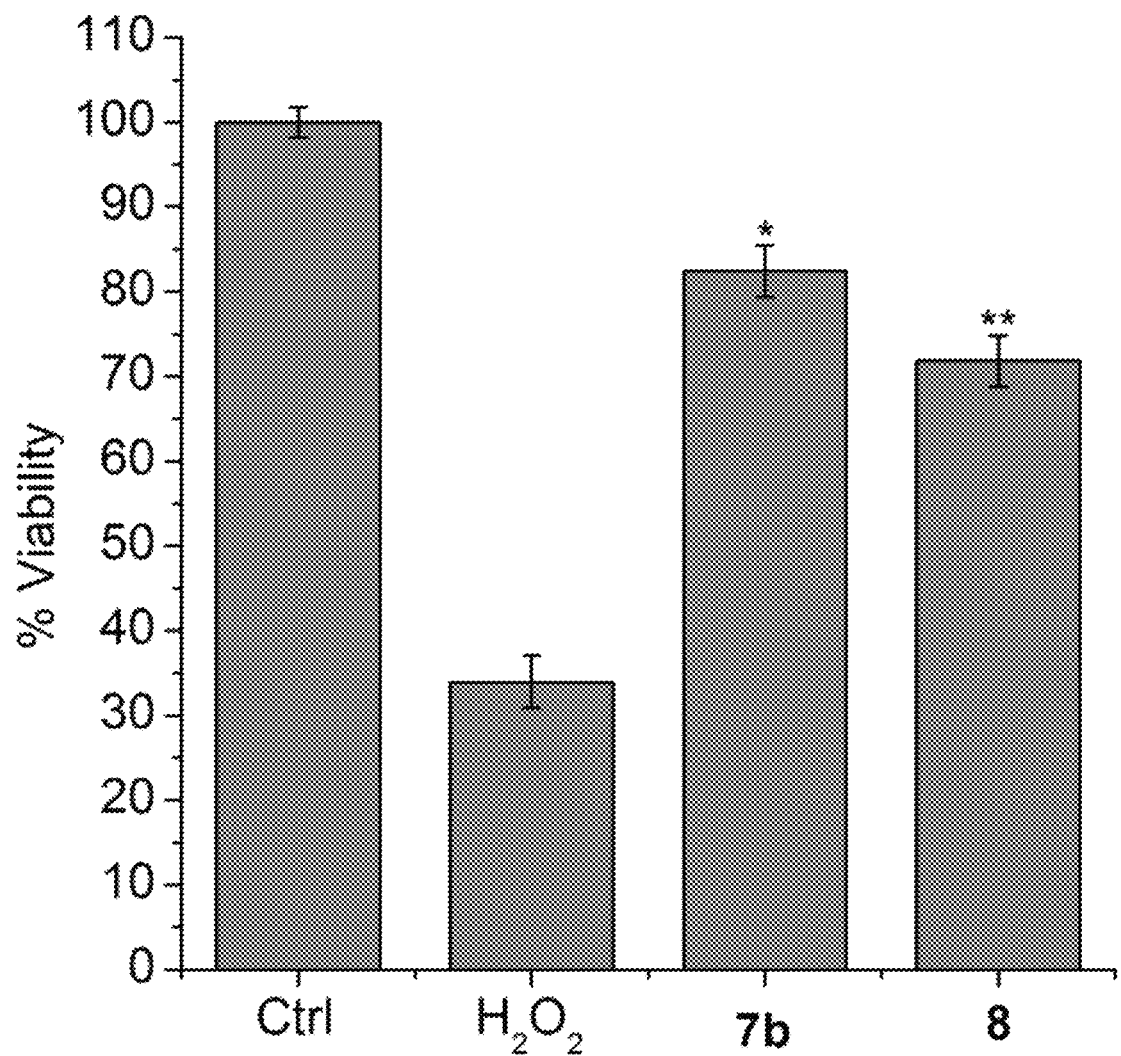

FIG. 3a, FIG. 3b, and FIG. 3c are: (FIG. 3a) Reaction scheme showing RSSH generation from 7a in the presence of HPE-IAM; (FIG. 3b) HPLC analysis of RSSH generation from 7a (100 μM) in the presence of HPE-IAM (5 mM) incubated in pH 7.4 phosphate buffer (100 mM) with DTPA (100 μM) at 37° C. An aliquot of the reaction mixture was withdrawn at the specified time and quenched with 1% formic acid. Asterisks indicate the presence of impurities in the commercial HPE-IAM sample; and (FIG. 3c) Kinetics of RSS-HPE-AM 9 generation. Data represent the average±SD (n=3). The curve is the calculated best fit to a single-exponential function (k=0.505±0.019 min$^{-1}$; t$_{1/2}$=1.4±0.1 min);

FIG. 4 shows UPLC-MS chromatograms of RSSH generation from 7a (100 μM) in the presence of NAC (500 μM) incubated in pH 7.4 ammonium bicarbonate (50 mM) with the metal chelator DTPA (100 μM) at 37° C. Aliquots taken at various times were quenched with 1% formic acid, and analyzed by UPLC-MS. A peak at 5.67 min attributed to RSSH is observed under these conditions. RSSH-derived symmetrical dialkyl polysulfide, labeled as S$_3$ to S$_6$ (R$^1$SS$_n$SR$^1$, n=1-4, cyan highlight), and unsymmetrical dialkyl polysulfides labeled as 'S$_3$ to 'S$_5$ (R$^1$SS$_n$SR$^3$, n=1-3, pink highlight) formation is evident. A peak at 3.62 min attributed to the byproduct 2a also is observed;

FIG. 5a and FIG. 5b show COS measurement using MIMS generated from 7a-d (50 μM) either (FIG. 5a) without NAC or (FIG. 5b) with NAC (0.25 mM, 5 equiv.) in pH 7.4 phosphate buffer saline (10 mM) with DTPA (100 μM) at 37° C.;

FIG. 6a and FIG. 6b show results from H9c2 cardiac myoblasts pretreated with the RSSH precursor 7b at (50, 100 and 150 μM) and the byproduct 1-methylimidazolidin-2-one (2b) at 150 μM for 2 h followed by exposure to H$_2$O$_2$ (200 μM) for 2 h. (FIG. 6a) Quantification of viability was carried out using Cell Counting Kit-8 (CCK-8). Results are expressed as the mean±SEM (n=5 for each treatment group) with three independent experiments. (FIG. 6b) Quantification of cytotoxicity was carried out using SYTOX® Green nucleic acid stain. Results are expressed as the mean±SEM (n=5 for each treatment group) with five independent experiments. #P<0.05, * P<0.01, ** P<0.001 for comparisons with the H$_2$O$_2$ treatment group. Group comparisons are determined by a one-way analysis of variance (ANOVA) with Dunnett's correction post-hoc test using GraphPad Prism 8;

FIG. 7a and FIG. 7b show the cardioprotective effects of 7b postconditioning in the isolated-perfused murine heart. (FIG. 7a) Representative images of coronal slices of the heart following TTC staining. (FIG. 7b) Comparison of the volume of infarcted tissue following ischemia-reperfusion and when the heart is conditioned with precursor 7b (100 μM) at the onset of reperfusion. Results are expressed as the mean±SEM (n=4 for each treatment group) with four independent experiments. ** P<0.001 for comparisons with the IR group. Group comparisons are determined by a one-way analysis of variance (ANOVA) with Dunnett's correction post-hoc test using GraphPad Prism 8;

FIG. 8 shows RSSH generation from 1a (10 μM) in the presence of HPE-IAM (500 μM) in pH 7.4 ammonium bicarbonate buffer at 37° C. for 15 min analyzed by UPLC-MS (bottom chromatogram). Under these conditions, R$^1$SS-HPE-AM (5), dialkyltrisulfide R$^1$S$_3$R$^1$ (6), and HPE-IAM coeluted. Hence, individual mass extracted chromatograms are shown separately. The byproduct 1,3-dimethyl-2-imidazolidinone (2a) formation also is observed. The asterisk indicates the presence of small amount of impurities in the commercial HPE-IAM sample;

FIG. 9a and FIG. 9b show: (FIG. 9a) RSSH generation from 1a (10 μM) in the presence of NEM (500 μM) in pH 7.4 ammonium bicarbonate buffer at 37° C. for 15 min analyzed by UPLC-MS (bottom chromatogram). R$^1$SS-NEM and dialkyltrisulfide 6 coeluted; hence individual mass extracted chromatograms are shown separately. Also, the byproduct 2a and internal standard 4-hydroxyphenylacetamide (labeled as **) coeluted at 3.6 min. Under these conditions, 7.4±0.2 μM of 2a formation is observed. A peak at 3.7 min corresponding to N-ethylmaleamic acid (NEMA), derived from NEM hydrolysis, is observed. The asterisk represents a minor amount of thiol-NEM adduct formation, suggesting that excess NEM reacts with R$^1$SS-NEM adduct to produce R$^1$S-NEM, Bogdándi et al., 2019; (FIG. 5b) Comparison of dialkyltrisulfide 6 formation from 1a in the presence of NEM and HPE-IAM under similar conditions;

FIG. 10 is a representative UPLC-MS chromatogram of RSS-HPE-AM 9 generation from 7a (10 μM) incubated with HPE-IAM (500 μM) in pH 7.4 ammonium bicarbonate buffer at 37° C. for 15 min. Under these conditions, 8.7±0.4 μM of byproduct 1,3-dimethyl-2-imidazolidinone (2a) formation is observed. The asterisk indicates the presence of small amount of impurities in the commercial HPE-IAM sample;

FIG. 11 shows the stability of control compound 8 at pH 7.4. FIG. 11 is an UPLC-MS chromatogram of 8 (100 μM) incubated in pH 7.4 ammonium bicarbonate buffer at 37° C. Aliquots taken at various times were quenched with 1% formic acid and analyzed by UPLC-MS. These data indicate that control compound 8 is stable under these conditions and does not produce RSSH;

FIG. 12 shows UPLC-MS chromatograms of control compound 8 (100 μM) reaction with n-BuNH$_2$ (500 μM) in pH 7.4 ammonium bicarbonate:acetonitrile (9:1) with the metal chelator DTPA (100 μM) at 37° C. Aliquots (200 μL) were taken at specified time points, quenched with 1% formic acid (200 μL) and analyzed using UPLC-MS. The lack of reaction of 8 with n-BuNH$_2$ indicates no RSSH release via this intermolecular reaction;

FIG. 13 is UPLC-MS chromatograms of control compound 8 (100 μM) reaction with NAC (500 μM) in pH 7.4 ammonium bicarbonate (50 mM) with the metal chelator DTPA (100 μM) at 37° C. Aliquots (200 μL) were taken at specified time points, quenched with 1% formic acid (200 μL) and analyzed using UPLC-MS;

FIG. 14 shows the kinetics of decomposition of 7a (20 μM) in the presence of HPE-IAM (1 mM) and formation of 2a and 9 in ammonium bicarbonate buffer (50 mM) with DTPA (100 μM) analyzed using UPLC-MS. An aliquot of the reaction mixture was withdrawn at the specified time and quenched with 1% formic acid. The curves are the calculated best fits to a single-exponential function. The pseudo-first order rate constants for 7a, 9 and 2a are 0.59±0.02, 0.57±002, and 0.58±0.03 $min^{-1}$, respectively;

FIG. 15 is a representative UPLC-MS chromatogram of RSS-HPE-AM 9 generation from 7c (10 μM) incubated with HPE-IAM (500 μM) in ammonium bicarbonate pH 7.4 buffer at 37° C. for 7 h. Under these conditions, 8.8±0.2 μM of 1,3-dimethyltetrahydropyrimidin-2(1H)-one (2c) formation is observed. The asterisk indicates the presence of small amount of impurities in the commercial HPE-IAM sample. A peak at 5.2 min represents a minor amount of thiol-HPE-AM adduct formation, suggesting that excess of HPE-IAM reacts with 9 to produce RS-HPE-AM. A peak at 2.95 min corresponding to the β-(4-hydroxyphenyl)ethyl-2-amino-acetamide, presumably formed by the ammonolysis of HPE-IAM;

FIG. 16 is an HRMS of the peak eluting at 5.67 min corresponding to $R^1SSH$;

FIG. 17 shows RSSH generation from 7a (100 μM) in the absence of HPE-IAM in pH 7.4 ammonium bicarbonate buffer with DTPA (100 μM) at 37° C. for 10 min. RSSH and RSSH-derived symmetrical dialkyl polysulfides (labeled as $S_2$ to $S_6$) formation were observed under these conditions;

FIG. 18 shows decomposiion of precursor 1a (100 μM) in the absence of IPE-IAM incubated in pH 7.4 ammonium bicarbonate buffer (50 mM) with DTPA (100 μM) at 37° C. for 10 min. Evidence of an MS-observable RSSH peak was not observed, which is consistent with the relatively unstable nature of primary alkyl RSSH;

FIG. 19 shows UPLC-MS chromatograms of RSSH generation from 7b (100 μM) in the presence of NAC (500 μM) incubated in pH 7.4 ammonium bicarbonate (50 mM) with DTPA (100 μM) at 37° C. Aliquots taken at various times were quenched with 1% formic acid and analyzed by UPLC-MS. A peak at 5.67 min attributed to RSSH is observed under these conditions. RSSH-derived symmetrical dialkyl disulfides labeled as $S_3$ to $S_6$ ($R^1SS_nSR^1$, n=1-4, cyan highlight), and unsymmetrical dialkyl disulfides labeled as '$S_2$ to '$S_5$ ($R^3SS_nSR^1$, n=0-3, pink highlight) were observed;

FIG. 20 shows UPLC-MS chromatograms of RSSH generation from 7c (100 μM) in the presence of NAC (500 μM) incubated in pH 7.4 ammonium bicarbonate (50 mM) with DTPA (100 μM) at 37° C. for 60 min. An aliquot (200 μL) was taken, quenched with 1% formic acid (200 μL) and analyzed by UPLC-MS. A peak at 3.64 min attributed to N-acetyl cystine ($R^3S_2R^3$), formed by NAC reaction with unsymmetrical disulfide ($R^1S_2R^3$), is observed under these conditions. A minor amount of RSSH-derived dialkyl trisulfides ($S_3$) is also observed, indicating that RSSH release from 7c under these conditions;

FIG. 21 shows UPLC-MS chromatograms of RSSH generation from 7d (100 μM) in the presence of NAC (500 μM) incubated in pH 7.4 ammonium bicarbonate (50 mM) with DTPA (100 μM) at 37° C. Aliquots (200 μL) were taken at specified time points, quenched with 1% formic acid (200 μL) and analyzed using UPLC-MS. A peak at 3.64 min attributed to N-acetyl cystine ($R^3S_2R^3$) is observed under these conditions. A minor amount of RSSH-derived dialkyl trisulfides ($S_3$) formation indicates that the precursor 7d mainly reacts with NAC to produce the $R^1S_2R^3$, and the RSSH-generation path is minor under these conditions;

FIG. 22 is the MIMS measurement of COS generated from 7b-d (50 μM) with NAC (0.25 mM, 5 equiv.) in pH 6.0 phosphate buffer containing DTPA (100 μM) at 37° C.;

FIG. 23a and FIG. 23b show: (FIG. 23a) RSSH generation from 7b (100 μM) in the presence of NAC (500 μM) in pH 7.4 ammonium bicarbonate (50 mM) with DTPA (100 μM) at 37° C. for 45 min. (FIG. 23b) RSSH generation from 7b (100 μM) in the presence of NAC (500 μM) in pH 6.0 ammonium acetate buffer (50 mM) with DTPA (100 μM) at 37° C. for 12 h. The presence of RSSH precursor peak after 12 h incubation at pH 6.0 demonstrates slow RSSH release under acidic conditions. RSSH-derived symmetrical dialkyl polysulfide labeled as S3 and S4 ($R^1SS_nSR^1$, n=1 and 2), and unsymmetrical dialkyl polysulfide labeled as 'S2 and 'S3 ($R^1SS_nSR^3$, n=0 and 1) formation were observed. N-acetyl cystine and N-acetyl cysteine trisulfide are labeled as #$S_2$ and #$S_3$, respectively. 4-Hydroxyphenyl acetamide, labeled as asterisk, is used as internal standard in these experiments;

FIG. 24 shows UPLC-MS chromatograms of RSSH generation from 7b (100 μM) in the presence of glutathione (500 μM) incubated in pH 7.4 ammonium bicarbonate (50 mM) with DTPA (100 μM) at 37° C. for 45 min. The reaction mixture was quenched with 1% formic acid and analyzed by UPLC-MS. Under these conditions, 42±1 μM of 2b formation is observed. RSSH-derived symmetrical dialkyl polysulfide labeled as S3 and S4 ($R^1SS_nSR^1$, n=1-2), and unsymmetrical dialkyl polysulfide labeled as 'S2 to 'S4 ($R^1SS_nSR^3$, n=0-2) formation are observed. 4-Hydroxyphenyl acetamide, labeled as asterisk, is used as internal standard in these experiments;

FIG. 25 is a cell viability assay conducted on H9c2 cells with Precursor 7b (50, 100 and 150 μM) and byproduct 2b (150 μM) using SYTOX® Green nucleic acid stain. Results are expressed as the mean±SEM (n=5 for each treatment group) with 3 independent experiments. * P<0.0001 as compared to Triton X-100 control; and FIG. 26 shows results from H9c2 cardiac myoblasts pretreated with the RSSH precursor 7b (150 μM) and the COS precursor 8 (150 μM) for 2 h followed by exposure to $H_2O_2$ (200 μM) for 2 h. Quantification of cytotoxicity was carried out using SYTOX® Green nucleic acid stain. Results are expressed as the mean±SEM (n=5 for each treatment group) with five independent experiments. * P<0.001 for comparisons with the $H_2O_2$ treatment group; when 7b compared with the COS precursor 8, ** P<0.05.

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Alkylamine-Substituted Perthiocarbamates as Dual Precursors to Hydropersulfide and Carbonyl Sulfide

A. Representative Compounds of Formula (I)

In some embodiments, the presently disclosed subject matter provides a compound of formula (I):

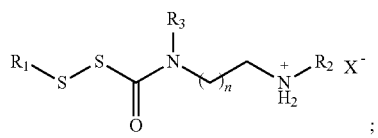

(I)

wherein: n is an integer selected from the group consisting of 0, 1, 2, 3, 4, 5, 6, 7, and 8, in some embodiments, n is selected from the group consisting of 1, 2, and 3; $R_1$ is selected from the group consisting of branched or unbranched alkyl, heterocycloalkyl, aryl, heteroaryl, a cysteine residue, a N-acetylcysteine residue, a homocysteine residue, a glutathione residue, and:

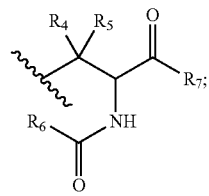

wherein: $R_4$ and $R_5$ are each independently selected from the group consisting of H, $C_1$-$C_4$ alkyl, and aryl; $R_6$ is $C_1$-$C_4$ alkyl or aryl; $R_7$ is —$OR_8$ or —$NR_9R_{10}$, wherein $R_8$, $R_9$, and $R_{10}$ are each independently selected from the group consisting of H, $C_1$-$C_4$ alkyl, and aryl; $R_2$ is selected from the group consisting of H, alkyl, aryl, and a functional group that responds to a stimulus selected from the group consisting of light, a redox reaction, and an enzymatic reaction; $R_3$ is selected from the group consisting of H, alkyl, and aryl; and $X^-$ is an anion.

In certain embodiments, the cysteine residue, the N-acetylcysteine residue, the homocysteine residue, and the glutathione residue are selected from the group consisting of:

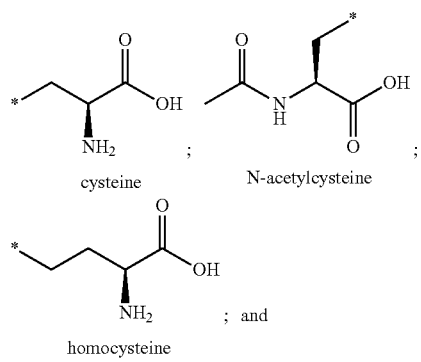

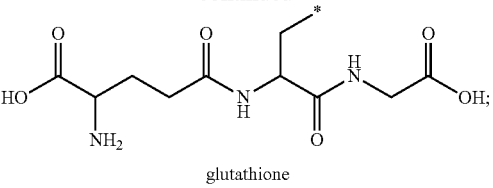

wherein each respective residue is bound to the compound of formula (I) through a thiol moiety, with the point of attachment designated by *. That is, the terminal sulfur atom on the compound of formula (I) is derived from cysteine, N-acetylcysteine, the homocysteine, and glutathione.

In some embodiments, the compound of formula (I) is:

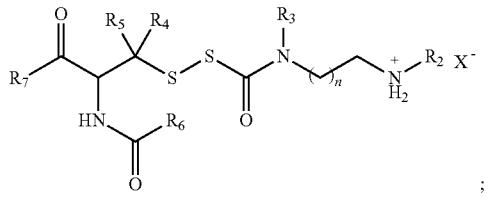

n is an integer selected from the group consisting of 1, 2, and 3; $R_4$ and $R_5$ are each independently H or $C_1$-$C_4$ alkyl; $R_6$ is $C_1$-$C_4$ alkyl or aryl; $R_7$ is —$OR_8$ or —$NR_9R_{10}$, wherein $R_8$, $R_9$, and $R_{10}$ are each independently selected from the group consisting of H, $C_1$-$C_4$ alkyl, and aryl; $R_2$ is selected from the group consisting of H, $C_1$-$C_4$ alkyl, and a functional group that responds to a stimulus selected from the group consisting of light, a redox reaction, and an enzymatic reaction; $R_3$ is selected from the group consisting of H, alkyl, and aryl; and $X^-$ is an anion. In particular embodiments, $R_3$ is $C_1$-$C_4$ alkyl, including $C_1$, $C_2$, $C_3$, and $C_4$ alkyl, such as methyl, ethyl, n-propyl, isopropyl (($CH_3$)$_2$CH—), n-butyl, iso-butyl (($CH_3$)$_2$—CH—$CH_2$—), sec-butyl ($CH_3$—$CH_2$—CH($CH_3$)—), and tert-butyl (($CH_3$)$_3$—C—). In yet more particular embodiments, $R_3$ is methyl.

In certain embodiments, the compound of formula (I) is:

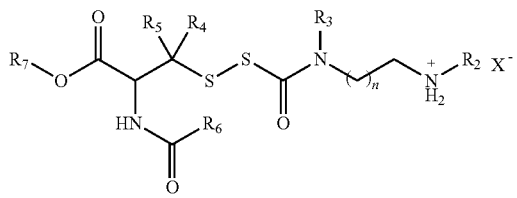

wherein: n is an integer selected from the group consisting of 1, 2, and 3; $R_4$ and $R_5$ are each independently H or $C_1$-$C_4$ alkyl; $R_6$ and $R_7$ are each independently $C_1$-$C_4$ alkyl; $R_2$ is selected from the group consisting of H, $C_1$-$C_4$ alkyl, and a functional group that responds to a stimulus selected from the group consisting of light, a redox reaction, and an enzymatic reaction; $R_3$ is selected from the group consisting of H, alkyl, and aryl; and $X^-$ is an anion.

In certain embodiments of the compound of formula (I), the functional group that responds to a stimulus selected from the group consisting of light, a redox reaction, and an enzymatic reaction is selected from the group consisting of:

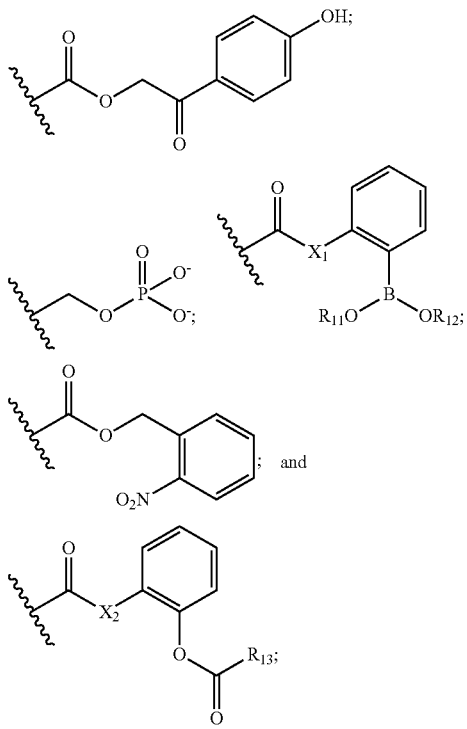

wherein:

X₁ and X₂ are each independently selected from the group consisting of O, $NR_{14}$, and $CR_{15}R_{16}$; wherein $R_{14}$, $R_{15}$, and $R_{16}$ are each independently H or branched or unbranched $C_1$-$C_4$ alkyl;

$R_{11}$ and $R_{12}$ are each independently selected from the group consisting of H, and branched or unbranched alkyl, or $R_{11}$ and $R_{12}$ together can form a cyclic alkyl or substituted cyclic alkyl; and $R_{13}$ is selected from the group consisting of branched or unbranched alkyl and aryl.

In certain embodiments, the borate ester exemplified by —B(OR₁₁)(OR₁₂) can be:

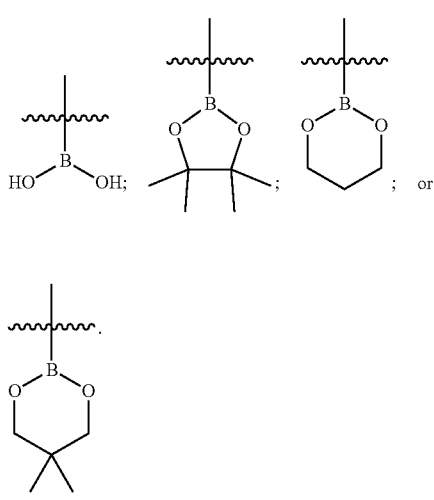

In particular embodiments, the compound of formula (I) is:

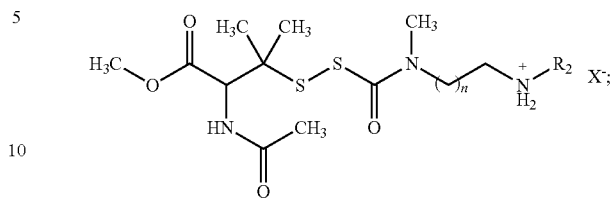

wherein: n is 1 or 2; and $R_2$ is H or $CH_3$.

In more particular embodiments, the compound of formula (I) is selected from the group consisting of:

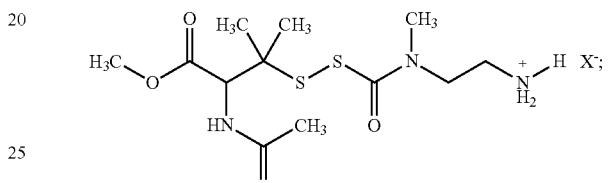

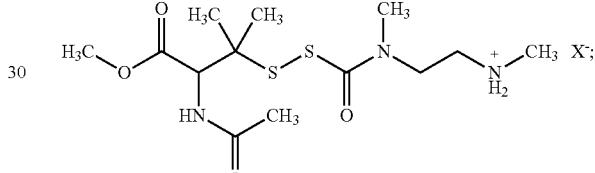

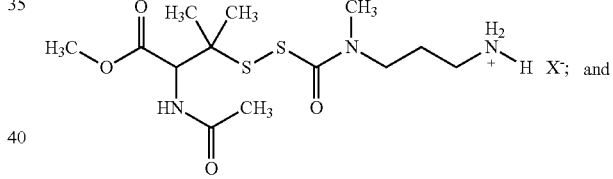

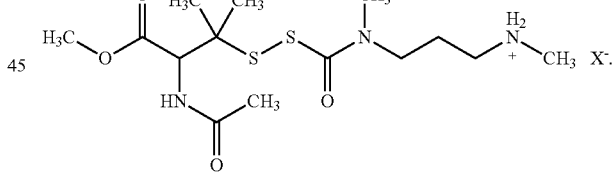

In certain embodiments, X⁻ is selected from the group consisting of chloride (Cl⁻), bromide (Br⁻), phosphate (($PO_4$)³⁻), trifluoroacetate ($CF_3COO^-$), acetate ($CH_3COO^-$), and benzoate ($C_6H_5COO^-$). In more certain aspects, the compound of formula (I) is selected from the group consisting of:

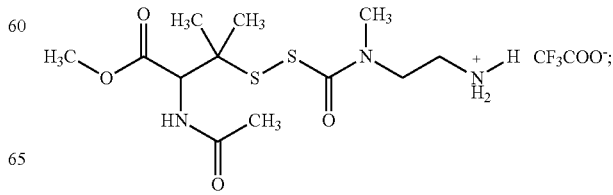

-continued

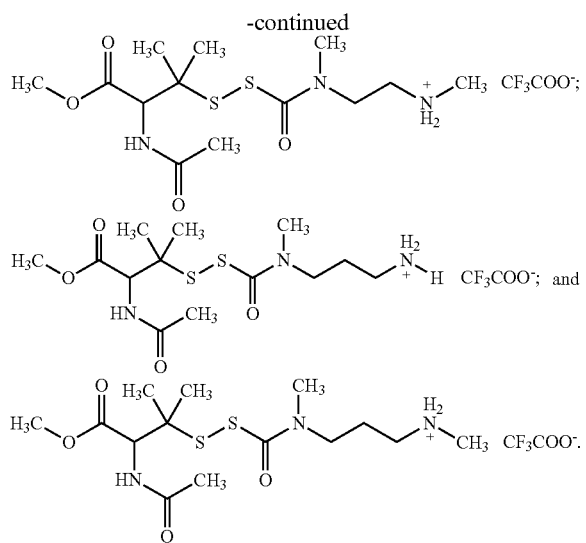

In some embodiments, the presently disclosed subject matter provides a pharmaceutical composition comprising a compound of formula (I) and a pharmaceutically acceptable carrier.

The presently disclosed subject matter further provides kits comprising one or more compounds of formula (I) as described herein. The kits may employ any of the compounds disclosed herein and instructions for use. The compound may be formulated in any acceptable form. The kits may be used for any one or more of the uses described herein, and, accordingly, may contain instructions for any one or more of the stated uses (e.g. treating and/or preventing and/or delaying the onset and/or ischemia/reperfusion injury).

Kits generally comprise suitable packaging. The kits may comprise one or more containers comprising any compound described herein. Each component (if there is more than one component) can be packaged in separate containers or some components can be combined in one container where cross-reactivity and shelf life permit.

The kits may optionally include a set of instructions, generally written instructions, although electronic storage media (e.g., magnetic diskette or optical disk) containing instructions also are acceptable, relating to the use of component(s) of the methods of the presently disclosed subject matter (e.g., treating, preventing and/or delaying the onset and/or the development of heart disease or ischemia/reperfusion injury). The instructions included with the kit generally include information as to the components and their administration to a subject.

B. Method for Treating a Disorder, Disease, or Condition Associated with Oxidative Stress, Including Ischemia/Reperfusion Injury In some embodiments, the presently disclosed subject matter provides a method for treating a disorder, disease, or condition associated with oxidative stress in a subject in need of treatment thereof, the method comprising administering to the subject a therapeutically effective amount of a compound of formula (I) or a pharmaceutical composition thereof.

Generally, oxidative stress is an imbalance between the systemic manifestation of reactive oxygen species and a biological system's ability to readily detoxify the reactive intermediates or to repair the resulting damage. Disturbances in the normal redox state of cells can cause toxic effects through the production of peroxides and free radicals that damage all components of the cell, including proteins, lipids, and DNA.

Several disorders, diseases, and conditions are associate with oxidative stress including, but not limited to, a mitochondrial disorder; an inherited mitochondrial disease; Alpers Disease; Barth syndrome; a Beta-oxidation Defect; Camitine-Acyl-Camitine Deficiency; Carnitine Deficiency; a Creatine Deficiency Syndrome; Co-Enzyme Q10 Deficiency; Complex I Deficiency; Complex II Deficiency; Complex III Deficiency; Complex IV Deficiency; Complex V Deficiency; COX Deficiency; chronic progressive external ophthalmoplegia (CPEO); CPT I Deficiency; CPT II Deficiency; Friedreich's Ataxia (FA); Glutaric Aciduria Type II; Keams-Sayre Syndrome (KSS); Lactic Acidosis; Long-Chain Acyl-CoA Dehydrogenase Deficiency (LCAD); LCHAD; Leigh Syndrome; Leigh-like Syndrome; Leber's Hereditary Optic Neuropathy (LHON); Lethal Infantile Cardiomyopathy (LIC); Luft Disease; Multiple Acyl-CoA Dehydrogenase Deficiency (MAD); Medium-Chain Acyl-CoA Dehydrogenase Deficiency (MCAD); Mitochondrial Myopathy, Encephalopathy, Lactacidosis, Stroke (MELAS); Myoclonic Epilepsy with Ragged Red Fibers (MERRF); Mitochondrial Recessive Ataxia Syndrome (MIRAS); Mitochondrial Cytopathy, Mitochondrial DNA Depletion; Mitochondrial Encephalopathy; Mitochondrial Myopathy; Myoneurogastrointestinal Disorder and Encephalopathy (MNGIE); Neuropathy, Ataxia, and Retinitis Pigmentosa (NARP); Pearson Syndrome; Pyruvate Carboxylase Deficiency; Pyruvate Dehydrogenase Deficiency; a POLG Mutation; a Respiratory Chain Disorder; Short-Chain Acyl-CoA Dehydrogenase Deficiency (SCAD); SCHAD; Very Long-Chain Acyl-CoA Dehydrogenase Deficiency (VLCAD); a myopathy; cardiomyopathy; encephalomyopathy; Parkinson's disease; amyotrophic lateral sclerosis (ALS); a motor neuron disease; epilepsy; macular degeneration; metabolic syndrome; brain cancer; Huntington's Disease; a mood disorder; schizophrenia; bipolar disorder; a pervasive developmental disorder; autistic disorder; Asperger's syndrome; childhood disintegrative disorder (CDD); Rett's disorder; PDD-not otherwise specified (PDD-NOS); a cerebrovascular accident; stroke; a vision impairment; optic neuropathy; dominant inherited juvenile optic atrophy; optic neuropathy caused by a toxic agent; glaucoma; Stargardt's macular dystrophy; diabetic retinopathy; diabetic maculopathy; retinopathy of prematurity; ischemic reperfusion-related retinal injury; oxygen poisoning; a haemoglobinopathy; thalassemia; sickle cell anemia; seizures; ischemia; renal tubular acidosis; attention deficit/hyperactivity disorder (ADHD); a neurodegenerative disorder resulting in hearing or balance impairment; Dominant Optic Atrophy (DOA); Maternally inherited diabetes and deafness (MIDD); chronic fatigue; contrast-induced kidney damage; contrast-induced retinopathy damage; Abetalipoproteinemia; retinitis pigmentosum; Wolfram's disease; Tourette syndrome; cobalamin c defect; methylmalonic aciduria; glioblastoma; Down's syndrome; acute tubular necrosis; a muscular dystrophy; a leukodystrophy; Progressive Supranuclear Palsy; spinal muscular atrophy; hearing loss; noise induced hearing loss; traumatic brain injury; Juvenile Huntington's Disease; Multiple Sclerosis; NGLY1; Multisystem atrophy; Adrenoleukodystrophy; and Adrenomyeloneuropathy.

In particular embodiments, the disorder, disease, or condition associated with oxidative stress comprises ischemia/reperfusion injury. Accordingly, in some embodiments, the presently disclosed compounds of formula (I) are cardioprotective, for example, against ischemia/reperfusion injury, including myocardial ischemia/reperfusion injury. In certain embodiments, the treating comprises preventing, reducing the occurrence of or severity of, or protecting against ischemia/reperfusion injury.

Ischemia is a condition characterized by an interruption or inadequate supply of blood to a cell, tissue, or organ, which causes oxygen deprivation in the affected cell, tissue, or organ. Accordingly, as used herein the term "ischemic injury," or derivations thereof, refers to an injury to a cell, tissue, and/or organ caused by ischemia, i.e., a reduction or insufficient supply of blood (and therefore oxygen) to a cell, tissue, and/or organ, e.g., due to a blocked artery and the like, resulting in damage or dysfunction of the cell, tissue, and/or organ.

Representative ischemic injuries include, but are not limited to, injuries caused by cardiovascular ischemia, cerebrovascular ischemia, renal ischemia, hepatic ischemia, ischemic cardiomyopathy, cutaneous ischemia, bowel ischemia, intestinal ischemia, gastric ischemia, pulmonary ischemia, pancreatic ischemia, skeletal muscle ischemia, abdominal muscle ischemia, limb ischemia, ischemic colitis, mesenteric ischemia, and silent ischemia. An ischemic injury can affect, for example, a heart, kidney, liver, brain, muscle, intestine, stomach, lung, and/or skin.

In a particular embodiment, the ischemic injury is the result of a myocardial ischemia. Myocardial ischemia is a condition caused by a blockage or constriction of one or more of the coronary arteries, such as can occur with atherosclerotic plaque occlusion or rupture. The blockade or constriction causes oxygen deprivation of the non-perfused tissue, which can cause tissue damage. An injury resulting from a myocardial ischemia can result from, for example, a myocardial infarction (e.g., an acute myocardial infarction) in a subject. In another embodiment, the ischemic injury is an injury resulting from cerebral ischemia (e.g., a stroke) in a subject.

Upon reperfusion with subsequent reoxygenation of the cell, tissue, or organ, i.e., when blood is able to flow again or the oxygen demand of the cell, tissue, or organ subsides, additional injury can be caused by oxidative stress. As used herein, the term "ischemia-reperfusion injury" refers to an injury resulting from the restoration of blood flow to an area of a cell, tissue, and/or organ that had previously experienced deficient blood flow due to an ischemic event. Oxidative stresses associated with reperfusion may cause damage to the affected cells, tissues, and/or organs. Ischemia-reperfusion injury is characterized biochemically by a depletion of oxygen during an ischemic event followed by reoxygenation and the concomitant generation of reactive oxygen species during reperfusion.

An ischemia-reperfusion injury can be caused, for example, by a natural event (e.g., restoration of blood flow following a myocardial infarction), a trauma, or by one or more surgical procedures or other therapeutic interventions that restore blood flow to a cell, tissue, and/or organ that has been subjected to a diminished supply of blood. Such surgical procedures include, for example, coronary artery bypass graft surgery, coronary angioplasty, organ transplant surgery and the like. The effects of ischemia/reperfusion injury can be fatal, particularly when the injury occurs in a critical organ, such as the heart or brain.

Accordingly, in some embodiments, the presently disclosed subject matter provides a method for treating, preventing, reducing, or protecting against ischemia/reperfusion injury in a subject who is afflicted with or is at risk of an ischemia/reperfusion injury or an ischemic event. Thus, provided herein is a method of treating, preventing, reducing, or protecting against injury associated with ischemia/reperfusion by administering to a subject in need of treatment thereof, an therapeutically effective amount of at least one compound of formula (I).

In some embodiments, a compound of formula (I) is administered to the subject prior to the onset of ischemia. Presently disclosed compounds of formula (I) can thus be used in methods of preventing or reducing injury associated with future ischemia/reperfusion. For example, administration of a compound of formula (I) prior to the onset of ischemia may reduce tissue necrosis (the size of infarct) in at-risk tissues.

In some embodiments, a compound of formula (I) is administered to the subject after ischemia. In some embodiments, a compound of formula (I) is administered to the subject after ischemia, but before reperfusion. In other embodiments, a compound of formula (I) is administered to the subject after ischemia/reperfusion, where the administration protects against further injury. In some embodiments, a compound of formula (I) is administered to a subject thought to be or is demonstrated to be at risk for an ischemic event. In some embodiments, a compound of formula (I) is administered to or contacted with an organ that is to be transplanted in an amount effective to reduce ischemia/reperfusion injury to the organ upon reperfusion in the recipient of the transplanted organ.

For the treatment of ischemic and ischemia-reperfusion injuries caused by therapeutic interventions, such as surgical procedures, it is preferable that a compound of formula (I) be administered to a subject undergoing treatment prior to the therapeutic intervention (e.g., cardiac surgery, organ transplant). For example, a compound of formula (I) can be administered to a subject undergoing treatment, e.g., about 5 minutes, about 10 minutes, about 15 minutes, about 20 minutes, about 30 minutes or about 45 minutes, about 1 hour, about 2 hours, about 3 hours, about 4 hours, about 5 hours, about 12 hours, about 24 hours, or about 48 hours prior to the therapeutic intervention.

Alternatively, or in addition, a compound of formula (I) can be administered to a subject undergoing treatment at the time of, or during, the therapeutic intervention. For example, the compound can be administered one or more times during the course of a therapeutic intervention in intervals (e.g., 15 minute intervals). Alternatively, a compound of formula (I) can be administered continuously throughout the duration of a therapeutic intervention.

Furthermore, a compound of formula (I) can be administered to a subject undergoing treatment after a therapeutic intervention. For example, a compound of formula (I) can be administered to a subject undergoing treatment, e.g., about 5 minutes, about 10 minutes, about 15 minutes, about 20 minutes, about 30 minutes or about 45 minutes, about 1 hour, about 2 hours, about 3 hours, about 4 hours, about 5 hours, about 12 hours, about 24 hours, or about 48 hours after the therapeutic intervention.

A compound of formula (I) also can be used to prevent, inhibit, or reduce the occurrence of an ischemia or ischemia-reperfusion injury to a cell, tissue, and/or organ, ex vivo, prior to a therapeutic intervention (e.g., a tissue employed in a graft procedure, an organ employed in an organ transplant surgery). For example, prior to transplant of an organ into a host individual (e.g., during storage or transport of the organ in a sterile environment), the organ can be contacted with a compound of formula (I) to prevent, inhibit, or reduce the occurrence of an ischemia or ischemia-reperfusion injury.

As described herein, conditions resulting from ischemia, and injuries caused by ischemia or ischemia-reperfusion, can induce apoptotic cell death in an affected cell, tissue, and/or organ, leading to damage and dysfunction. Accordingly, the compounds of the invention also have utility in methods of inhibiting apoptosis in a cell, a tissue, and/or an organ (e.g., a transplant tissue or organ or a cell, tissue or organ in a subject), wherein the cell, tissue or organ has experienced an ischemia or other condition or disorder that results in excessive or unwanted apoptosis. The methods comprise contacting the cells, tissue, and/or organ with, or administering to the subject, an effective amount of a compound of formula (I).

Subjects can be selected for treatment who are at risk of a first or subsequent ischemic event. For example, such subjects include, but are not limited to, those with known hypercholesterolemia, EKG changes associated with risk of ischemia, sedentary lifestyle, angiographic evidence of partial coronary artery obstruction, echocardiographic evidence of myocardial damage, or any other evidence of a risk for a future or additional ischemic event (for example a myocardial ischemic event, such as a myocardial infarction (MI), or a neurovascular ischemia, such as a cerebrovascular accident (CVA)). In some embodiments, subjects are selected for treatment who are at risk of future ischemia, but who have no present evidence of ischemia, such as electrocardiographic changes associated with ischemia (for example, peaked or inverted T-waves or ST segment elevations or depression in an appropriate clinical context), elevated CKMB or clinical evidence of ischemia, including crushing substernal chest pain or arm pain, shortness of breath and/or diaphoresis.

Compounds of formula (I) also can be administered prior to procedures in which myocardial ischemia is at risk of occurring, for example an angioplasty or other surgeries, such as coronary artery bypass graft surgery. In other embodiments, a compound of formula (I) can be administered to a subject at demonstrated risk for an ischemic event. The selection of a subject with such a status can be performed by a variety of methods, some of which are noted hereinabove. For example, a subject with one of more of an abnormal EKG not associated with active ischemia, prior history of myocardial infarction, elevated serum cholesterol, and the like, would be at risk for an ischemic event. Thus, an at-risk subject could be selected by physical testing or eliciting the potential subject's medical history to determine whether the subject has any indications of risk for an ischemic event. If risk is demonstrated based on the indications discussed above, or any other indications that one skilled in the art would appreciate, then the subject would be considered at demonstrated risk for an ischemic event.

Ischemia/reperfusion may damage tissues other than those of the myocardium and the presently disclosed subject matter includes methods for treating or preventing such damage. In one variation, the method finds use in reducing injury from ischemia/reperfusion in the tissue of the brain, liver, gut, kidney, bowel, or in any other tissue.

Selecting a person at risk for non-myocardial ischemia could include a determination of the indicators used to assess risk for myocardial ischemia. Other factors, however, may indicate a risk for ischemia/reperfusion in other tissues. For example, surgery patients often experience surgery-related ischemia. Thus, subjects scheduled for surgery could be considered at risk for an ischemic event. The following risk factors for stroke (or a subset of these risk factors) would demonstrate a subject's risk for ischemia of brain tissue: hypertension cigarette smoking, carotid artery stenosis, physical inactivity, diabetes mellitus, hyperlipidemia, transient ischemic attack, atrial fibrillation, coronary artery disease, congestive heart failure, past myocardial infarction, left ventricular dysfunction with mural thrombus, and mitral stenosis. Further, complications of untreated infectious diarrhea in the elderly can include myocardial, renal, cerebrovascular and intestinal ischemia. Alternatively, subjects could be selected based on risk factors for ischemic bowel, kidney or liver disease. For example, treatment would be initiated in elderly subjects at risk of hypotensive episodes, such as surgical blood loss. Thus, subjects presenting with such an indication would be considered at risk for an ischemic event. Also included is a method of administering a compound of formula (I) to a subject who has any one or more of the conditions listed herein, such as diabetes mellitus or hypertension. Other conditions that may result in ischemia, such as cerebral arteriovenous malformation would be considered to demonstrate risk for an ischemic event.

The method of administering a compound of formula (I) to an organ to be transplanted includes administration of a compound of formula (I) prior to removal of the organ from the donor, for example through the perfusion cannulas used in the organ removal process. If the organ donor is a live donor, for example a kidney donor, the compound of formula (I) can be administered to the organ donor as described above for a subject at risk for an ischemic event. In other cases the compound of formula (I) can be administered by storing the organ in a solution comprising compound of formula (I). For example, the compound of formula (I) can be included in the organ preservation solution, such as University of Wisconsin "UW" solution, which is a solution comprising hydroxyethyl starch substantially free of ethylene glycol, ethylene chlorohydrin, and acetone (see U.S. Pat. No. 4,798,824). Where an organ or tissue is accessible because of removal from the patient, such organ or tissue may be bathed in a medium containing the subject compositions, the subject compositions may be painted onto the organ, or may be applied in any convenient way. The methods of the presently disclosed subject matter embrace administration of the compounds to an organ to be donated (such as to prevent ischemia/reperfusion injury). Accordingly, organs that are removed from one subject for transplant into another subject may be bathed in a medium containing or otherwise exposed to a compound or composition as described herein.

As used herein, the term "treating" can include reversing, alleviating, inhibiting the progression of, preventing or reducing the likelihood of the disease, disorder, or condition to which such term applies, or one or more symptoms or manifestations of such disease, disorder or condition. Preventing refers to causing a disease, disorder, condition, or symptom or manifestation of such, or worsening of the severity of such, not to occur. Accordingly, the presently disclosed compounds can be administered prophylactically to prevent or reduce the incidence or recurrence of the disease, disorder, or condition.

The "subject" treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein. The term "subject" also refers to an organism, tissue, cell, or collection of cells from a subject.

In general, the "effective amount" of an active agent or drug delivery device refers to the amount necessary to elicit the desired biological response. As will be appreciated by those of ordinary skill in this art, the effective amount of an agent or device may vary depending on such factors as the desired biological endpoint, the agent to be delivered, the makeup of the pharmaceutical composition, the target tissue, and the like.

In other embodiments, the presently disclosed subject matter included administering a compound of formula (I) in combination with one or more therapeutic agents. In certain embodiments, the presently disclosed method of treatment further comprises administering to the subject one or more compounds of formula (I) in combination with one or more other therapeutic agents designed to minimize or mitigate ischemic injury. In particular embodiments, the one or more other therapeutic agents is selected from the group consisting of an angiotensin T-converting enzyme (ACE) inhibitor, an alpha-adrenergic blocker, a central adrenergic inhibitor, a beta-adrenergic blocker, an angiotensin II receptor blocker, a calcium channel blocker, a vasodilator, a phosphodiesterase (PDE) inhibitor, an HMG-CoA reductase inhibitor, a cholesterol-lowering agent, an antiarrhythmic agent, a digitalis drug, a nitrate, a diuretic, an anticoagulant, an anti-platelet agent, a thrombolytic agent, an antioxidant, and combinations thereof, including other agents or medical interventions for protecting the myocardium in subject afflicted with coronary artery disease.

The term "combination" is used in its broadest sense and means that a subject is administered at least two agents, more particularly a compound of formula (I) and at least one more other therapeutic agents. More particularly, the term "in combination" refers to the concomitant administration of two (or more) active agents for the treatment of a, e.g., single disease state. As used herein, the active agents may be combined and administered in a single dosage form, may be administered as separate dosage forms at the same time, or may be administered as separate dosage forms that are administered alternately or sequentially on the same or separate days. In one embodiment of the presently disclosed subject matter, the active agents are combined and administered in a single dosage form. In another embodiment, the active agents are administered in separate dosage forms (e.g., wherein it is desirable to vary the amount of one but not the other). The single dosage form may include additional active agents for the treatment of the disease state.

Further, the compounds of formula (I) described herein can be administered alone or in combination with adjuvants that enhance stability of the compounds of formula (I), alone or in combination with one or more therapeutic agents, facilitate administration of pharmaceutical compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies.

The timing of administration of a compound of formula (I) and at least one additional therapeutic agent can be varied so long as the beneficial effects of the combination of these agents are achieved. Accordingly, the phrase "in combination with" refers to the administration of a compound of formula (I) and at least one additional therapeutic agent either simultaneously, sequentially, or a combination thereof. Therefore, a subject administered a combination of a compound of formula (I) and at least one additional therapeutic agent can receive compound of formula (I) and at least one additional therapeutic agent at the same time (i.e., simultaneously) or at different times (i.e., sequentially, in either order, on the same day or on different days), so long as the effect of the combination of both agents is achieved in the subject.

When administered sequentially, the agents can be administered within 1, 5, 10, 30, 60, 120, 180, 240 minutes or longer of one another. In other embodiments, agents administered sequentially, can be administered within 1, 5, 10, 15, 20 or more days of one another. Where the compound of formula (I) and at least one additional therapeutic agent are administered simultaneously, they can be administered to the subject as separate pharmaceutical compositions, each comprising either a compound of formula (I) or at least one additional therapeutic agent, or they can be administered to a subject as a single pharmaceutical composition comprising both agents.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times.

In some embodiments, when administered in combination, the two or more agents can have a synergistic effect. As used herein, the terms "synergy," "synergistic," "synergistically" and derivations thereof, such as in a "synergistic effect" or a "synergistic combination" or a "synergistic composition" refer to circumstances under which the biological activity of a combination of a compound of formula (I) and at least one additional therapeutic agent is greater than the sum of the biological activities of the respective agents when administered individually.

Synergy can be expressed in terms of a "Synergy Index (SI)," which generally can be determined by the method described by F. C. Kull et al., Applied Microbiology 9, 538 (1961), from the ratio determined by:

$$Q_a/Q_A + Q_b/Q_B = \text{Synergy Index (SI)}$$

wherein:

$Q_A$ is the concentration of a component A, acting alone, which produced an end point in relation to component A;

$Q_a$ is the concentration of component A, in a mixture, which produced an end point;

$Q_B$ is the concentration of a component B, acting alone, which produced an end point in relation to component B; and $Q_b$ is the concentration of component B, in a mixture, which produced an end point.

Generally, when the sum of $Q_a/Q_A$ and $Q_b/Q_B$ is greater than one, antagonism is indicated. When the sum is equal to one, additivity is indicated. When the sum is less than one, synergism is demonstrated. The lower the SI, the greater the synergy shown by that particular mixture. Thus, a "synergistic combination" has an activity higher that what can be expected based on the observed activities of the individual components when used alone. Further, a "synergistically effective amount" of a component refers to the amount of the component necessary to elicit a synergistic effect in, for example, another therapeutic agent present in the composition.

As used herein, the term "inhibit," and grammatical derivations thereof, refers to the ability of a presently disclosed compound, e.g., a presently disclosed compound of formula (I), to block, partially block, interfere, decrease, or reduce the growth of bacteria or a bacterial infection. Thus, one of ordinary skill in the art would appreciate that the term "inhibit" encompasses a complete and/or partial decrease in the growth of bacteria or a bacterial infection, e.g., a decrease by at least 10%, in some embodiments, a decrease by at least 20%, 30%, 50%, 75%, 95%, 98%, and up to and including 100%.

C. Pharmaceutical Compositions and Administration

In another aspect, the present disclosure provides a pharmaceutical composition including one compound of formula (I) alone or in combination with one or more additional therapeutic agents in admixture with a pharmaceutically acceptable excipient. One of skill in the art will recognize that the pharmaceutical compositions include the pharmaceutically acceptable salts of the compounds described above. Pharmaceutically acceptable salts are generally well known to those of ordinary skill in the art, and include salts of active compounds which are prepared with relatively nontoxic acids or bases, depending on the particular substituent moieties found on the compounds described herein. When compounds of the present disclosure contain relatively acidic functionalities, base addition salts can be obtained by contacting the neutral form of such compounds with a sufficient amount of the desired base, either neat or in a suitable inert solvent or by ion exchange, whereby one basic counterion (base) in an ionic complex is substituted for another. Examples of pharmaceutically acceptable base addition salts include sodium, potassium, calcium, ammonium, organic amino, or magnesium salt, or a similar salt.

When compounds of the present disclosure contain relatively basic functionalities, acid addition salts can be obtained by contacting the neutral form of such compounds with a sufficient amount of the desired acid, either neat or in a suitable inert solvent or by ion exchange, whereby one acidic counterion (acid) in an ionic complex is substituted for another. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-toluenesulfonic, citric, tartaric, methanesulfonic, and the like. Also included are salts of amino acids such as arginate and the like, and salts of organic acids like glucuronic or galactunoric acids and the like (see, for example, Berge et al, "Pharmaceutical Salts", Journal of Pharmaceutical Science, 1977, 66, 1-19). Certain specific compounds of the present disclosure contain both basic and acidic functionalities that allow the compounds to be converted into either base or acid addition salts.

Accordingly, pharmaceutically acceptable salts suitable for use with the presently disclosed subject matter include, by way of example but not limitation, acetate, benzenesulfonate, benzoate, bicarbonate, bitartrate, bromide, calcium edetate, camsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy ($20^{th}$ ed.) Lippincott, Williams & Wilkins (2000).

In therapeutic and/or diagnostic applications, the compounds of the disclosure can be formulated for a variety of modes of administration, including systemic and topical or localized administration. Techniques and formulations generally may be found in Remington: The Science and Practice of Pharmacy ($20^{th}$ ed.) Lippincott, Williams & Wilkins (2000).

Depending on the specific conditions being treated, such agents may be formulated into liquid or solid dosage forms and administered systemically or locally. The agents may be delivered, for example, in a timed- or sustained-slow release form as is known to those skilled in the art. Techniques for formulation and administration may be found in Remington: The Science and Practice of Pharmacy ($20^{th}$ ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articular, intra-sternal, intra-synovial, intra-hepatic, intralesional, intracranial, intraperitoneal, intranasal, or intraocular injections or other modes of delivery.

For injection, the agents of the disclosure may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure also may be formulated by methods known to those of skill in the art, and may include, for example, but not limited to, examples of solubilizing, diluting, or dispersing substances, such as saline; preservatives, such as benzyl alcohol; absorption promoters; and fluorocarbons.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein. Generally, the compounds according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A non-limiting dosage is 10 to 30 mg per day. The exact dosage will depend upon the route of administration, the form in which the compound is administered, the subject to be treated, the body weight of the subject to be treated, the bioavailability of the compound(s), the adsorption, distribution, metabolism, and excretion (ADME) toxicity of the compound(s), and the preference and experience of the attending physician.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

D. Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to compounds of formula (I) are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group on a molecule, provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted at one or more positions).

Where substituent groups or linking groups are specified by their conventional chemical formulae, written from left to right, they equally encompass the chemically identical substituents that would result from writing the structure from right to left, e.g., —$CH_2O$— is equivalent to —$OCH_2$—; —C(=O)O— is equivalent to —OC(=O)—; —OC(=O)NR— is equivalent to —NRC(=O)O—, and the like.

When the term "independently selected" is used, the substituents being referred to (e.g., R groups, such as groups $R_1$, $R_2$, and the like, or variables, such as "m" and "n"), can be identical or different. For example, both $R_1$ and $R_2$ can be substituted alkyls, or $R_1$ can be hydrogen and $R_2$ can be a substituted alkyl, and the like.

The terms "a," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Unless otherwise explicitly defined, a "substituent group," as used herein, includes a functional group selected from one or more of the following moieties, which are defined herein:

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, isopropyl, cyclopropyl, allyl, vinyl, n-butyl, tert-butyl, ethynyl, cyclohexyl, and the like.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., $C_{1-10}$ means one to ten carbons, including 1, 2, 3, 4, 5, 6, 7, 8, 9, and 10 carbons). In particular embodiments, the term "alkyl" refers to $C_{1-20}$ inclusive, including 1, 2, 3, 4, 5, 6, 7, 8, 9, 10, 11, 12, 13, 14, 15, 16, 17, 18, 19, and 20 carbons, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, isopentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, cyano, and mercapto.

The term "heteroalkyl," by itself or in combination with another term, means, unless otherwise stated, a stable straight or branched chain having from 1 to 20 carbon atoms or heteroatoms or a cyclic hydrocarbon group having from 3 to 10 carbon atoms or heteroatoms, or combinations thereof, consisting of at least one carbon atom and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$—S(O)—CH$_3$, —CH$_2$—CH$_2$—S(O)$_2$—CH$_3$, —CH═CH—O—CH$_3$, —Si(CH$_3$)$_3$, —CH$_2$—CH═N—OCH$_3$, —CH═CH—N(CH$_3$)—CH$_3$, O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$.

As described above, heteroalkyl groups, as used herein, include those groups that are attached to the remainder of the molecule through a heteroatom, such as —C(O)NR', —NR'R", —OR', —SR, —S(O)R, and/or —S(O$_2$)R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, unsubstituted alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl, and fused ring systems, such as dihydro- and tetrahydronaphthalene, and the like.

The term "cycloalkylalkyl," as used herein, refers to a cycloalkyl group as defined hereinabove, which is attached to the parent molecular moiety through an alkylene moiety, also as defined above, e.g., a $C_{1-20}$ alkylene moiety. Examples of cycloalkylalkyl groups include cyclopropylmethyl and cyclopentylethyl.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of nitrogen (N), oxygen (O), sulfur (S), phosphorus (P), and silicon (Si), and optionally can include one or more double bonds.

The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidinyl, piperazinyl, indolinyl, quinuclidinyl, morpholinyl, thiomorpholinyl, thiadiazinanyl, tetrahydrofuranyl, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

An unsaturated hydrocarbon has one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl."

More particularly, the term "alkenyl" as used herein refers to a monovalent group derived from a $C_{2-20}$ inclusive straight or branched hydrocarbon moiety having at least one carbon-carbon double bond by the removal of a single hydrogen molecule. Alkenyl groups include, for example, ethenyl (i.e., vinyl), propenyl, butenyl, 1-methyl-2-buten-1-yl, pentenyl, hexenyl, octenyl, allenyl, and butadienyl.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched $C_{2-20}$ hydrocarbon of a designed number of carbon atoms containing at least one carbon-carbon triple bond. Examples of "alkynyl" include ethynyl, 2-propynyl (propargyl), 1-propynyl, pentynyl, hexynyl, and heptynyl groups, and the like.

The term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—CH$_2$—); ethylene (—CH$_2$—CH$_2$—); propylene (—(CH$_2$)$_3$—); cyclohexylene (—C$_6$H$_{10}$—); —CH═CH—CH═CH—; —CH═CH—CH$_2$—; —CH$_2$CH$_2$CH$_2$CH$_2$—, —CH$_2$CH═CHCH$_2$—, —CH$_2$CsCCH$_2$—, —CH$_2$CH$_2$CH (CH$_2$CH$_2$CH$_3$)CH$_2$—, —(CH$_2$)$_q$—N(R)—(CH$_2$)$_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—CH$_2$—O—); and ethylenedioxyl (—O—(CH$_2$)$_2$—O—). An alkylene group can have about 2 to about 3 carbon atoms and can further have 6-20 carbons. Typically, an alkyl (or alkylene) group will have from 1 to 24 carbon atoms, with those groups having 10 or fewer carbon atoms being some embodiments of the present disclosure. A "lower alkyl" or "lower alkylene" is a shorter chain alkyl or alkylene group, generally having eight or fewer carbon atoms.

The term "heteroalkylene" by itself or as part of another substituent means a divalent group derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms also can occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—.

The term "aryl" means, unless otherwise stated, an aromatic hydrocarbon substituent that can be a single ring or multiple rings (such as from 1 to 3 rings), which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent forms of aryl and heteroaryl, respectively.

For brevity, the term "aryl" when used in combination with other terms (e.g., aryloxy, arylthioxy, arylalkyl) includes both aryl and heteroaryl rings as defined above.

Thus, the terms "arylalkyl" and "heteroarylalkyl" are meant to include those groups in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g. "3 to 7 membered"), the term "member" refers to a carbon or heteroatom.

Further, a structure represented generally by the formula:

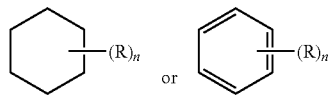

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

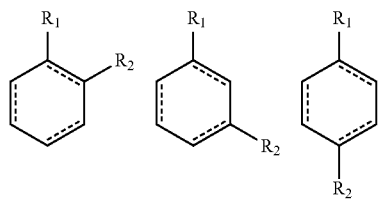

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

The symbol ( ⌇⌇⌇ ) denotes the point of attachment of a moiety to the remainder of the molecule.

When a named atom of an aromatic ring or a heterocyclic aromatic ring is defined as being "absent," the named atom is replaced by a direct bond.

Each of above terms (e.g., "alkyl," "heteroalkyl," "cycloalkyl, and "heterocycloalkyl", "aryl," "heteroaryl," "phosphonate," and "sulfonate" as well as their divalent derivatives) are meant to include both substituted and unsubstituted forms of the indicated group. Optional substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R")=NR'", —S(O)R', —S(O)$_2$R', —S(O)$_2$NR'R", —NRSO$_2$R', —CN, CF$_3$, fluorinated C$_{1-4}$ alkyl, and —NO$_2$ in a number ranging from zero to (2m'+1), where m' is the total number of carbon atoms in such groups. R', R", R'" and R"" each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen. When a compound of the disclosure includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for alkyl groups above, exemplary substituents for aryl and heteroaryl groups (as well as their divalent derivatives) are varied and are selected from, for example: halogen, —OR', —NR'R", —SR', —SiR'R"R'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R"R'")=NR"", —NR—C(NR'R")=NR'"—S(O)R', —S(O)$_2$R', —S(O)$_2$NR'R", —NRSO$_2$R', —CN and —NO$_2$, —R', —N$_3$, —CH(Ph)$_2$, fluoro(C$_{1-4}$)alkoxo, and fluoro(C$_{1-4}$)alkyl, in a number ranging from zero to the total number of open valences on aromatic ring system; and where R', R", R'" and R"" may be independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R'" and R"" groups when more than one of these groups is present.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4.

One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R''')$_d$—, where s and d are independently integers of from 0 to 3, and X' is —O—, —NR'—, —S—, —S(O)—, —S(O)$_2$—, or —S(O)$_2$NR'—. The substituents R, R', R" and R'" may be independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "acyl" refers to an organic acid group wherein the —OH of the carboxyl group has been replaced with another substituent and has the general formula RC(=O)—, wherein R is an alkyl, alkenyl, alkynyl, aryl, carbocylic, heterocyclic, or aromatic heterocyclic group as defined herein). As such, the term "acyl" specifically includes arylacyl groups, such as a 2-(furan-2-yl) acetyl)- and a 2-phenylacetyl group. Specific examples of acyl groups include acetyl and benzoyl. Acyl groups also are intended to include amides, —RC(=O)NR', esters, —RC(=O)OR', ketones, —RC(=O)R', and aldehydes, —RC(=O)H.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include C$_{1-20}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, tert-butoxyl, and n-pentoxyl, neopentoxyl, n-hexoxyl, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl, i.e., C$_6$H$_5$—CH$_2$—O—. An aralkyloxyl group can optionally be substituted.

"Alkoxycarbonyl" refers to an alkyl-O—C(=O)— group. Exemplary alkoxycarbonyl groups include methoxy-carbonyl, ethoxycarbonyl, butyloxycarbonyl, and tert-butyloxycarbonyl.

"Aryloxycarbonyl" refers to an aryl-O—C(=O)— group. Exemplary aryloxycarbonyl groups include phenoxy- and naphthoxy-carbonyl.

"Aralkoxycarbonyl" refers to an aralkyl-O—C(=O)— group. An exemplary aralkoxycarbonyl group is benzyloxycarbonyl.

"Carbamoyl" refers to an amide group of the formula —C(=O)NH$_2$. "Alkylcarbamoyl" refers to a R'RN—C(=O)— group wherein one of R and R' is hydrogen and the other of R and R' is alkyl and/or substituted alkyl as previously described. "Dialkylcarbamoyl" refers to a R'RN—C(=O)— group wherein each of R and R' is independently alkyl and/or substituted alkyl as previously described.

The term carbonyldioxyl, as used herein, refers to a carbonate group of the formula —O—C(=O)—OR.

"Acyloxyl" refers to an acyl-O— group wherein acyl is as previously described. The term "amino" refers to the —NH$_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R", wherein R' and R" are each independently selected from the group consisting of alkyl groups. The term trialkylamino refers to a group having the structure —NR'R"R'", wherein R', R", and R'" are each independently selected from the group consisting of alkyl groups. Additionally, R', R", and/or R'" taken together may optionally be —(CH$_2$)$_k$— where k is an integer from 2 to 6. Examples include, but are not limited to, methylamino, dimethylamino, ethylamino, diethylamino, diethylaminocarbonyl, methylethylamino, isopropylamino, piperidino, trimethylamino, and propylamino.

The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —C(=O)— group, and can include an aldehyde group represented by the general formula R—C(=O)H.

The term "carboxyl" refers to the —COOH group. Such groups also are referred to herein as a "carboxylic acid" moiety.

The term "cyano" refers to the —C≡N group.

The terms "halo," "halide," or "halogen" as used herein refer to fluoro, chloro, bromo, and iodo groups. Additionally, terms such as "haloalkyl," are meant to include monohaloalkyl and polyhaloalkyl. For example, the term "halo(C$_{1-4}$)alkyl" is mean to include, but not be limited to, trifluoromethyl, 2,2,2-trifluoroethyl, 4-chlorobutyl, 3-bromopropyl, and the like.

The term "hydroxyl" refers to the —OH group.

The term "hydroxyalkyl" refers to an alkyl group substituted with an —OH group.

The term "mercapto" refers to the —SH group.

The term "oxo" as used herein means an oxygen atom that is double bonded to a carbon atom or to another element.

The term "nitro" refers to the —NO$_2$ group.

The term "thio" refers to a compound described previously herein wherein a carbon or oxygen atom is replaced by a sulfur atom.

The term "sulfate" refers to the —SO$_4$ group.

The term thiohydroxyl or thiol, as used herein, refers to a group of the formula —SH.

More particularly, the term "sulfide" refers to compound having a group of the formula —SR.

The term "sulfone" refers to compound having a sulfonyl group —S(O$_2$)R.

The term "sulfoxide" refers to a compound having a sulfinyl group —S(O)R

The term ureido refers to a urea group of the formula —NH—CO—NH$_2$.

Throughout the specification and claims, a given chemical formula or name shall encompass all tautomers, congeners, and optical- and stereoisomers, as well as racemic mixtures where such isomers and mixtures exist.

Certain compounds of the present disclosure may possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as D- or L- for amino acids, and individual isomers are encompassed within the scope of the present disclosure. The compounds of the present disclosure do not include those which are known in art to be too unstable to synthesize and/or isolate. The present disclosure is meant to include compounds in racemic, scalemic, and optically pure forms.

Optically active (R)- and (S)-, or D- and L-isomers may be prepared using chiral synthons or chiral reagents, or resolved using conventional techniques. When the compounds described herein contain olefenic bonds or other centers of geometric asymmetry, and unless specified otherwise, it is intended that the compounds include both E and Z geometric isomers.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

Unless otherwise stated, structures depicted herein are also meant to include compounds which differ only in the presence of one or more isotopically enriched atoms. For example, compounds having the present structures with the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present disclosure, whether radioactive or not, are encompassed within the scope of the present disclosure.

The compounds of the present disclosure may exist as salts. The present disclosure includes such salts. Examples of applicable salt forms include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent or by ion exchange. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

In addition to salt forms, the present disclosure provides compounds, which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

The term "protecting group" refers to chemical moieties that block some or all reactive moieties of a compound and prevent such moieties from participating in chemical reactions until the protective group is removed, for example, those moieties listed and described in T. W. Greene, P. G. M. Wuts, Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, without limitation, methyl, ethyl, and acetyl in the presence of amines blocked with acid labile groups such as tert-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(O)— catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups include, but are not limited to the following moieties:

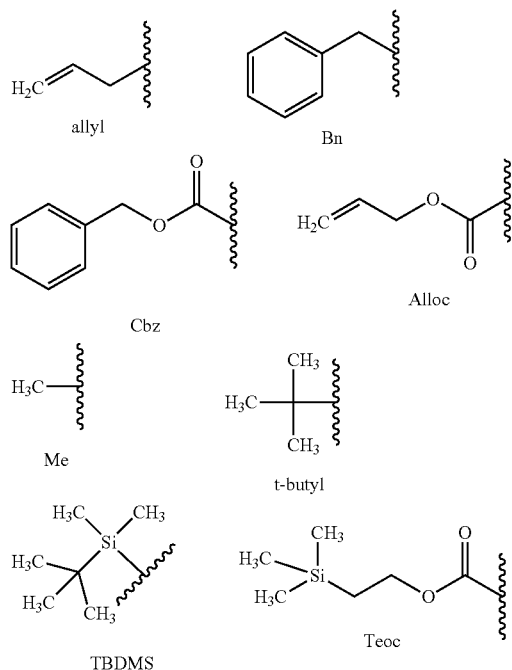

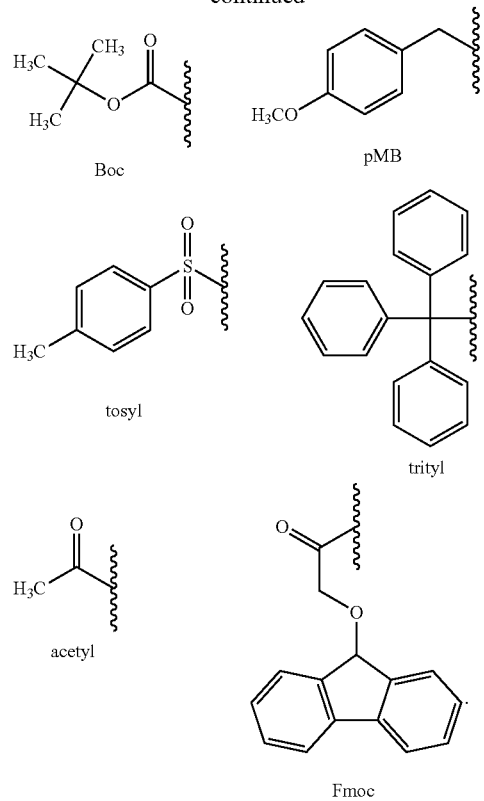

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Alkylamine-Substituted Perthiocarbamates: Dual Precursors to Hydropersulfide and Carbonyl Sulfide with Cardioprotective Actions 1.1 Overview The recent discovery of hydropersulfides (RSSH) in mammalian systems suggests their potential roles in cell signaling. The exploration of RSSH biological significance, however, is challenging due to their instability under physiological conditions. The presently disclosed subject matter provides the preparation, RSSH-releasing properties, and cytoprotective nature of alkylamine-substituted perthiocarbamates. Triggered by a base-sensitive, self-immolative moiety, these precursors show efficient RSSH release and also demonstrate the ability to generate carbonyl sulfide (COS) in the presence of thiols. Using this dually-reactive alkylamine-substituted perthiocarbamate platform, the generation of both RSSH and COS is tunable with respect to half-life, pH, and availability of thiols. Importantly, these precursors exhibit cytoprotective effects against hydrogen peroxide-mediated toxicity in H9c2 cells and cardioprotective effects against myocardial ischemia/reperfusion injury, indicating their potential application as new RSSH- and/or COS-releasing therapeutics.

1.2 Approach

Activation of prodrugs via intramolecular cyclization-elimination has been a widely used strategy for drug delivery. Saari et al., 1990; Gomes et al., 2007; and Blencowe et al., 2011. In this approach, active drug release is dependent upon a predictable intramolecular cyclization-elimination reaction. A strategy for RSSH release with the sulfhydryl group of RSSH protected in the form of perthiocarbamate 1 and a terminal non-nucleophilic quaternary ammonium salt is shown in Scheme 1.

Scheme 1. Design of hydropersulfide/carbonyl sulfide precursors.

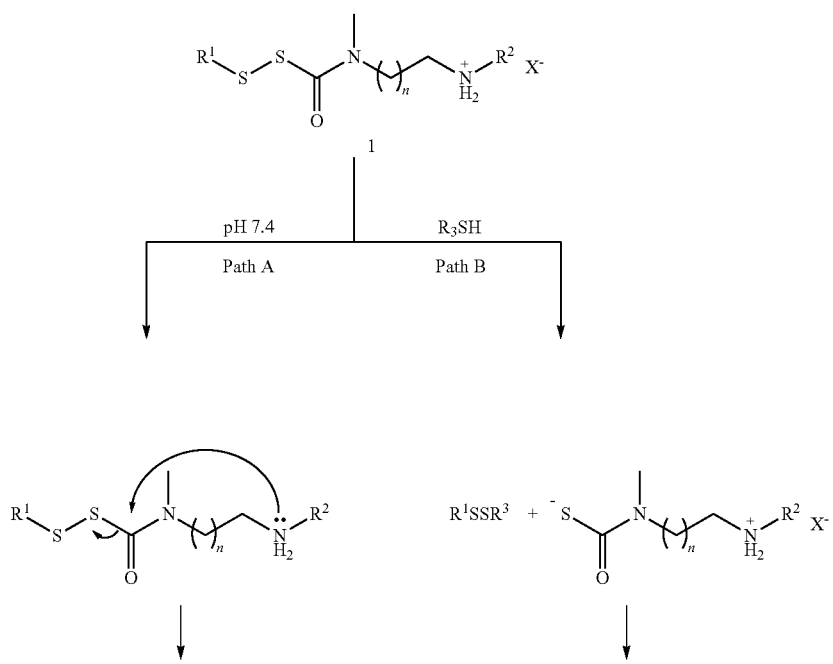

As shown in Scheme 1 (Path A), neutralization of the quaternary ammonium salt under physiological conditions forms an active amine nucleophile that can then undergo an intramolecular cyclization to release RSSH and a cyclic urea, presumably a biologically innocuous byproduct. Varying the substituent on the trigger nitrogen and changing the length of the methylene spacer should allow the rate of cyclization to be tuned, thereby varying RSSH release rates. Without wishing to be bound to any one particular theory, it also was thought that the alkyl substituent on the perthiocarbamate nitrogen would improve the aqueous stability of these precursors.

Recently, Pluth and co-workers have reported caged sulfenyl thiocarbonates (FIG. 1) that release carbonyl sulfide (COS) in the presence of biological thiols. Zhao et al., 2019. Under physiological condition, COS is rapidly hydrolyzed to $H_2S$ by the ubiquitous enzyme, carbonic anhydrase (CA). Chengelis and Neal, 1980. The detection of COS in human tissues suggests that it also may have regulatory roles in biology, Steiger et al., 2017, however, an understanding of these roles remains limited. To advance future investigations into the biological roles of COS, a series of COS donors that are activated by different triggers has been developed. Steiger et al., 2016; Zhao and Pluth, 2016; Powell et al., 2016; Sharma et al., 2017; Powell et al., 2019; Zhao et al., 2019, and Chauhan et al., 2019.

Again, without wishing to be bound to any one particular theory, it was thought that perthiocarbamates 1 also may produce COS in the presence of thiols as shown in Scheme 1, Path B. Under biological conditions, the RSSH released from Path A may react further with thiols to produce $H_2S$. Similarly, COS generated from Path B would be converted to $H_2S$ by CA.

1.3 Results and Discussion

To synthesize alkylamine-substituted perthiocarbamates, N-acetyl-cysteine methyl ester was treated with chlorocarbonylsulfenyl chloride to obtain the S-perthiocarbonyl chloride 3, which was immediately reacted with tert-butyl methyl(2-(methylamino)ethyl)carbamate in the presence of triethylamine to obtain 4 in 69% overall yield (Scheme 2). The tert-butoxycarbonyl (Boc) protecting group was removed by treatment with trifluoroacetic acid to obtain precursor 1a in 95% yield.

Scheme 2. Synthesis of hydropersulfide presursor 1a.

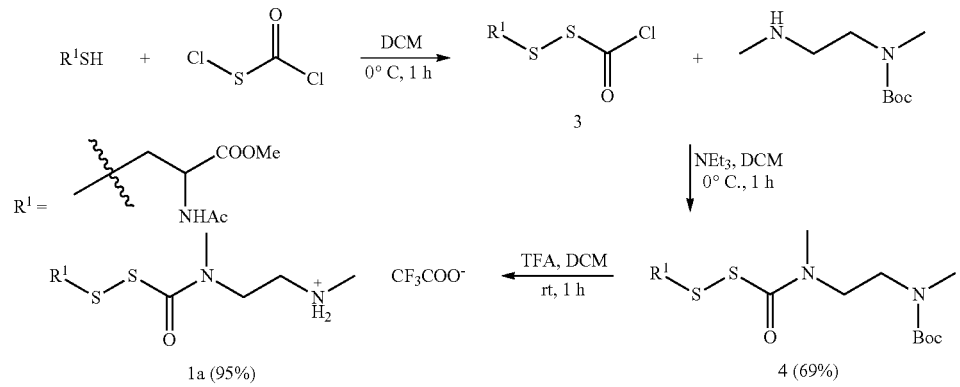

With 1a in hand, RSSH generation was examined using ultra-performance liquid chromatography-mass spectrometry (UPLC-MS). 0-(4-hydroxyphenyl)ethyl iodoacetamide (HPE-IAM) was used as an RSSH trap. HPE-IAM was chosen because it is a soft electrophile and has been widely used to estimate RSSH yields from biological samples. Akaike et al., 2017; Hamid et al., 2019. Incubation of 1a with HPE-IAM (50 equiv.) in ammonium bicarbonate buffer (pH 7.4, 50 mM) shows RSS-HPE-AM 5 formation (FIG. 8; Scheme 3, eq. 1), demonstrating the release of RSSH. Dialkyltrisulfide 6 formation, however, also is observed as a major product (Scheme 3, eq. 2), suggesting that precursor 1a is a competitive trap for the initially released RSSH. As expected, the byproduct 1,3-dimethyl-2-imidazolidinone (2a) is observed in 52% yield under these conditions, confirming that RSSH release occurs via intramolecular-cyclization reaction. To verify RSSH generation, 1a was independently incubated with N-ethyl maleimide (NEM, 50 equiv.) in pH 7.4 buffer and UPLC-MS analysis shows RSS-NEM adduct formation (FIG. 9a). In addition, improved yield (74%) of the byproduct 2a was observed and the level of trisulfide decreased in the presence of NEM (FIG. 9b), presumably due to its better RSSH-trapping efficiency vs. HPE-IAM.

Scheme 3. Proposed mechanism of RSSH and trisulfide formation from precursor 1a.

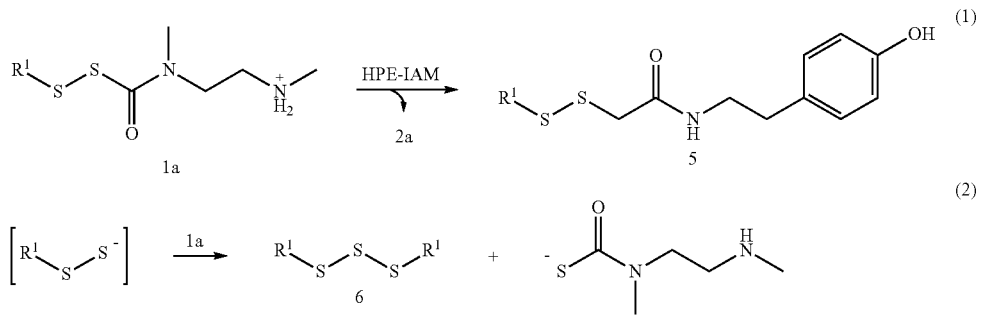

To minimize the reaction of released RSSH with its precursor, donor 7a (FIG. 2), which is equipped with an inhibiting dimethyl substituent alpha to the disulfide, was synthesized. RSSH generation from 7a was examined with HPE-IAM trapping and shows RSS-HPE-AM 9 formation with no evidence of dialkyltrisulfide generation (FIG. 10).

To support the proposed mechanism for RSSH release, RSSH release from a control compound 8 (Scheme 4) lacking the terminal amine group was examined. No RSSH release is observed from 8 under similar conditions (FIG. 11), confirming that the terminal amine is required for precursor activation.

The ability of 8 to release RSSH via intermolecular reactions with amines also was tested (Scheme 4, eq. 1). Incubation of 8 with a model amine, n-butylamine (5 equiv.), however, shows no reactivity, at least over 2 h (FIG. 12), suggesting that 8 is stable under these conditions and does not release RSSH via intermolecular reaction. Additionally, RSSH release from 8 in the presence of N-acetyl cysteine (NAC) was tested in pH 7.4 ammonium bicarbonate buffer. Without wishing to be bound to any one particular theory, it was thought that if thiol attacks the perthiocarbamate carbonyl group of 8, RSSH and/or RSSH derived polysulfides, and the NAC-thiocarbamate byproduct should be observed (Scheme 4, eq. 2). However, UPLC-MS analysis shows no evidence of these products (FIG. 13). Instead, mixed disulfide ($R^1SSR^3$) formation is observed, presumably formed by the thiol attack on the internal sulfur of the compound 8 (Scheme 4, eq. 3). Furthermore, mixed disulfide $R^1SSR^3$ undergoes disulfide exchange reaction with NAC to produce N-acetyl cystine ($R^3SSR^3$) and N-acetyl-penicillamine methyl ester ($R^1SH$) (Scheme 4, eq. 4). Together, these results indicate that the control compound 8 does not release RSSH via intermolecular reactions in the presence of amines or thiols.

Scheme 4. Reaction of 8 with n-BuNH2 and N-acetyl cysteine

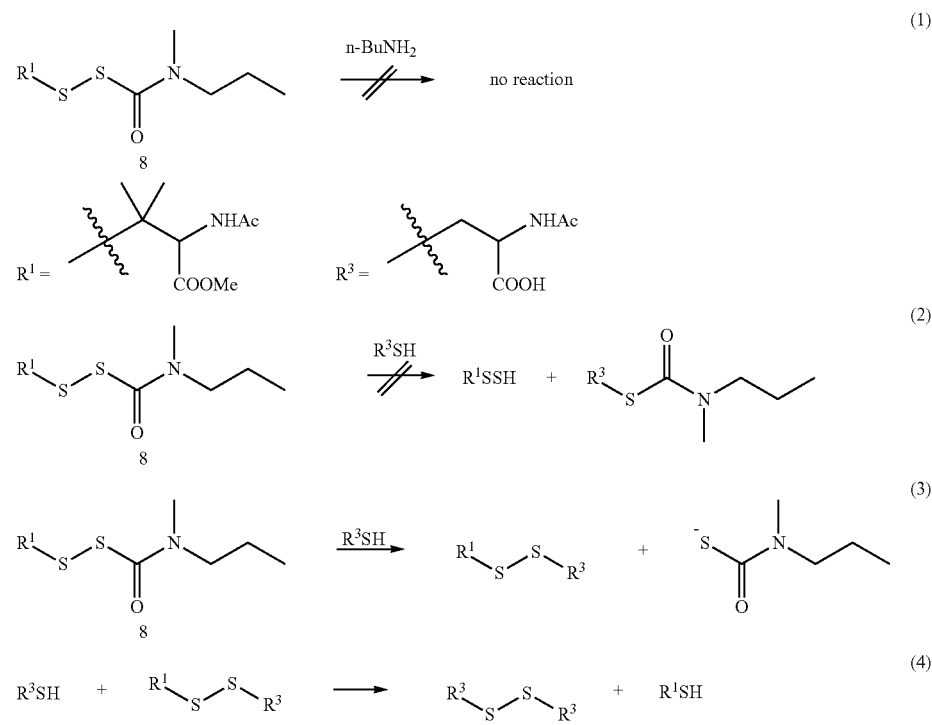

Next, the kinetics of RSSH release from 7a was monitored by HPE-IAM trapping in pH 7.4 phosphate buffer at 37° C. using HPLC. An increase in peak intensity at 14.1 min attributed to RSS-HPE-AM 9 is observed (FIG. 3b). To quantify RSSH, 9 was independently synthesized (Scheme 5, herein below). HPLC analysis shows 89% formation of 9 from 7a with a first-order rate constant of k=0.505 min$^{-1}$ ($t_{1/2}$=1.4 min, Table 1). In addition, 87% of byproduct 2a formation, analyzed using UPLC-MS, also is observed (FIG. 10). The kinetics of 9 (k=0.58±0.02 min$^{-1}$; (12=1.2 min) and 2a (0.57±0.02 min$^{-1}$; ($t_{1/2}$=1.2 min) formation from 7a using UPLC-MS were analogously measured and observed similar rate constants, indicating that RSSH trapping with HPE-IAM is rapid under these conditions (FIG. 14). The effect of pH on the kinetics of RSSH release also was examined. As expected, the rate of RSSH release from 7a decreases at pH 6.0 (k=0.031 min$^{-1}$; $t_{1/2}$=22.2 min) and increases at pH 8.0 (k=2.58 min$^{-1}$; $t_{1/2}$=0.27 min).

Scheme 5. Synthesis of RSS-HPE-AM 9.

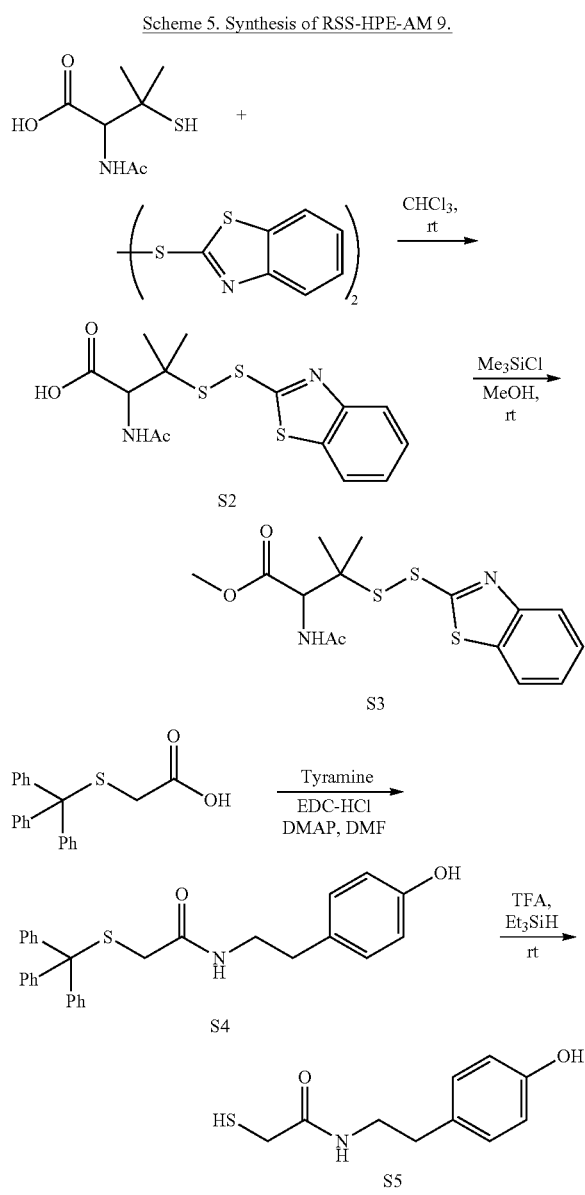

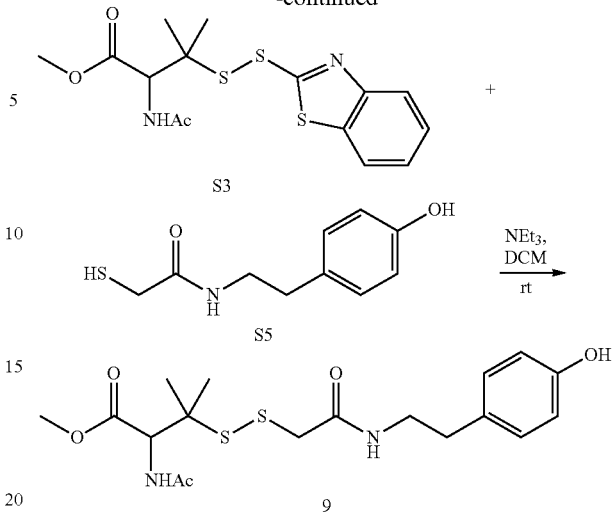

To tune the kinetics of RSSH release, precursor 7b with a terminal free amine was synthesized. HPLC analysis shows an increase in half-life (16.7 min, Table 1) at pH 7.4. Similar to precursor 7a, a pH effect on RSSH release for 7b ($t_{1/2}$=280 min at pH 6.0; t/2=5.1 min at pH 8.0) also was observed. Precursor 7c, equipped with three methylene spacers, was synthesized to measure its effect on RSSH release. It was thought that inclusion of a longer spacer compared with that in precursor 7a would reduce the rate of the intramolecular-cyclization reaction and therefore RSSH release. As expected, the half-life of 7c increases to 118 min, still with 90% RSSH release. In addition, 88% of the expected byproduct 1,3-dimethyltetrahydropyrimidin-2(1H)-one (2c) also is observed (FIG. 15). Analogously, significantly slower RSSH release ($t_{1/2}$=484 min) from 7d, which is equipped with both a terminal free amine and three methylene spacers, also was observed. Taken together, these results demonstrate the ability of the perthiocarbamate platform to release RSSH efficiently with tunable rates and over long time frames.

TABLE 1

Hydropersulfide Yields and Half-lives for Precursors 7a-d

| Precursor | R² | n | Hydropersulfide Yield (%)$^a$ | $t_{1/2}$ (min) |
|---|---|---|---|---|
| 7a | CH₃ | 1 | 89 ± 3 | 1.4 ± 0.1 |
| 7b | H | 1 | 94 ± 1 | 16.7 ± 0.3 |
| 7c | CH₃ | 2 | 90 ± 1 | 118 ± 4 |
| 7d | H | 2 | 82 ± 1 | 484 ± 10 |

$^a$RSSH precursors (100 μM) were incubated in the presence of HPE-IAM (5 mM) in pH 7.4 phosphate buffer containing DTPA at 37° C. Reported data represent averages ± SD (n = 3).

The ability of these precursors to release RSSH also was examined in the presence of thiols, which are likely to be present in significant concentrations under physiological conditions. Because thiols also can readily react with HPE-IAM, RSSH release was measured in its absence. It was thought that if thiol reaction with the precursor (Scheme 6, eq. 2) competes with RSSH release (Scheme 6, eq. 1), reduced yields of RSSH and cyclic ureas 2a-d and increased formation of thiocarbamate-derived COS and unsymmetrical disulfide 10 (R¹SSR³) should be observed. Since RSSH is an unstable species under aqueous conditions, the cyclic-urea yields were measured as an indication of RSSH yield.

Scheme 6. RSSH and COS Generation from 7a-d in the Presence of Thiol.

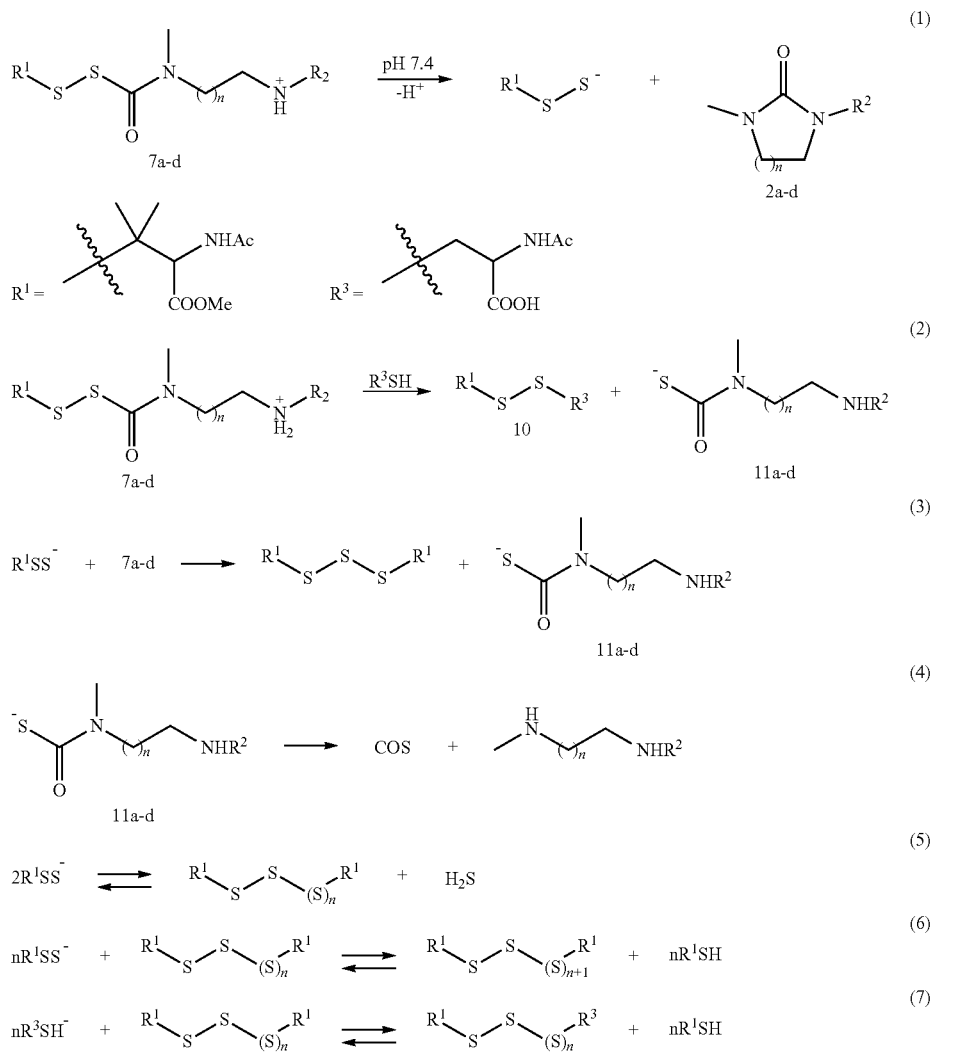

When 7a is incubated with NAC in pH 7.4 buffer, a new peak at 5.67 min with m/z=238.0556 [M+H]$^+$ corresponding to RSSH (expected m/z=238.0566) is observed (FIG. 4 and FIG. 16). Furthermore, symmetrical dialkyl polysulfide ($R^1SS_nSR^1$, n=1-4) formation also is observed (FIG. 4, cy an highlight), presumably formed by the decomposition of RSSH through disproportionation (Scheme 6, eq. 5) and RS SH-poly sulfide exchange reactions (Scheme 6, eq. 6). In addition, unsymmetrical dialkyl polysulfide ($R^1SS_nSR^3$, n=1-3) (FIG. 4, pink highlight), likely produced by the NAC reaction with symmetrical dialkyl polysulfides, also is observed. The presence of an observable MS peak for RSSH under these conditions is likely due to its equilibrium with polysulfides and its relative stability as a sterically hindered persulfide. Notably, 87% of byproduct 2a is observed under these conditions (Table 2), suggesting that the efficiency of RSSH generation for short-lived precursor 7a is unaffected by thiol.

RSSH generation from 7a in the absence of a trapping agent also was examined. As shown in FIG. 17, a peak at 5.67 min corresponding to RSSH, as well as polysulfides ($R^1SS_nSR^1$, n=1-4) and N-acetyl-penicillamine methyl ester was observed again, indicating that RSSH undergoes disproportionation reactions and its presence is likely due to equilibrium reactions with polysulfides. In contrast, UPLC-MS analysis of RSSH release from precursor 1a in the absence of trap shows no evidence of an MS-observable RSSH peak (FIG. 18), consistent with the relatively unstable nature of primary alkyl persulfides.

TABLE 2

Yields of 2a-d from Precursors 7a-d in the Presence of N-acetyl Cysteine

| Precursor | 7a | 7b | 7c | 7d |
|---|---|---|---|---|
| Byproduct %$^a$ | 87 ± 1 | 58 ± 0.7 | 19.2 ± 0.5 | 5.9 ± 0.4 |

$^a$RSSH precursors (100 μM) were incubated in the presence of NAC (500 μM) in pH 7.4 ammonium bicarbonate buffer containing DTPA (100 μM) at 37° C. Reported data represent averages ± SD (n = 3).

Thiocarbamate 11a formation, another anticipated product of precursor 7a reaction with NAC, also was examined (Scheme 6, eq. 2). UPLC-MS analysis showed no evidence of thiocarbamate formation, suggesting that if it formed, it rapidly decomposes under aqueous conditions to release COS (Scheme 6, eq. 4). COS production was monitored using membrane inlet mass spectrometry (MIMS), a technique used to detect hydrophobic gases dissolved in aqueous solution using semi-permeable membrane that allows gases and not the liquid phase to enter a mass spectrometer. Cline et al., 2011.

When precursor 7a is examined in the absence of NAC, a very small increase in the m/z=60 signal attributed to COS (FIG. 5a) is observed, likely arising from released RSSH reaction with precursor 7a producing thiocarbamate 11a, which subsequently decomposes to give COS (Scheme 6, eq. 3 and 4). Only a small additional increase in COS signal (FIG. 5b) is observed in the presence of NAC, suggesting that 7a rapidly releases RSSH (Scheme 6, eq. 1) and thus is less available to react with NAC (Scheme 6, eq. 2). Taken together, these results again demonstrate that 7a mainly produces RSSH, even in the presence of thiols.

Next, precursor 7b decomposition was examined in the presence of NAC. UPLC-MS analysis shows decreased byproduct 2b yield (58%), and reduced levels of $R^1SS_nSR^1$ and $R^1SS_nSR^3$ (FIG. 19). Consistent with this observation, increased production of COS (FIG. 5b) also was observed. These results suggest that with decreasing RSSH release rate, precursor reaction with thiol becomes more competitive. Furthermore, mainly unsymmetrical disulfide 10 (FIG. 20 and FIG. 21) and COS (FIG. 5b), and reduced yields of 2c and 2d (Table 2) from precursors 7c and 7d, respectively, is observed in the presence of NAC. These results indicate that donors 7c and 7d produce mainly COS in the presence of thiol.

In addition to COS formation, thiocarbamates 11b-d also can potentially undergo an intramolecular cyclization to produce cyclic ureas 2b-d and $H_2S$. Reduced yields of 2b-d during 7b-d decomposition in the presence of NAC was observed, however, indicating that this cyclization reaction is not a major contributor. Furthermore, the predicted pKa of the thiocarbamate sulfhydryl group is ca. 5.5, indicating that it will be predominantly present in anionic form at pH 7.4, thus disfavoring intramolecular cyclization to release $H_2S$. Note that pKa is calculated using Advance Chemistry Development (ACD/Labs) Software V11.02.

The control compound 8 also was examined for COS release under similar conditions. Relatively slow COS release compared with that from 7a-d is found (FIG. 5b). This result suggests that in the cases of precursors 7a-d, in addition to the thiol-mediated COS release pathway (Scheme 6, eq. 2), RSSH reaction with the precursor to produce the thiocarbamate intermediate (Scheme 6, eq. 3) presumably contributes to the observed enhanced rate of COS release.

Although partial COS production is observed from longer-lived precursors 7b-7d in the presence of thiols, the COS generation pathway might be disfavored under certain conditions. For example, patients with cardiovascular disease often have reduced levels of glutathione. Wang et al., 2013; Bajic et al., 2019.

This result implies that under reduced thiol levels, these precursors may favor the RSSH generation pathway. Furthermore, during myocardial ischemia injury, the local pH changes to mildly acidic, Effros et al., 1975; Yan and Kléber, 1992, and under these conditions, thiol reaction with the RSSH precursor may be diminished. Based on these conditions, COS release from 7b-d with NAC was examined in pH 6.0 buffer at 37° C. As expected, diminished levels of COS are observed (FIG. 22). Under the same conditions, RSSH release from 7b is still observed, albeit at a slower rate (FIG. 23).

The reactivity of NAC vs. GSH with precursor 7b at pH 7.4 also was compared. Without wishing to be bound to any one particular theory, it was thought that if GSH reaction with the precursor is slower than NAC, increased yield of RSSH and cyclic urea 2b (Scheme 6, eq. 1), and reduced levels of thiocarbamate-derived COS and unsymmetrical disulfide 10 ($R^1SSR^3$) (Scheme 6, eq. 2) should be observed. When 7b is incubated with NAC, UPLC-MS analysis shows 58% of byproduct 2b formation. In the presence of GSH, a small decrease in 2b yield (42%) was observed, suggesting that GSH reaction with 7b is slightly faster than NAC. Consistent with this observation, increased levels of unsymmetrical disulfide ($R^1SSR^3$) and reduced levels of RSSH-derived symmetrical dialkyl polysulfides ($R^1SS_nSR^1$, n=1 and 2) and unsymmetrical dialkyl polysulfides ($R^1SS_nSR^3$, n=1 and 2) (FIG. 24) also were observed in the case of GSH reaction with 7b. Additionally, slightly higher/faster COS release from 7b in the presence of GSH was observed compared with NAC, analyzed by MIMS (SI, FIG. 107). Together, these results indicate that precursor 7b reaction with GSH ($pK_a$ 8.83) is slightly faster than with NAC ($pK_a$ 9.52), likely due to the higher concentration of the corresponding thiolate at neutral pH. Zhao et al., 2019; Aldini et al., 2018.

Several studies have speculated that intracellular RSSH and related species protect cells from oxidative stress. Ida et al., 2014; Ono et al, 2014; Numakura et al., 2017; Kunikata et al., 2017; Saund et al., 2015; Millikin et al., 2016; Shibata et al., 2016; and Bianco et al., 2016. Whether the presently disclosed alkylamine-substituted perthiocarbamates exert protective effects against oxidative stress and myocardial ischemia-reperfusion (I/R) injury was investigated. The medium-lived precursor 7b ($t_{1/2}$=16.7 min) was chosen for the studies. First, the cytotoxicity of 7b on H9c2 myoblasts was measured using the nucleic acid stain, SYTOX®, a probe for compromised cell membrane integrity. Jones and Singer, 2001. Both precursor 7b and its byproduct 2b show no toxicity toward H9c2 cells after 24 h of exposure at varied concentrations (0-150 µM) (FIG. 11). The cytoprotective effects of 7b against oxidative stress in H9c2 cells was then measured. $H_2O_2$ (200 µM) was given as a pro-oxidant source, and drastically reduced cell viability was observed using CCK-8 staining (FIG. 6a). Ishiyama et al., 1997; Tominaga et al., 1999.

Pretreating myoblasts with precursor 7b for 2 h, however, resulted in a dose-dependent attenuation of $H_2O_2$-induced toxicity (FIG. 6a). Under similar conditions, the byproduct 2a shows no protective effect against $H_2O_2$-mediated toxicity, suggesting that the protection is due to RSSH and/or COS. Next, the cytoprotective effect of 7b was independently evaluated using the SYTOX® assay, due to the potential background reduction of CCK-8 by reactive sulfur species leading to artifactual viability measurements. Bianco et al., 2019; Lin et al., 2019. As shown in FIG. 6b, 7b consistently shows protective effects against $H_2O_2$-mediated toxicity. Under similar conditions, the COS precursor 8 also shows protective effects against $H_2O_2$-mediated toxicity, but to a lesser extent compared with 7b (FIG. 26). Altogether these results suggest that 7b is not cytotoxic to cardiac-derived tissue, can be taken up by the cells, and confers protection against oxidative stress.

To build on the results from these in vitro studies, 7b also was tested in isolated-perfused (ex vivo) mouse hearts. The Langendorff model of myocardial ischemia-reperfusion is a widely used technique whereby the ionotropic and chronotropic effects of a drug can be studied directly without confounding neural/hormonal influences and minimizes changes in coronary vascular tone. Pagliaro et al., 2003; Bell et al., 2011. Following 20 min of global ischemia, 7b was infused for the first 7 min of reperfusion at a concentration of 100 μM. Reperfusion is continued for a total duration of 90 min before the heart is infused with triphenyltetrazolium chloride (TTC), a stain for determining cellular viability within a given tissue. Rossello et al., 2016.

FIG. 7a shows coronal sections of murine hearts stained with TTC. After 20 min global ischemia (I/R), Krebs-Henseleit (KH) perfused hearts show 42% infarct size (FIG. 7b). This loss in viable myocardial tissue was significantly attenuated in 7b-perfused infarcted hearts (16% infarct size). These data demonstrate that RSSH and/or COS can provide protection when given at reperfusion in hearts subjected to I/R injury. Although more work remains to be done to determine the mechanism by which RSSH conditions the tissue to deal with the stress of reperfusion and/or compensates for the damage incurred during ischemia, these data combined with in-vitro cellular studies imply that the alkylamine-substituted perthiocarbamates reported here can reduce the extent of myocardial ischemia-reperfusion injury and may be pharmacologically useful.

1.4 Summary

In summary, alkylamine-substituted perthiocarbamates have been prepared as a new, versatile, and readily modifiable platform for controllable RSSH release. These precursors show efficient RSSH release with half-lives ranging from 1.4 to 484 min in the presence of HPE-IAM. For long-lived precursors, COS also is produced along with RSSH in the presence of thiols. Alkylamine-substituted perthiocarbamates are an example of prodrugs in which RSSH generation is not dependent upon exogenous reactivity, but rather from an intramolecular cyclization-elimination reaction. Furthermore, the terminal amine of these precursors can be conjugated with functional groups that respond to specific stimuli such as light, redox-reactions, or enzymes to achieve spatiotemporal control over RSSH release. The potential therapeutic benefit of these precursors has been demonstrated in the context of oxidative stress and myocardial ischemia-reperfusion injury. As such, it is thought that these precursors will find significant utility as chemical tools for investigating RSSH and COS biology.

1.5 General Methods

Analytical thin layer chromatography (TLC) was performed on silica gel on TLC Al foils with fluorescent indicator F254 plates (Sigma-Aldrich). Visualization was accomplished with UV light (254 nm) or staining with $KMnO_4$. Starting materials, solvents, and reagents were received from commercial sources (Sigma-Aldrich, Oakwood Chemical, and TCI), unless otherwise noted and were used without purification. Deuterated solvents (Cambridge Isotope Laboratories) were used for NMR spectroscopic analyses. NMR spectra were obtained on a Bruker 400 MHz NMR spectrometer. In the case of $^1$H NMR in $CDCl_3$, chemical shifts are reported relative to tetramethylsilane (δ=0). The other spectra are referenced internally according to residual solvent signals of $CDCl_3$ ($^{13}$C NMR; δ=77.16 ppm), and DMSO-$d_6$ ($^1$H NMR; δ=2.50 ppm, $^{13}$C NMR; δ=39.52 ppm). High-resolution mass spectra were obtained on a Waters Acquity Q-ToF MS/MS instrument. The kinetics of RSSH generation were measured using a high-performance liquid chromatography (HPLC, Agilent 1100 series) system with a Phenomenex C-18 reverse phase column (250 mm×4.6 mm, 5 μm). UPLC-MS analysis was carried out with a Waters Acquity/Xevo-G2 UPLC-MS system equipped with ACQUITY UPLC BEH C18 column (2.1 mm×50 mm, 1.7 μm). The mass signals for products of RSSH trapping with β-(4-hydroxyphenyl)ethyl iodoacetamide (HPE-IAM) were obtained via deconvolution using MassLynx 4.1 software. In addition to the protonated molecule [M+H]$^+$, [M+Na]$^+$ adduct also was observed during ES-MS analysis. The pH measurements were performed using a Fisher Scientific Accumet AB15 pH-meter.

1.6 Chemical Synthesis tert-Butyl (2-(methylamino)ethyl)carbamate and tert-butyl (3-(methylamino)propyl)carbamate were received from the commercial sources. tert-Butyl methyl(2-(methylamino)ethyl)carbamate, Meyer et al., 2010, and tert-butyl methyl(3-(methylamino)propyl)carbamate, Devine et al., 2017, were synthesized using a previously reported procedure and the analytical data collected was consistent with the reported values.

General Note—

$^1$H and $^{13}$C NMR spectra of compounds 4, S1a, S1b, S1c, S1d, and 8 show two sets of some signals at 24° C., likely due to the presence of rotamers. Hence, $^1$H and $^{13}$C NMR spectra were acquired at 24° C., and 70° C. or 80° C. to distinguish these rotamers.

Methyl-13-acetamido-2,2,5,8-tetramethyl-4,9-dioxo-3-oxa-10,11-dithia-5,8-diazatetradecan-14-oate (4)

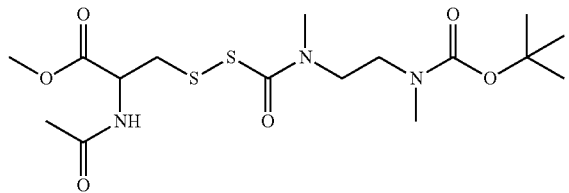 [SMILES: COC(=O)C(CSSC(=O)N(C)CCN(C)C(=O)OC(C)(C)C)NC(C)=O]

A solution of chlorocarbonylsulfenyl chloride (288 mg, 2.2 mmol) in dichloromethane (4 mL) was added dropwise to the solution of N-acetyl-cysteine methyl ester (354 mg, 2 mmol) in dichloromethane (4 mL) at 0° C. under a nitrogen atmosphere. The reaction mixture was stirred at 0° C. for 1 h and volatiles were removed under vacuum to obtain S-perthiocarbonyl chloride 3. This compound was immediately dissolved in anhydrous dichloromethane (3 mL) and added slowly into a cold solution (0° C.) of tert-butyl methyl(2-(methylamino)ethyl)carbamate (376 mg, 2 mmol) and triethylamine (223 mg, 2.2 mmol) in dichloromethane (5 mL). The reaction mixture was stirred at 0° C. for 1 h, quenched with water (20 mL) and extracted with dichloromethane (3×10 mL). The combined organic layer was washed with brine (3×10 mL), dried over anhydrous $Na_2SO_4$, and evaporated under vacuum. The residue was purified by flash column chromatography on silica gel to afford the product 4 (mixture of rotamers) as a semisolid (586 mg, 69% yield); $^1$H NMR (400 MHz, DMSO, 24° C.) δ 8.43 (d, J=7.3 Hz, 1H), 4.51-4.46 (m, 1H), 3.63 (s, 3H), 3.49 (bs, 2H), 3.34 (bs, 2H), 3.10-2.91 (m, 5H), 2.77 (s, 3H), 1.86 (s, 3H), 1.37 (s, 9H); $^{13}$C NMR (101 MHz, DMSO, 24°

C.) δ 170.9, 169.4, 163.9, 154.9, 154.5, 78.8, 78.6, 52.1, 51.1, 47.9, 47.1, 46.4, 45.6, 44.8, 35.9, 35.4, 35.2, 34.2, 34.0, 33.6, 28.0, 22.3; $^1$H NMR (400 MHz, DMSO, 70° C.) δ 8.21 (d, J=7.3 Hz, 1H), 4.56-4.51 (m, 1H), 3.65 (s, 3H), 3.51 (t, J=5.6 Hz, 2H), 3.36 (t, J=5.6 Hz, 2H), 3.09-3.03 (m, 2H), 3.00 (s, 3H), 2.80 (s, 3H), 1.87 (s, 3H), 1.40 (s, 9H); $^{13}$C NMR (101 MHz, DMSO, 70° C.) δ 170.4, 168.9, 164.1, 154.4, 78.4, 51.7, 51.2, 51.1, 47.5, 45.5, 35.0, 34.0, 27.8, 21.9; HRMS (ESI): m/z cald. for $C_{16}H_{29}N_3O_6S_2Na^+$ [M+Na]$^+$ 446.1390, found 446.1391.

2-(((2-Acetamido-3-methoxy-3-oxopropyl)disulfannecarbonyl)(methyl)amino)-N-methylethan-1-aminium (1a)

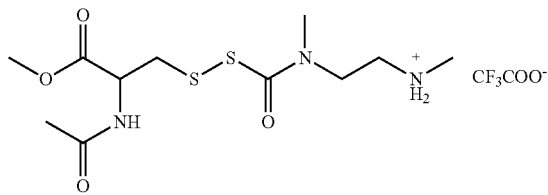

N-Boc protected compound 4 (252 mg, 0.59 mmol) was dissolved in a 1:1 mixture of dichloromethane:trifluoroacetic acid (4 mL) and the solution was stirred at room temperature for 1 h. The solvent was evaporated under vacuum, dichloromethane was successively added and evaporated to remove the residual TFA, to provide the precursor 1a as a semisolid (246 mg, 95% yield); $^1$H NMR (400 MHz, DMSO) δ 8.57 (s, 2H), 8.48 (d, J=7.7 Hz, 1H), 4.54 (td, J=8.2, 5.4 Hz, 1H), 3.77-3.51 (m, 5H), 3.25-2.91 (m, 7H), 2.59 (s, 3H), 1.87 (s, 3H); $^{13}$C NMR (101 MHz, CDCl$_3$) δ 171.4, 171.3, 169.0, 161.4 (q, J=36.3 Hz), 116.2 (q, J=290.3 Hz), 52.8, 50.9, 47.3, 47.2, 41.1, 35.7, 33.6, 22.7; HRMS (ESI): m/z calcd. for $CH_{22}N_3O_4S_2^+$ [M]$^+$ 324.1046, found 324.1052.

N-Acetyl-penicillamine Methyl Ester

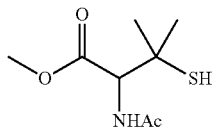

N-acetyl-penicillamine methyl ester was synthesized following a previously reported method. Li and Sha, 2008. To a solution of N-acetyl-D-penicillamine (1.68 g, 8.8 mmol) in anhydrous methanol (40 mL) under a nitrogen atmosphere, chlorotrimethylsilane (1.91 g, 17.6 mmol) was added. The mixture was stirred at room temperature for 16 h. The solvent was evaporated under vacuum, and the residue was purified by flash chromatography (silica gel, eluent: 50% ethyl acetate in hexane) to afford the title compound as a white solid (0.75 g, 41% yield); $^1$H NMR (400 MHz, CDCl$_3$) δ 6.42 (d, J=8.6 Hz, 1H), 4.63 (d, J=9.4 Hz, 1H), 3.73 (s, 3H), 2.05 (s, 3H), 1.97 (d, J=1.3 Hz, 1H), 1.47 (s, 3H), 1.33 (d, J=1.2 Hz, 3H); $^{13}$C NMR (101 MHz, CDCl$_3$) δ 171.1, 170.0, 60.4, 52.3, 46.6, 31.2, 29.5, 23.3; HRMS (ESI): m/z calcd. for $CH_{15}NO_4S$ [M+Na]$^+$ 228.0665, found 228.0661.

1.6.1 General Procedure for Synthesis of N-Boc Protected RSSH/COS Precursors (S1a-d)

A solution of chlorocarbonylsulfenyl chloride (1.1 equiv.) in anhydrous dichloromethane (4 mL) was added dropwise to the solution of N-acetyl-penicillamine methyl ester (1 equiv.) in dichloromethane (4 mL) at 0° C. under a nitrogen atmosphere. The reaction mixture was stirred at 0° C. for 1 h, and volatiles were removed under vacuum. The residue was immediately dissolved in anhydrous dichloromethane (3 mL), and slowly added into a mixture of N-Boc protected diamine (1 equiv.) and triethylamine (1.1 equiv.) in dichloromethane (5 mL) at 0° C. The resulting solution was stirred at 0° C. for 1 h. The reaction mixture was quenched by water (20 mL) and extracted with dichloromethane (3×10 mL). The combined organic layer was washed with brine (3×10 mL), dried over anhydrous Na$_2$SO$_4$, and evaporated under vacuum. The residue was purified by flash chromatography on silica gel using ethyl acetate (EA) and petroleum ether (PE) as eluent to afford the desired product as a mixture of rotamers.

Methyl 13-acetamido-2,2,5,8,12,12-hexamethyl-4,9-dioxo-3-oxa-10,11-dithia-5,8-diazatetradecan-14-oate (S1a)

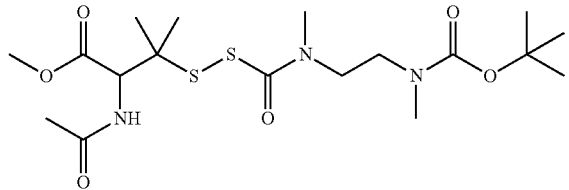 [SMILES: COC(=O)C(NC(C)=O)C(C)(C)SSC(=O)N(C)CCN(C)C(=O)OC(C)(C)C]

633 mg, 78% yield; semisolid; $^1$H NMR (400 MHz, DMSO, 24° C.) δ 8.30 (d, J=8.6 Hz, 1H), 4.49 (d, J=8.6 Hz, 1H), 3.63 (s, 3H), 3.54 (s, 2H), 3.37 (s, 2H), 3.06 (s, 1.6H), 2.95 (s, 1.4H), 2.80 (s, 1.4H), 2.74 (s, 1.6H), 1.89 (s, 3H), 1.37 (s, 9H), 1.25 (s, 6H); $^{13}$C NMR (101 MHz, DMSO, 24° C.) δ 170.2, 169.5, 164.3, 164.0, 154.9, 154.5, 78.5, 58.2, 51.8, 47.9, 47.6, 47.1, 46.1, 45.5, 44.6, 35.8, 35.5, 35.0, 34.7, 34.3, 33.9, 33.6, 24.5, 23.7, 23.5, 22.2; $^1$H NMR (400 MHz, DMSO, 80° C.) δ 7.98 (d, J=8.7 Hz, 1H), 4.54 (d, J=8.7 Hz, 1H), 3.66 (s, 3H), 3.55 (t, J=6.0 Hz, 2H), 3.38 (t, J=6.0 Hz, 2H), 3.02 (s, 3H), 2.81 (s, 3H), 1.92 (s, 3H), 1.41 (s, 9H), 1.32 (s, 3H), 1.30 (s, 3H); $^{13}$C NMR (101 MHz, DMSO, 80° C.) δ 169.6, 169.0, 164.2, 154.4, 78.4, 58.3, 51.6, 51.1, 47.5, 45.4, 35.0, 33.9, 27.7, 24.4, 23.8, 21.8; HRMS (ESI): m/z calcd. for $C_{18}H_{33}N_3O_6S_2Na^+$ [M+Na]$^+$ 474.1703, found 474.1713.

Methyl 13-acetamido-2,2,8,12,12-pentamethyl-4,9-dioxo-3-oxa-10,11-dithia-5,8-diazatetradecan-14-oate (S1b)

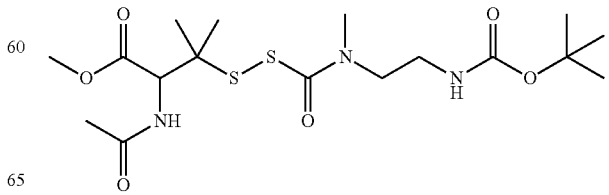

614 mg, 78% yield; semisolid; $^1$H NMR (400 MHz, DMSO, 24° C.) δ 8.31 (d, J=8.5 Hz, 1H), 7.02 (s, 0.5H), 6.85 (s, 0.5H), 4.50 (d, J=8.5 Hz, 1H), 3.63 (s, 3H), 3.45-3.40 (m, 2H), 3.12-2.93 (m, 5H), 1.89 (s, 3H), 1.36 (s, 9H), 1.26 (s, 6H); $^{13}$C NMR (101 MHz, DMSO, 24° C.) δ 170.3, 169.5, 164.5, 164.3, 155.6, 77.8, 77.7, 58.3, 58.2, 51.8, 49.7, 49.5, 37.6, 37.4, 35.5, 35.2, 28.2, 24.5, 23.8, 23.7, 22.2; $^1$H NMR (400 MHz, DMSO, 80° C.) δ 7.99 (d, J=8.4 Hz, 1H), 6.55 (s, 1H), 4.54 (d, J=8.7 Hz, 1H), 3.66 (s, 3H), 3.46 (t, J=6.1 Hz, 2H), 3.14 (q, J=6.1 Hz, 2H), 3.03 (s, 3H), 1.92 (s, 3H), 1.39 (s, 9H), 1.32 (s, 3H), 1.31 (s, 3H); $^{13}$C NMR (101 MHz, DMSO, 80° C.) δ 169.6, 169.0, 164.4, 155.1, 77.5, 58.4, 51.6, 51.1, 49.4, 37.6, 35.1, 27.8, 24.5, 23.9, 21.8; HRMS (ESI): m/z calcd. for $C_{17}H_{31}N_3O_6S_2Na^+$ [M+Na]$^+$ 460.1546, found 460.1550.

Methyl 14-acetamido-2,2,5,9,13,13-hexamethyl-4,10-dioxo-3-oxa-11,12-dithia-5,9-diazapentadecan-15-oate (S1c)

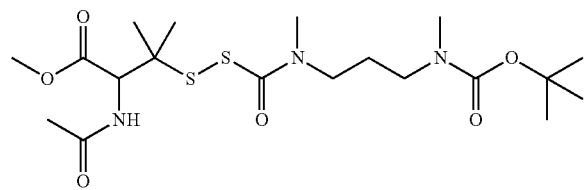 [SMILES: COC(=O)C(NC(C)=O)C(C)(C)SSC(=O)N(C)CCCN(C)C(=O)OC(C)(C)C]

360 mg, 58% yield; semisolid; $^1$H NMR (400 MHz, DMSO, 24° C.) δ 8.30 (d, J=8.7 Hz, 1H), 4.51 (d, J=8.7 Hz, 1H), 3.63 (s, 3H), 3.43-3.37 (m, 2H), 3.19-2.94 (m, 5H), 2.77 (s, 3H), 1.89 (s, 3H), 1.77-1.69 (m, 2H), 1.39 (s, 9H), 1.26 (s, 6H); $^{13}$C NMR (101 MHz, DMSO, 24° C.) δ 170.2, 169.5, 164.1, 163.6, 154.6, 78.4, 58.1, 47.8, 47.3, 45.9, 45.2, 35.4, 34.7, 33.7, 28.0, 26.2, 25.3, 24.5, 23.6, 22.2; $^1$H NMR (400 MHz, DMSO, 80° C.) δ 7.98 (d, J=8.7 Hz, 1H), 4.55 (d, J=8.7 Hz, 1H), 3.66 (s, 3H), 3.40 (t, J=7.2 Hz, 2H), 3.19 (t, J=7.2 Hz, 2H), 3.03 (s, 3H), 2.80 (s, 3H), 1.92 (s, 3H), 1.78 (quintet, J=7.2 Hz, 2H), 1.42 (s, 9H), 1.32 (s, 3H), 1.30 (s, 3H); $^{13}$C NMR (101 MHz, DMSO, 80° C.) δ 169.6, 169.0, 163.9, 154.4, 78.1, 58.2, 51.6, 51.1, 47.4, 45.5, 34.6, 33.4, 27.7, 25.4, 24.4, 23.8, 21.8; HRMS (ESI): m/z calcd. for $C_{19}H_{36}N_3O_6S_2^+$ [M+H]$^+$ 466.2040, found 466.2041.

Methyl 14-acetamido-2,2,9,13,13-pentamethyl-4,10-dioxo-3-oxa-11,12-dithia-5,9-diazapentadecan-15-oate (S1d)

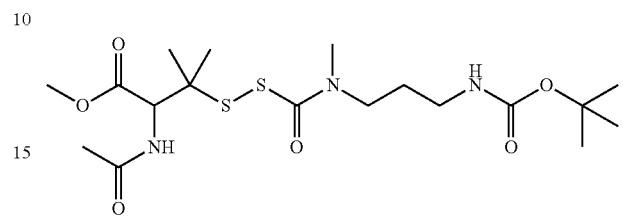

816 mg, 77% yield; semisolid; S1d; $^1$H NMR (400 MHz, DMSO, 24° C.) δ 8.31 (d, J=8.7 Hz, 1H), 6.90 (s, 0.5H), 6.76 (s, 0.5H), 4.50 (d, J=8.7 Hz, 1H), 3.64 (s, 3H), 3.40 (bs, 2H), 3.04-2.90 (m, 5H), 1.89 (s, 3H), 1.73-1.53 (m, 2H), 1.37 (s, 9H), 1.26 (s, 6H); $^{13}$C NMR (101 MHz, DMSO, 24° C.) δ 170.2, 169.5, 164.1, 163.8, 155.6, 77.5, 58.2, 54.9, 47.9, 47.4, 37.4, 35.4, 34.8, 28.3, 27.2, 24.5, 23.6, 22.2; $^1$H NMR (400 MHz, DMSO, 80° C.) δ 8.00 (d, J=8.6 Hz, 1H), 6.46 (s, 1H), 4.54 (d, J=8.7 Hz, 1H), 3.66 (s, 3H), 3.41 (t, J=7.2 Hz, 2H), 3.01 (s, 3H), 2.96 (q, J=7.2 Hz, 2H), 1.92 (s, 3H), 1.70 (quintet, J=7.2 Hz, 2H), 1.40 (s, 9H), 1.31 (s, 3H), 1.30 (s, 3H); $^{13}$C NMR (101 MHz, DMSO, 80° C.) δ 169.6, 169.0, 164.0, 155.2, 77.2, 58.3, 51.6, 51.2, 47.5, 37.4, 34.7, 27.9, 27.4, 24.4, 23.8, 21.8; HRMS (ESI): m/z calcd. for $C_{18}H_{33}N_3O_6S_2Na^+$ [M+Na]$^+$ 474.1703, found 474.1714.

1.6.2 General Procedure for Synthesis of 7a-d

Scheme 7. Synthesis of alkylamine-substituted perthiocarbamates 7a-d

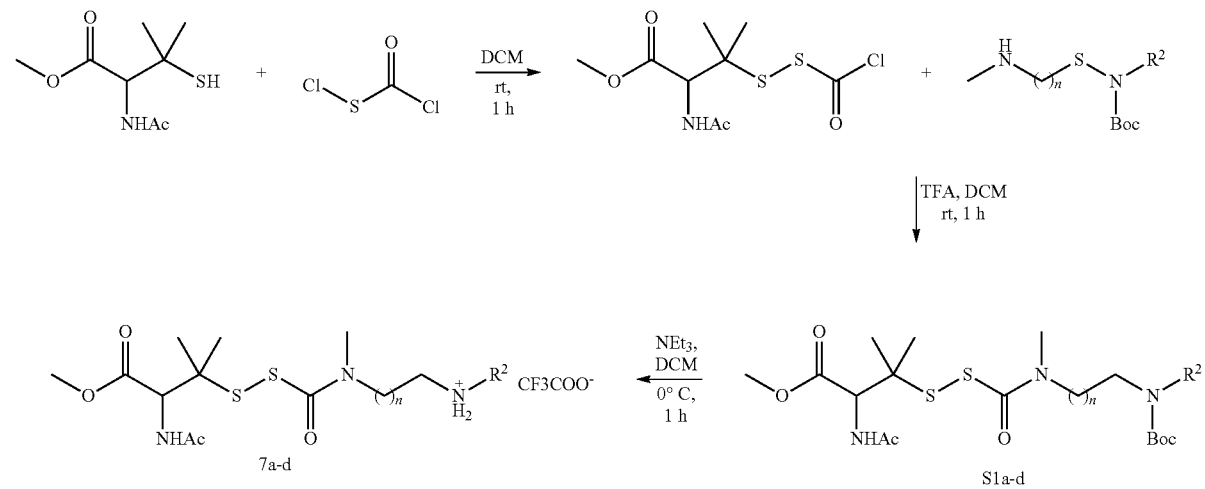

N-Boc protected compounds S1a-d (1 mmol) were dissolved in a 1:1 mixture of dichloromethane and trifluoroacetic acid (4 mL). The resulting solution was stirred at room temperature for 1 h, and volatiles were removed under reduced pressure. The dichloromethane was successively added and evaporated to remove the residual TFA and obtain the desired RSSH/COS precursor.

2-(((3-acetamido-4-methoxy-2-methyl-4-oxobutan-2-yl)disulfannecarbonyl)(methyl)amino)-N-methyl-ethan-1-aminium (7a)

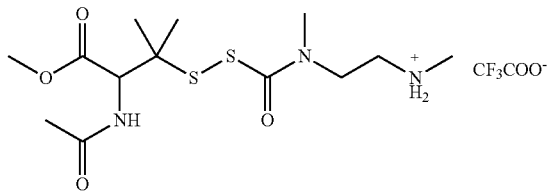

405 mg, 96% yield; semisolid; $^1$H NMR (400 MHz, CDCl$_3$) δ 9.02 (bs, 1H), 8.46 (bs, 1H), 7.85 (d, J=9.3 Hz, 1H), 4.63 (d, J=9.3 Hz, 1H), 4.13-4.10 (m, 1H), 3.74 (s, 3H), 3.55-3.51 (m, 1H), 3.36 (s, 2H), 3.13 (s, 3H), 2.79 (s, 3H), 2.14 (s, 3H), 1.50 (s, 3H), 1.35 (s, 3H); $^{13}$C NMR (101 MHz, CDCl$_3$) δ 171.7, 171.2, 169.4, 161.1 (q, J=37.5 Hz), 116.0 (q, J=289.9 Hz), 58.6, 53.1, 52.5, 47.4, 47.2, 35.8, 33.6, 27.1, 25.7, 22.7; HRMS (ESI): m/z calcd. for C$_{13}$H$_{26}$N$_3$O$_4$S$_2$$^+$ [M]$^+$ 352.1359, found 352.1367.

2-(((3-acetamido-4-methoxy-2-methyl-4-oxobutan-2-yl)disulfannecarbonyl)(methyl)amino)ethan-1-aminium (7b)

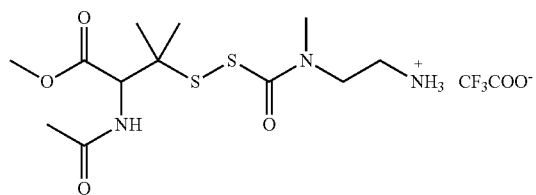

485 mg, 97% yield; semisolid; $^1$H NMR (400 MHz, CDCl$_3$) δ 8.40 (s, 3H), 8.19 (d, J=9.3 Hz, 1H), 4.61 (d, J=9.5 Hz, 2H), 3.75 (s, 3H), 3.38-3.16 (m, 6H), 1.97 (s, 3H), 1.42 (s, 3H), 1.29 (s, 3H); $^{13}$C NMR (101 MHz, CDCl$_3$) δ 172.2, 172.1, 170.9, 160.9 (q, J=37.3 Hz), 116.1 (q, J=289.9 Hz), 59.2, 52.7, 52.6, 48.3, 38.1, 35.3, 27.0, 26.8, 22.3; HRMS (ESI): m/z calcd. for C$_{12}$H$_{24}$N$_3$O$_4$S$_2$$^+$ [M]$^+$ 338.1203, found 338.1199.

3-(((3-acetamido-4-methoxy-2-methyl-4-oxobutan-2-yl)disulfannecarbonyl)(methyl)amino)-N-methyl-propan-1-aminium (7c)

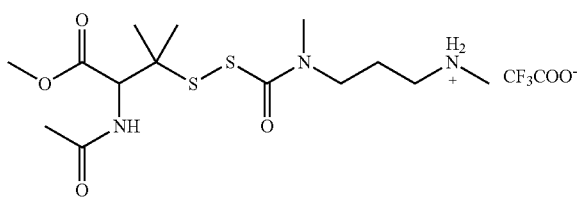

290 mg, 94% yield; semisolid; $^1$H NMR (400 MHz, DMSO) δ 8.47 (bs, 2H), 8.33 (d, J=8.7 Hz, 1H), 4.52 (d, J=8.7 Hz, 1H), 3.64 (s, 3H), 3.49-3.44 (m, 2H), 3.07-2.84 (m, 5H), 2.56 (s, 3H), 1.90 (s, 3H), 1.84-1.78 (m, 2H), 1.27 (s, 3H), 1.27 (s, 3H); $^{13}$C NMR (101 MHz, CDCl$_3$) δ 170.9, 170.4, 168.0, 161.9 (q, J=37.5 Hz), 116.6 (q, J=291.4 Hz), 59.0, 52.7, 52.2, 47.6, 46.8, 35.1, 33.2, 26.5, 25.7, 24.0, 22.8; HRMS (ESI): m/z calcd. for C$_{14}$H$_{28}$N$_3$O$_4$S$_2$$^+$ [M]$^+$ 366.1516, found 366.1515.

3-(((3-acetamido-4-methoxy-2-methyl-4-oxobutan-2-yl)disulfannecarbonyl)(methyl)amino)propan-1-aminium (7d)

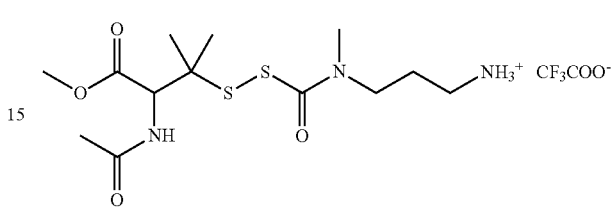

540 mg, 96% yield, semisolid; $^1$H NMR (400 MHz, CDCl$_3$) δ 7.91 (bs, 3H), 7.57 (d, J=8.4 Hz, 1H), 4.53 (d, J=8.4 Hz, 1H), 3.73 (s, 3H), 3.66-3.46 (m, 2H), 3.11 (s, 3H), 3.04 (s, 2H), 2.08 (s, 3H), 2.06-1.94 (m, 2H), 1.43 (s, 3H), 1.33 (s, 3H); $^{13}$C NMR (101 MHz, CDCl$_3$) δ 171.5, 170.5, 168.5, 161.5 (q, J=37.1 Hz), 116.4 (q, J=289.6 Hz), 59.2, 52.7, 52.3, 47.5, 37.2, 35.2, 26.3, 25.4, 25.1, 22.6; HRMS (ESI): m/z calcd. for C$_{13}$H$_{26}$N$_3$O$_4$S$_2$$^+$ [M]$^+$ 352.1359, found 352.1364.

Methyl 2-acetamido-3-methyl-3-((methyl(propyl)carbamoyl)disulfaneyl)butanoate (8)

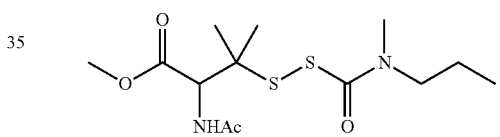

479 mg, 58% yield; mixture of rotamers; $^1$H NMR (400 MHz, DMSO, 24° C.) δ 8.31 (d, J=8.7 Hz, 1H), 4.51 (d, J=8.7 Hz, 1H), 3.64 (s, 3H), 3.40 (bs, 2H), 3.04 (s, 1.5H), 2.93 (s, 1.5H), 1.89 (s, 3H), 1.59-1.51 (m, 2H), 1.26 (s, 6H), 0.84 (3H); $^{13}$C NMR (101 MHz, DMSO, 24° C.) δ 170.2, 169.5, 163.9, 163.7, 58.1, 51.8, 51.7, 51.5, 51.0, 35.3, 34.6, 24.4, 23.6, 22.2, 20.8, 19.9, 10.8; $^1$H NMR (400 MHz, DMSO, 70° C.) δ 8.07 (d, J=8.7 Hz, 1H), 4.54 (d, J=8.7 Hz, 1H), 3.65 (s, 3H), 3.37 (t, J=7.2 Hz, 2H), 3.00 (s, 3H), 1.91 (s, 3H), 1.58 (sextet, J=7.2 Hz, 2H), 1.30 (s, 3H), 1.29 (s, 3H), 0.87 (t, J=7.2 Hz, 3H); $^{13}$C NMR (101 MHz, DMSO, 70° C.) δ 169.8, 169.1, 163.9, 58.2, 51.6, 51.3, 51.1, 34.7, 24.3, 23.7, 21.9, 20.1, 10.4; HRMS (ESI): m/z calcd. for C$_{13}$H$_{25}$N$_2$O$_2$S$_2$$^+$ [M+H]$^+$ 337.1250, found 337.1260.

2-Acetamido-3-(benzothiazol-2-yldisulfaneyl)-3-methylbutanoic Acid (S2)

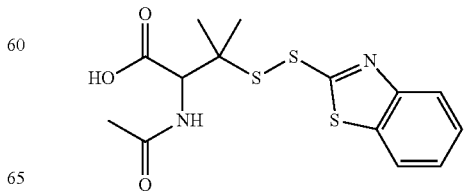

2, 2'-Dibenzothiazolyl disulfide (2.61 g, 7.84 mmol) was dissolved in CHCl₃ (100 mL). To this solution, N-acetyl-D-penicillamine (1 g, 5.23 mmol) was added. The reaction mixture was stirred at room temperature for 16 h. The solvent was removed under reduced pressure, and the residue was purified by flash column chromatography on silica gel (5% MeOH in DCM) to obtain S2 (1.49 g, 80% yield) as a white solid; $^1$H NMR (400 MHz, DMSO) δ 13.13 (s, 1H), 8.39 (d, J=9.3 Hz, 1H), 8.03 (d, J=8.0 Hz, 1H), 7.84 (d, J=8.0 Hz, 1H), 7.50-7.38 (m, 2H), 4.64 (d, J=9.2 Hz, 1H), 1.92 (s, 3H), 1.44 (s, 3H), 1.41 (s, 3H); 13C NMR (101 MHz, DMSO) δ 172.6, 170.8, 169.6, 154.3, 135.2, 126.6, 125.0, 121.9, 121.8, 58.0, 54.6, 25.0, 23.4, 22.3; HRMS (ESI): m/z calcd. for $C_{14}H_{17}N_2O_3S_3^+$ [M+H]⁺ 357.0396, found 357.0395.

Methyl 2-acetamido-3-(benzo[d]thiazol-2-yldisulfaneyl)-3-methylbutanoate (S3)

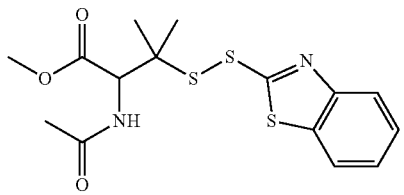 [SMILES: COC(=O)C(NC(C)=O)C(C)(C)SSc1nc2ccccc2s1]

To a solution of S2 (1.46 g, 4.1 mmol) in anhydrous methanol (30 mL) under a nitrogen atmosphere, chlorotrimethylsilane (1.33 g, 12.29 mmol) was added. The reaction mixture was stirred at room temperature for 16 h, and volatiles were removed under vacuum. The residue was purified by flash column chromatography (silica gel, hexane/ethyl acetate 50:50) to afford the product S3 (0.97 g, 64%) as a semisolid; $^1$H NMR (400 MHz, CDCl₃) δ 7.88 (d, J=7.8 Hz, 1H), 7.79 (dd, J=8.0, 0.6 Hz, 1H), 7.47-7.42 (m, 1H), 7.37-7.32 (m, 1H), 6.57 (d, J=9.0 Hz, 1H), 4.84 (d, J=9.3 Hz, 1H), 3.76 (s, 3H), 2.05 (s, 3H), 1.53 (s, 3H), 1.48 (s, 3H): $^{13}$C NMR (101 MHz, CDCl₃) δ 172.2, 170.4, 170.0, 154.5, 135.9, 126.5, 125.0, 122.3, 121.3, 59.0, 54.9, 52.6, 26.0, 24.9, 23.3; HRMS (ESI): m/z calcd. for $C_{15}H_{19}N_2O_3S_3^+$ [M+H]⁺ 371.0552, found 371.0560.

N-(4-Hydroxyphenethyl)-2-(tritylthio)acetamide (S4)

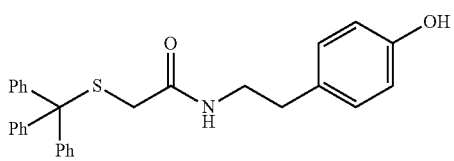 [SMILES: O=C(CSC(c1ccccc1)(c1ccccc1)c1ccccc1)NCCc1ccc(O)cc1]

To a solution of S-trityl 2-mercaptoacetic acid (1.80 g, 5.38 mmol) in anhydrous DMF (30 mL) at 0° C., EDC-HCl (1.24 g, 6.46 mmol) and DMAP (13 mg, 0.1 mmol) were added. The mixture was stirred at 0° C. for 1 h. Tyramine (812 mg, 5.92 mmol) was added to the reaction mixture and stirred at room temperature for overnight. The reaction mixture was quenched by the addition of 1 M HCl (50 mL) and extracted with ethyl acetate (3×30 mL). The combined organic layer was washed with brine, dried over Na₂SO₄, and the solvent was evaporated under vacuum. The residue was purified by flash column chromatography to afford the product S4 (1.45 g, 59% yield) as a white solid; $^1$H NMR (300 MHz, DMSO) δ 9.14 (s, 1H), 7.87 (t, J=5.2 Hz, 1H), 7.38-7.14 (m, 15H), 6.92 (d, J=8.2 Hz, 2H), 6.64 (d, J=8.2 Hz, 2H), 3.14-3.03 (m, 2H), 2.73 (s, 2H), 2.54 (2H), CH₂ protons merged with a DMSO-d₆ peak; $^{13}$C NMR (101 MHz, DMSO) δ 167.0, 155.6, 144.1, 129.4, 129.3, 129.1, 128.1, 126.8, 115.1, 65.9, 40.8, 36.0, 34.1; HRMS (ESI): m/z calcd. for $C_{29}H_{28}NO_2SNa^+$ [M+Na]⁺ 476.1655, found 476.1649.

N-(4-Hydroxyphenethyl)-2-mercaptoacetamide (S5)

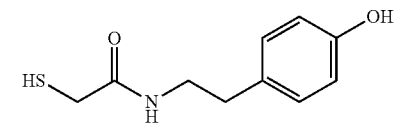 [SMILES: O=C(CS)NCCc1ccc(O)cc1]

To a stirred solution of S4 (200 mg, 0.4 mmol) in CH₂Cl₂ (10 ml) at 0° C., Et₃SiH (107 μL, 0.7 mmol), and CF₃COOH (1 mL) were added. The reaction mixture was warmed to room temperature, stirred for 1 h and volatiles were evaporated under vacuum. The residue was purified by flash chromatography (silica gel, eluent: 50% ethyl acetate in hexane) to afford the product S5 (64 mg, 69% yield) as a semisolid; $^1$H NMR (400 MHz, CDCl₃) δ 7.06 (d, J=8.4 Hz, 2H), 6.79 (d, J=8.4 Hz, 2H), 6.71 (s, 1H), 3.54-3.49 (m, 2H), 3.21 (d, J=9.1 Hz, 2H), 2.77 (t, J=7.0 Hz, 2H), 1.77 (t, J=9.1 Hz, 1H); $^{13}$C NMR (101 MHz, CDCl₃) δ 169.4, 154.7, 130.5, 130.0, 115.7, 41.3, 34.7, 28.5; HRMS (ESI): m/z calcd. for $C_{10}H_{14}NO_4S^+$ [M+H]⁺ 212.0740, found 212.0740

Ethyl 2-acetamido-3-((2-((4-hydroxyphenethyl)amino)-2-oxoethyl)disulfaneyl)-3-methylbutanoate (9)

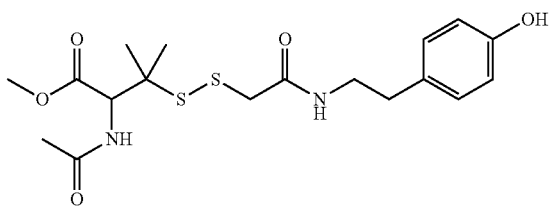 [SMILES: COC(=O)C(NC(C)=O)C(C)(C)SSCC(=O)NCCc1ccc(O)cc1]

To a nitrogen-flushed solution of S5 (107 mg, 0.5 mmol) and activated disulfide S3 (225 mg, 0.6 mmol) in dichloromethane (10 mL), triethylamine (0.14 mL, 1.1 mmol) was added. The reaction mixture was stirred at room temperature for 2 h. The mixture was quenched by the addition of 1M aqueous hydrochloric acid solution and extracted with dichloromethane. The organic layer was washed with brine, dried over Na₂SO₄, filtered, and the solvent was evaporated under vacuum. The crude product was purified by flash column chromatography to afford the product 9 (0.18 g, 86% yield) as a white solid; $^1$H NMR (400 MHz, CDCl₃) δ 7.04 (d, J=8.5 Hz, 2H), 6.79 (d, J=8.5 Hz, 2H), 6.59 (s, 1H), 6.54 (t, J=5.6 Hz, 1H), 6.43 (d, J=9.2 Hz, 1H), 4.73 (d, J=9.2 Hz, 1H), 3.74 (s, 3H), 3.50 (q, J=6.4 Hz, 2H), 3.46-3.32 (m, 2H), 2.76 (t, J=6.9 Hz, 2H), 2.05 (s, 3H), 1.38 (s, 3H), 1.37 (s, 3H); $^{13}$C NMR (101 MHz, CDCl₃) δ 170.9, 170.6, 168.7, 155.3, 129.9, 129.8, 115.8, 58.8, 52.6, 52.6, 43.6, 41.5, 34.7, 26.0, 24.2, 23.2; HRMS (ESI): m/z calcd. for $CH_{27}N_2O_5S_2^+$ [M+H]$^+$ 415.1356, found 415.1354.

1.6.3 RSSH Release from Precursor 1a Analyzed by UPLC-MS

Precursor 1a was dissolved in DMSO to afford a 1 mM stock solution. Similarly, HPE-IAM and N-ethyl maleimide (NEM) were independently dissolved in DMSO to obtain 50 mM stock solutions. To a 20 mL scintillation vial, HPE-IAM or NEM (30 μL, 50 mM) was added in pH 7.4 ammonium bicarbonate buffer (2.94 mL) containing the DTPA (100 μM). The resulting solution was pre-incubated at 37° C. for 10 min. Precursor 1a (30 μL, 1 mM) was then added into the mixture and incubated for 15 min at 37° C. An aliquot of the reaction mixture (500 μL) was withdrawn, 4-hydroxyphenylacetamide (10 μM) was added as internal standard, and analyzed using UPLC-MS as follows: Mobile phase: 0-1 min 90% water+0% ACN+10% formic acid (0.1%); 1-7.5 min gradient up to 10% water+80% ACN+10% formic acid (0.1%); 7.5-8.4 min 10% water+80% ACN+10% formic acid (0.1%); 8.4-8.5 min gradient up to 90% water+0% ACN+10% formic acid (0.1%), 8.5-10 min 90% water+0% ACN+10% formic acid (0.1%). Flow rate=0.3 mL/min. To quantify the byproduct 2a generated from 1a, a calibration curve with known concentrations of commercially available cyclic urea 2a was generated. These studies were conducted at least in triplicate and representative spectra are presented.

1.6.4 RSSH Generation and Quantification of Cyclic-Ureas 2a-d from 7a-d by UPLC-MS Precursors 7a-d (10 μM) were independently incubated with HPE-IAM (500 μM) in pH 7.4 ammonium bicarbonate buffer (50 mM) containing DTPA (100 μM) at 37° C. The reaction mixture (500 μL) was analyzed using UPLC-MS. To quantify 2a-d generated from these precursors, a calibration curve of each individual cyclic urea with known concentrations was independently generated.

1.6.5 Kinetics of RSSH Release from Precursors 7a-d Monitored by HPLC

Precursors 7a-d were dissolved in DMSO to afford 10 mM stock solutions. HPE-IAM was dissolved in DMSO to obtain a 100 mM stock solution. To a 20 mL scintillation vial, HPE-IAM (150 μL, 100 mM) was diluted in pH 7.4 phosphate buffer (2.82 mL) containing the DTPA (100 μM). This solution was pre-incubated for 10 min at 37° C. and then precursor 7a-d (30 μL, 10 mM) were independently added into the mixture. The resulting solution was incubated at 37° C. At different time points, an aliquot of 200 μL was taken and quenched with 200 μL % formic acid solution. These samples were stored at 0° C. until HPLC analysis was performed. The sample (20 μL) was injected into a high-performance liquid chromatography (HPLC) equipped with Phenomenex C-18 reverse phase column (250 mm×4.6 mm, 5 μm). HPLC Method: mobile phase A ($H_2O$) and mobile phase B (ACN), flow rate: 1 mL/min, run time: 20 min, the gradient elution method: 10% to 40% B from 0 to 12 min, 40% to 80% B from 12 to 20 min. The elution was monitored by a UV detector at 275 nm. A calibration curve was generated using RSS-HPE-AM 9 to quantify RSSH generation from 7a-d.

1.6.6 Analysis of RSSH Generation from 7a-d in the Presence of N-Acetyl Cysteine by UPLC-MS To a solution of N-acetyl cysteine (NAC, 500 μM) in pH 7.4 ammonium bicarbonate buffer (50 mM) containing DTPA (100 μM), precursors 7a-d (100 μM) were independently added. The resulting mixture was incubated at 37° C. An aliquot (200 μL) of reaction mixture was withdrawn at specified time points and quenched with 1% formic acid (200 μL). 3-Amino-benzoic acid (50 μM) was added to each sample as internal standard prior to UPLC-MS analysis. To quantify 2a-d generated from these precursors, a calibration curve for each individual cyclic urea with known concentrations was independently generated.

1.6.7 Analysis of COS Release from 7a-d in the Presence of N-Acetyl-Cysteine Using MIMS COS was analyzed using a Hiden HPR-40 MIMS system with a sample cell and membrane probe that have been optimized to detect gases dissolved in aqueous solution as described previously. Cline et al., 2011. A stock solution of N-acetyl-cysteine (25 mM) was prepared in DI water. RSSH precursor stock solutions (5 mM) were prepared in DMSO. These solutions were degassed by purging with nitrogen for 10 min before COS release analysis. Typically, 20 mL phosphate buffer solution (10 mM) was added to the sample cell, degassed and purged with a continuous flow of argon for 15 min. N-acetyl cysteine (200 μL, 25 mM) and RSSH precursor (200 μL, 5 mM) were then injected using a gas tight syringe and ion current at m/z 60 (COS$^+$) were collected for 2 h (source pressure was approximately $1\times10^{-7}$ to $5\times10^{-7}$ Torr).

1.6.8 Culture of Cells

H9c2(2-1) embryonic rat heart myoblasts were obtained from the American Type Culture Collection. Cells were grown in Dulbecco's minimal essential medium (DMEM), supplemented with fetal bovine serum (FBS) 10%, penicillin 100 U/mL and streptomycin 100 μg/mL. They were propagated in T75-flasks, split before reaching 70-80% confluence (usually every day or every second day), and used within 11 passages. Cells were passaged to tissue culture treated 96-well microtiter plates at the specified density in 180 μL volumes and incubated for 24 h.

1.6.9 Cytotoxicity Study of 7b

Cells were seeded at a density of $1\times10^4$ cells/well. After 24 h, the media was replaced and compound added in 20 μL volumes using DMSO:$H_2O$ (<0.01% DMSO) as the vehicle. Cells were incubated for an additional 24 h before media was removed. Then, 100 μL of media containing 3 μM SYTOX™ Green nucleic acid stain (Invitrogen) was added and the cells were incubated for 2 h before fluorescence readings were obtained at $485_{Ex}/538_{Em}$ (Step 1). Finally, an additional 100 μL of media containing 3 μM SYTOX™ and 0.2% Triton X-100 was added in order to permeabilize all cells and incubated for 1 h before fluorescence values measured (Step 2). The relative % cells surviving was calculated as a 100% minus the ratio of the fluorescence value of Step 1 over Step 2 (% cells surviving=100%–($FL_{538}$ (Step 1)/$FL_{538}$(Step 2)).

1.6.10 H9c2 Cell Protection by Precursor 7b from $H_2O_2$-Mediated Oxidative Stress

1.6.10.1 Cell Counting Kit-8 (CCK-8) (See Powell et al., 2018; Ishiyama et al., 1997; Tominaga et al., 1999)

Cells were seeded at a density of $5\times10^3$ cells/well. After 24 h, precursor 7b or byproduct 2b was added at 20 µL volumes using DMSO:$H_2O$ (<0.01% DMSO as the vehicle). Cells were incubated for 2 h before media was removed and the cells gently washed with PBS (pH 7.4). Then, 180 µL of fresh media and 20 µL $H_2O_2$ diluted into $H_2O$ were added and cells were incubated for an additional 2 h. At the completion of $H_2O_2$ exposure, each well is carefully washed 3 times with PBS (pH 7.4) before adding 100 µL of media, without-FBS, containing 10% v/v CCK-8 (Dojindo) and incubated for 3 h prior to obtaining absorbance values at 450 nm. The relative % viability was calculated as 100 times the ratio of the $Abs_{450}$ (pretreated, $H_2O_2$-exposed) over $Abs_{450}$ (vehicle-treated, non $H_2O_2$-exposed).

1.6.10.1 SYTOX™ Green Nucleic Acid Stain (See Hafgaard et al., 2006)

Cells were seeded at a density of $1\times10^4$ cells/well. After 24 h, precursor 7b or byproduct 2b is added in 20 µL volumes using DMSO: H2O (<0.01% DMSO). Cells were incubated for 2 h before media was removed and the cells gently washed with PBS (pH 7.4). Then, 180 µL of fresh media and 20 µL $H_2O_2$ diluted in $H_2O$ were added before cells were incubated for an additional 1 h. After removing this media, 100 µL of media containing 3 µM SYTOX™ Green nucleic acid stain was added, and the cells incubated for 2 h before fluorescence readings were obtained at $485_{Ex}$/$538_{Em}$ (Step 1). Finally, an additional 100 µL of media containing 3 µM SYTOX™ and 0.2% Triton X-100 was added in order to permeabilize all cells and incubated for 1 h before fluorescence values measured (Step 2). The relative % cells surviving was calculated as a 100% minus the ratio of the fluorescence value of Step 1 over Step 2 (% cells surviving=100%–($FL_{538}$ (Step 1)/$FL_{538}$ (Step 2)). Fluorescence values for vehicle-treated, non-$H_2O_2$-exposed wells were treated as background cell death and this value is added to the % cell survival for each subsequent group.

1.6.11 Isolated Perfused Heart Protocol and Infarct Size Determination (See Sun et al., 2016; Rossello et al., 2016; Bell et al., 2011)

Male C57BL/6J mice obtained from Jackson Laboratories (Bar Harbor, Me., USA) were used for all experiments. Mice were between 12 and 14 weeks of age at the time of experimentation. All animals received humane care in compliance with the "Principles of Laboratory Animal Care" formulated by the National Society for Medical Research and the "Guide for the Care and Use of Laboratory Animals" published by the US National Institutes of Health. The Animal Care and Use Committee from Johns Hopkins University approved of this study.

After anticoagulation with heparin and cervical dislocation, a thoracotomy was performed and the heart was quickly excised and placed in ice-cold Krebs-Henseleit buffer (in mmol/L: 11.1 D-glucose, 1.2 $MgSO_4$, 1.2 $KH_2PO_4$, 4.7 KCl, 118 NaCl, 2 $CaCl_2$), 25 $NaHCO_3$). The aorta was cannulated, and the heart was perfused with Krebs-Henseleit buffer (oxygenated with 95% $O_2$/5% $CO_2$ and maintained at pH 7.4) in retrograde fashion at a constant pressure of 80 mm/Hg at 37° C. After baseline equilibration for 20 min, mouse hearts were subjected to 20 min of no-flow global ischemia followed by 90 min of reperfusion. Pharmacological postconditioning with 7b (100 µM) was performed at the onset of reperfusion for 7 min. Hearts were then reperfused for a total of 90 min. Control hearts received no pharmacological postconditioning.

At the conclusion of reperfusion in either group, the heart was dismounted from the rig and the cannula was mounted on an infusion line connected to a syringe pump (Harvard Apparatus). The mouse hearts were perfused with 1% (w/v) of 2,3,5-triphenyltetrazolium chloride (TTC) while sitting in a bath of 1% TTC at 37° C. for 10 min (Flow rate=0.5 mL/min). Then, the pump is turned off and the heart remains in the TTC bath for an additional 5 min. Following incubation, the heart is de-cannulated, weighed and allowed to freeze to a semi-frozen state at −20° C. for 20-30 min before the heart is sliced transversely at 1 mm thick slices. The slices are then weighed and fixed overnight in 10% formalin, followed by imaging with a high-resolution camera. Planimetry of the images was conducted using ImageJ (NIH).

1.7 Representative Results

1.7.1 RSSH Release from the Precursor 1a Analyzed by UPLC-MS

Precursor 1a was dissolved in DMSO to afford a 1 mM stock solution. Similarly, HPE-IAM was dissolved in DMSO to obtain a 50 mM stock solution. To a 20 mL scintillation vial, HPE-IAM (30 µL, 50 mM) was added in pH 7.4 ammonium bicarbonate buffer (2.94 mL) containing the DTPA (100 µM). The resulting solution was pre-incubated at 37° C. for 10 min. Precursor 1a (30 µL, 1 mM) was then added into the mixture and incubated for 15 min at 37° C. An aliquot of the reaction mixture (500 µL) was withdrawn and analyzed using UPLC-MS as follows: Mobile phase: 0-1 min 90% water+0% ACN+10% formic acid (0.1%); 1-7.5 min gradient up to 10% water+80% ACN+10% formic acid (0.1%); 7.5-8.4 min 10% water+80% ACN+10% formic acid (0.1%); 8.4-8.5 min gradient up to 90% water+0% ACN+10% formic acid (0.1%), 8.5-10 min 90% water+0% ACN+10% formic acid (0.1%). Flow rate=0.3 mL/min. The mass signals for product of RSSH trapping with HPE-IAM were obtained via deconvolution using MassLynx 4.1 software. These studies were conducted at least in triplicate and representative spectra are presented.

1.7.2 Kinetics of RSSH Release from Precursors 7a-d Monitored by HPLC

Precursors 7a-d were dissolved in DMSO to afford 10 mM stock solutions. HPE-IAM was dissolved in DMSO to obtain a 100 mM stock solution. To a 20 mL scintillation vial, HPE-IAM (150 µL, 100 mM) was diluted in pH 7.4 phosphate buffer (2.82 mL) containing the DTPA (100 µM). This solution was pre-incubated for 10 min at 37° C. and then precursor 7a-d (30 µL, 10 mM) were independently added into the mixture. The resulting solution was incubated at 37° C. At different time points, an aliquot of 200 µL was taken and quenched with 200 µL % formic acid solution. These samples were stored at 0° C. until HPLC analysis was performed. The sample (20 µL) was injected into a high-performance liquid chromatography (HPLC) equipped with Phenomenex C-18 reverse phase column (250 mm×4.6 mm, 5 μm). HPLC Method: mobile phase A ($H_2O$) and mobile phase B (ACN), flow rate: 1 mL/min, run time: 20 min, the gradient elution method: 10% to 40% B from 0 to 12 min, 40% to 80% B from 12 to 20 min. The elution was monitored by a variable UV detector at 275 nm. A calibration curve was generated using RSS-HPE-AM 9 to quantify RSSH generation from 7a-d.

1.7.3 RSSH Generation and Quantification of Cyclic-Ureas 2a-d from 7a-d by UPLC-MS Precursors 7a-d (10 μM) were independently incubated with HPE-IAM (500 μM) in pH 7.4 ammonium bicarbonate buffer (50 mM) containing DTPA (100 μM) at 37° C. This reaction mixture was analyzed by UPLC-MS as follows: Mobile phase: 0-1 min 90% water+0% ACN+10% formic acid (0.1%); 1-7.5 min gradient up to 10% water+80% ACN+10% formic acid (0.1%); 7.5-8.4 min 10% water+ 80% ACN+10% formic acid (0.1%); 8.4-8.5 min gradient up to 90% water+0% ACN+10% formic acid (0.1%), 8.5-10 min 90% water+0% ACN+10% formic acid (0.1%). Flow rate=0.3 mL/min. To quantify 2a-d generated from these precursors, a calibration curve of each individual cyclic urea with known concentrations was independently generated.

1.7.4 Analysis of RSSH Generation from 7a-d in the Presence of N-Acetyl Cysteine by UPLC-MS To a solution of N-acetyl cysteine (NAC, 500 μM) in pH 7.4 ammonium bicarbonate buffer (50 mM) containing DTPA (100 μM), precursors 7a-d (100 μM) were independently added. The resulting mixture was incubated at 37° C. An aliquot (200 L) of reaction mixture was withdrawn at specified time points and quenched with 1% formic acid (200 μL). 3-amino-benzoic acid (50 μM) was added to each sample as internal standard prior to UPLC-MS analysis. To quantify 2a-d generated from these precursors, the calibration curve of each individual cyclic urea with known concentrations was independently generated.

1.7.5 Analysis of COS Release from 7a-d in the Presence of N-Acetyl-Cysteine Using MIMS COS was analyzed using a Hiden HPR-40 MIMS system with a sample cell and membrane probe that have been optimized to detect gases dissolved in aqueous solution as described previously. Cline et al., 2011. A stock solution of N-acetyl-cysteine (25 mM) was prepared in DI water. RSSH precursor stock solutions (5 mM) were prepared in DMSO. These solutions were degassed by purging with nitrogen for 10 min before COS release analysis. Typically, 20 mL phosphate buffer solution (10 mM) was added to the sample cell, degassed and purged with a continuous flow of argon for 15 min. N-acetyl cysteine (200 μL, 25 mM) and RSSH precursor (200 μL, 5 mM) were then injected using a gas tight syringe and ion current at m/z 60 (COS*) were collected for 2 h (source pressure was approximately $1\times10^{-7}$ to $5\times10^{-7}$ Torr).

1.7.6 Culture of Cells

H9c2(2-1) embryonic rat heart myoblasts were obtained from the American Type Culture Collection. Cells were grown in Dulbecco's minimal essential medium (DMEM), supplemented with fetal bovine serum (FBS) 10%, penicillin 100 U/mL and streptomycin 100 μg/mL. They were propagated in T75-flasks, split before reaching 70-80% confluence (usually every day or every second day), and used within 11 passages. Cells were passaged to tissue culture treated 96-well microtiter plates at the specified density in 180 μL volumes and incubated for 24 h.

1.7.7 Cytotoxicity Study of 7b

Cells were seeded at a density of $1\times10^4$ cells/well. After 24 h, the media was replaced and compound added in 20 μL volumes using DMSO:$H_2O$ (<0.01% DMSO) as the vehicle. Cells were incubated for an additional 24 h before media was removed. Then, 100 μL of media containing 3 μM SYTOX® Green nucleic acid stain (Invitrogen) was added and the cells were incubated for 2 h before fluorescence readings were obtained at $485_{Ex}/538_{Em}$ (Step 1). Finally, an additional 100 μL of media containing 3 μM SYTOX® and 0.2% Triton X-100 was added in order to permeabilize all cells and incubated for 1 h before fluorescence values measured (Step 2). The relative % cells surviving was calculated as a 100% minus the ratio of the fluorescence value of Step 1 over Step 2 (% cells surviving=100%– ($FL_{538}$ (Step 1)/$FL_{538}$(Step 2)).

1.7.8 H9c2 Cell Protection by Precursor 7b from $H_2O_2$-Mediated Oxidative Stress

1.7.8.1 Cell Counting Kit-8 (CCK-8)

See Powell et al., 2018; Ishiyama et al., 1997; and Tominaga et al., 1999, for general procedures. Cells were seeded at a density of $5\times10^3$ cells/well. After 24 h, precursor 7b or byproduct 2b was added at 20 μL volumes using DMSO:$H_2O$ (<0.01% DMSO as the vehicle). Cells were incubated for 2 h before media was removed and the cells gently washed with PBS (pH 7.4). Then, 180 μL of fresh media and 20 μL $H_2O_2$ diluted into $H_2O$ were added and cells were incubated for an additional 2 h. At the completion of $H_2O_2$ exposure, each well is carefully washed 3 times with PBS (pH 7.4) before adding 100 μL of media, without-FBS, containing 10% v/v CCK-8 (Dojindo) and incubated for 3 h prior to obtaining absorbance values at 450 nm. The relative % viability was calculated as 100 times the ratio of the $Abs_{450}$ (pretreated, $H_2O_2$-exposed) over $Abs_{450}$ (vehicle-treated, non $H_2O_2$-exposed).

1.7.8.2 SYTOX® Green Nucleic Acid Stain

See Hofgaard et al., 2006, for general procedures. Cells were seeded at a density of $1\times10^4$ cells/well. After 24 h, precursor 7b or byproduct 2b is added in 20 μL volumes using DMSO:$H_2O$ (<0.01% DMSO). Cells were incubated for 2 h before media was removed and the cells gently washed with PBS (pH 7.4). Then, 180 μL of fresh media and 20 μL $H_2O_2$ diluted in $H_2O$ were added before cells were incubated for an additional 1 h. After removing this media, 100 μL of media containing 3 μM SYTOX® Green nucleic acid stain was added, and the cells incubated for 2 h before fluorescence readings were obtained at $485_{Ex}/538_{Em}$ (Step 1). Finally, an additional 100 μL of media containing 3 μM SYTOX® and 0.2% Triton X-100 was added in order to permeabilize all cells and incubated for 1 h before fluorescence values measured (Step 2). The relative % cells surviving was calculated as a 100% minus the ratio of the fluorescence value of Step 1 over Step 2 (% cells surviving=100%–($FL_{538}$ (Step 1)/$FL_{538}$ (Step 2)). Fluorescence values for vehicle-treated, non-$H_2O_2$-exposed wells were treated as background cell death and this value is added to the % cell survival for each subsequent group.

1.7.9 Isolated Perfused Heart Protocol and Infarct Size Determination[9-11]

See Sun et al., 2016; Rossello et al., 2016; and Bell et al., 2011, for general procedures. Male C57BL/6J mice obtained from Jackson Laboratories (Bar Harbor, Me., USA) were used for all experiments. Mice were between 12 and 14 weeks of age at the time of experimentation. All animals received humane care in compliance with the "Principles of Laboratory Animal Care" formulated by the National Society for Medical Research and the "Guide for the Care and Use of Laboratory Animals" published by the US National Institutes of Health. The Animal Care and Use Committee from Johns Hopkins University approved of this study.

After anticoagulation with heparin and cervical dislocation, a thoracotomy was performed and the heart was quickly excised and placed in ice-cold Krebs-Henseleit buffer (in mmol/L: 11.1 D-glucose, 1.2 $MgSO_4$, 1.2 $KH_2PO_4$, 4.7 KCl, 118 NaCl, 2 $CaCl_2$), 25 $NaHCO_3$). The aorta was cannulated, and the heart was perfused with Krebs-Henseleit buffer (oxygenated with 95% $O_2$/5% $CO_2$ and maintained at pH 7.4) in retrograde fashion at a constant pressure of 80 mm/Hg at 37° C. After baseline equilibration for 20 min, mouse hearts were subjected to 20 min of no-flow global ischemia followed by 90 min of reperfusion. Pharmacological postconditioning with 7b (100 μM) was performed at the onset of reperfusion for 7 min. Hearts were then reperfused for a total of 90 min. Control hearts received no pharmacological postconditioning.

At the conclusion of reperfusion in either group, the heart was dismounted from the rig and the cannula was mounted on an infusion line connected to a syringe pump (Harvard Apparatus). The mouse hearts were perfused with 1% (w/v) of 2,3,5-triphenyltetrazolium chloride (TTC) while sitting in a bath of 1% TTC at 37° C. for 10 min (Flow rate=0.5 mL/min). Then, the pump is turned off and the heart remains in the TTC bath for an additional 5 min. Following incubation, the heart is de-cannulated, weighed and allowed to freeze to a semi-frozen state at −20° C. for 20-30 min before the heart is sliced transversely at 1 mm thick slices. The slices are then weighed and fixed overnight in 10% formalin, followed by imaging with a high-resolution camera. Planimetry of the images was conducted using ImageJ (NIH).

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Mustafa, A. K.; Gadalla, M. M.; Sen, N.; Kim, S.; Mu, W.; Gazi, S. K.; Barrow, R. K.; Yang, G.; Wang, R.; Snyder, S. H. $H_2S$ Signals Through Protein S-Sulfhydration. *Sci. Signal.* 2009, 2, ra72-ra72.

Gadalla, M. M.; Snyder, S. H. Hydrogen sulfide as a gasotransmitter. *J. Neurochem.* 2010, 113, 14-26.

Filipovic, M. R.; Zivanovic, J.; Alvarez, B.; Banerjee, R. Chemical Biology of H2S Signaling through Persulfidation. *Chem. Rev.* 2018, 118, 1253-1337.

Ju, Y.; Fu, M.; Stokes, E.; Wu, L.; Yang, G. H2S-Mediated Protein S-Sulfhydration: A Prediction for Its Formation and Regulation. *Molecules* 2017, 22, 1334.

Ida, T.; Sawa, T.; Ihara, H.; Tsuchiya, Y.; Watanabe, Y.; Kumagai, Y.; Suematsu, M.; Motohashi, H.; Fujii, S.; Matsunaga, T.; Yamamoto, M.; Ono, K.; Devarie-Baez, N. O.; Xian, M.; Fukuto, J. M.; Akaike, T. Reactive cysteine persulfides and S-polythiolation regulate oxidative stress and redox signaling. *Proc. Natl. Acad. Sci. U.S.A.* 2014, 111, 7606-7611.

Ono, K.; Akaike, T.; Sawa, T.; Kumagai, Y.; Wink, D. A.; Tantillo, D. J.; Hobbs, A. J.; Nagy, P.; Xian, M.; Lin, J.; Fukuto, J. M. Redox chemistry and chemical biology of H2S, hydropersulfides, and derived species: Implications of their possible biological activity and utility. *Free Radic. Biol. Med.* 2014, 77, 82-94.

Toohey, J. I. Persulfide sulfur is a growth factor for cells defective in sulfur metabolism. *Biochem. Cell Biol.* 1986, 64, 758-765.

Numakura, T.; Sugiura, H.; Akaike, T.; Ida, T.; Fujii, S.; Koarai, A.; Yamada, M.; Onodera, K.; Hashimoto, Y.; Tanaka, R.; Sato, K.; Shishikura, Y.; Hirano, T.; Yanagisawa, S.; Fujino, N.; Okazaki, T.; Tamada, T.; Hoshikawa, Y.; Okada, Y.; Ichinose, M. Production of reactive persulfide species in chronic obstructive pulmonary disease. *Thorax* 2017, 72, 1074-1083.

Kunikata, H.; Ida, T.; Sato, K.; Aizawa, N.; Sawa, T.; Tawarayama, H.; Murayama, N.; Fujii, S.; Akaike, T.; Nakazawa, T. Metabolomic profiling of reactive persulfides and polysulfides in the aqueous and vitreous humors. *Sci. Rep.* 2017, 7, 41984.

Massey, V.; Edmondson, D. On the Mechanism of Inactivation of Xanthine Oxidase by Cyanide. *J. Biol. Chem.* 1970, 245, 6595-6598.

Branzoli, U.; Massey, V. Evidence for an Active Site Persulfide Residue in Rabbit Liver Aldehyde Oxidase. *J. Biol. Chem.* 1974, 249, 4346-4349.

Dóka, É.; Pader, I.; Biró, A.; Johansson, K.; Cheng, Q.; Ballagó, K.; Prigge, J. R.; Pastor-Flores, D.; Dick, T. P.; Schmidt, E. E.; Arnér, E. S. J.; Nagy, P. A novel persulfide detection method reveals protein persulfide- and polysulfide-reducing functions of thioredoxin and glutathione systems. *Sci. Adv.* 2016, 2, e1500968.

Longen, S.; Richter, F.; Köhler, Y.; Wittig, I.; Beck, K.-F.; Pfeilschifter, J. Quantitative Persulfide Site Identification (qPerS-SID) Reveals Protein Targets of H2S Releasing Donors in Mammalian Cells. *Sci. Rep.* 2016, 6, 29808.

Wright, C. M.; Christman, G. D.; Snellinger, A. M.; Johnston, M. V.; Mueller, E. G. Direct evidence for enzyme persulfide and disulfide intermediates during 4-thiouridine biosynthesis. *Chem. Commun.* 2006, 3104-3106.

Akaike, T.; Ida, T.; Wei, F.-Y.; Nishida, M.; Kumagai, Y.; Alam, M. M.; Ihara, H.; Sawa, T.; Matsunaga, T.; Kasamatsu, S.; Nishimura, A.; Morita, M.; Tomizawa, K.; Nishimura, A.; Watanabe, S.; Inaba, K.; Shima, H.; Tanuma, N.; Jung, M.; Fujii, S.; Watanabe, Y.; Ohmuraya, M.; Nagy, P.; Feelisch, M.; Fukuto, J. M.; Motohashi, H. Cysteinyl-tRNA synthetase governs cysteine polysulfidation and mitochondrial bioenergetics. *Nat. Commun.* 2017, 8, 1177.

Cuevasanta, E.; Lange, M.; Bonanata, J.; Coitiño, E. L.; Ferrer-Sueta, G.; Filipovic, M. R.; Alvarez, B. Reaction of Hydrogen Sulfide with Disulfide and Sulfenic Acid to Form the Strongly Nucleophilic Persulfide. *J. Biol. Chem.* 2015, 290, 26866-26880.

Cuevasanta, E.; Reyes, A. M.; Zeida, A.; Mastrogiovanni, M.; De Armas, M. I.; Radi, R.; Alvarez, B.; Trujillo, M. Kinetics of formation and reactivity of the persulfide in the one-cysteine peroxiredoxin from *Mycobacterium tuberculosis*. *J. Biol. Chem.* 2019, 294, 13593-13605.

Saund, S. S.; Sosa, V.; Henriquez, S.; Nguyen, Q. N. N.; Bianco, C. L.; Soeda, S.; Millikin, R.; White, C.; Le, H.; Ono, K.; Tantillo, D. J.; Kumagai, Y.; Akaike, T.; Lin, J.; Fukuto, J. M. The chemical biology of hydropersulfides (RSSH): Chemical stability, reactivity and redox roles. *Arch. Biochem. Biophys.* 2015, 588, 15-24.

Millikin, R.; Bianco, C. L.; White, C.; Saund, S. S.; Henriquez, S.; Sosa, V.; Akaike, T.; Kumagai, Y.; Soeda, S.; Toscano, J. P.; Lin, J.; Fukuto, J. M. The chemical biology of protein hydropersulfides: Studies of a possible protective function of biological hydropersulfide generation. *Free Radic. Biol. Med.* 2016, 97, 136-147.

Shibata, A.; Ishima, Y.; Ikeda, M.; Sato, H.; Imafuku, T.; Chuang, V. T. G.; Ouchi, Y.; Abe, T.; Watanabe, H.; Ishida, T.; Otagiri, M.; Maruyama, T. Human serum albumin hydropersulfide is a potent reactive oxygen species scavenger in oxidative stress conditions such as chronic kidney disease. *Biochem. Biophys. Res. Commun.* 2016, 479, 578-583.

Álvarez, L.; Bianco, C. L.; Toscano, J. P.; Lin, J.; Akaike, T.; Fukuto, J. M. Chemical Biology of Hydropersulfides and Related Species: Possible Roles in Cellular Protection and Redox Signaling. *Antioxid. Redox Signal.* 2017, 27, 622-633.

Yang, C.-t.; Devarie-Baez, N. O.; Hamsath, A.; Fu, X.-d.; Xian, M. S-Persulfidation: Chemistry, Chemical Biology, and Significance in Health and Disease. *Antioxid. Redox Signal.* 2019, DOI.org/10.1089/ars.2019.7889.

Bianco, C. L.; Chavez, T. A.; Sosa, V.; Saund, S. S.; Nguyen, Q. N. N.; Tantillo, D. J.; Ichimura, A. S.; Toscano, J. P.; Fukuto, J. M. The chemical biology of the persulfide (RSSH)/perthiyl (RSS) redox couple and possible role in biological redox signaling. *Free Radic. Biol. Med.* 2016, 101, 20-31.

Chauvin, J.-P. R.; Griesser, M.; Pratt, D. A. Hydropersulfides: H-Atom Transfer Agents Par Excellence. *J. Am. Chem. Soc.* 2017, 139, 6484-6493.

Fukuto, J. M.; Ignarro, L. J.; Nagy, P.; Wink, D. A.; Kevil, C. G.; Feelisch, M.; Cortese-Krott, M. M.; Bianco, C. L.; Kumagai, Y.; Hobbs, A. J.; Lin, J.; Ida, T.; Akaike, T. Biological hydropersulfides and related polysulfides—a new concept and perspective in redox biology. *FEBS Lett.* 2018, 592, 2140-2152.

Bianco, C. L.; Akaike, T.; Ida, T.; Nagy, P.; Bogdandi, V.; Toscano, J. P.; Kumagai, Y.; Henderson, C. F.; Goddu, R. N.; Lin, J.; Fukuto, J. M. The reaction of hydrogen sulfide with disulfides: formation of a stable trisulfide and implications for biological systems. *Br. J. Pharmacol.* 2019, 176, 671-683.

Lin, J.; Akiyama, M.; Bica, I.; Long, F. T.; Henderson, C. F.; Goddu, R. N.; Suarez, V.; Baker, B.; Ida, T.; Shinkai, Y.; Nagy, P.; Akaike, T.; Fukuto, J. M.; Kumagai, Y. The Uptake and Release of Polysulfur Cysteine Species by Cells: Physiological and Toxicological Implications. *Chem. Res. Toxicol.* 2019, 32, 447-455.

Shinkai, Y.; Kumagai, Y. Sulfane Sulfur in Toxicology: A Novel Defense System Against Electrophilic Stress. *Toxicol. Sci.* 2019, 170, 3-9.

Artaud, I; Galardon, E., A Persulfide Analogue of the Nitrosothiol SNAP: Formation, Characterization and Reactivity. *Chem Bio Chem* 2014, 15, 2361-2364.

Khodade, V. S.; Toscano, J. P. Development of S-Substituted Thioisothioureas as Efficient Hydropersulfide Precursors. *J. Am. Chem. Soc.* 2018, 140, 17333-17337.

Zheng, Y.; Yu, B.; Li, Z.; Yuan, Z.; Organ, C. L.; Trivedi, R. K.; Wang, S.; Lefer, D. J.; Wang, B. An Esterase-Sensitive Prodrug Approach for Controllable Delivery of Persulfide Species. *Angew. Chem., Int. Ed.* 2017, 56, 11749-11753.

Kang, J.; Xu, S.; Radford, M. N.; Zhang, W.; Kelly, S. S.; Day, J. J.; Xian, M. O→S Relay Deprotection: A General Approach to Controllable Donors of Reactive Sulfur Species. *Angew. Chem., Int. Ed.* 2018, 130, 5995-5999.

Powell, C. R.; Dillon, K. M.; Wang, Y.; Carrazzone, R. J.; Matson, J. B. A Persulfide Donor Responsive to Reactive Oxygen Species: Insights into Reactivity and Therapeutic Potential. *Angew. Chem., Int. Ed.* 2018, 57, 6324-6328.

Bora, P.; Chauhan, P.; Manna, S.; Chakrapani, H. A Vinyl-Boronate Ester-Based Persulfide Donor Controllable by Hydrogen Peroxide, a Reactive Oxygen Species (ROS). *Org. Lett.* 2018, 20, 7916-7920.

Saari, W. S.; Schwering, J. E.; Lyle, P. A.; Smith, S. J.; Engelhardt, E. L. Cyclization-activated prodrugs. Basic carbamates of 4-hydroxyanisole. *J. Med. Chem.* 1990, 33, 97-101.

Gomes, P.; Vale, N.; Moreira, R. Cyclization-activated Prodrugs. *Molecules* 2007, 12, 2484-2506.

Blencowe, C. A.; Russell, A. T.; Greco, F.; Hayes, W.; Thornthwaite, D. W. Self-immolative linkers in polymeric delivery systems. *Polym. Chem.* 2011, 2, 773-790.

Zhao, Y.; Cerda, Matthew M.; Pluth, M. D. Fluorogenic hydrogen sulfide (H2S) donors based on sulfenyl thiocarbonates enable H2S tracking and quantification. *Chem. Sci.* 2019, 10, 1873-1878.

Chengelis, C. P.; Neal, R. A. Studies of carbonyl sulfide toxicity: Metabolism by carbonic anhydrase. *Toxicol. Appl. Pharmacol.* 1980, 55, 198-202.

Steiger, A. K.; Zhao, Y.; Pluth, M. D. Emerging Roles of Carbonyl Sulfide in Chemical Biology: Sulfide Transporter or Gasotransmitter? *Antioxid. Redox Signal.* 2017, 28, 1516-1532.

Steiger, A. K.; Pardue, S.; Kevil, C. G.; Pluth, M. D. Self-Immolative Thiocarbamates Provide Access to Triggered H2S Donors and Analyte Replacement Fluorescent Probes. *J. Am. Chem. Soc.* 2016, 138, 7256-7259.

Zhao, Y.; Pluth, M. D. Hydrogen Sulfide Donors Activated by Reactive Oxygen Species. *Angew. Chem. Int. Ed.* 2016, 55, 14638-14642.

Powell, C. R.; Foster, J. C.; Okyere, B.; Theus, M. H.; Matson, J. B. Therapeutic Delivery of H2S via COS: Small Molecule and Polymeric Donors with Benign Byproducts. *J. Am. Chem. Soc.* 2016, 138, 13477-13480.

Sharma, A. K.; Nair, M.; Chauhan, P.; Gupta, K.; Saini, D. K.; Chakrapani, H. Visible-Light-Triggered Uncaging of Carbonyl Sulfide for Hydrogen Sulfide (H2S) Release. *Org. Lett.* 2017, 19, 4822-4825.

Powell, C. R.; Foster, J. C.; Swilley, S. N.; Kaur, K.; Scannelli, S. J.; Troya, D.; Matson, J. B. Self-amplified depolymerization of oligo(thiourethanes) for the release of COS/H2S. *Polym. Chem.* 2019, 10, 2991-2995.

Zhao, Y.; Steiger, A. K.; Pluth, M. D. Cyclic Sulfenyl Thiocarbamates Release Carbonyl Sulfide and Hydrogen Sulfide Independently in Thiol-Promoted Pathways. *J. Am. Chem. Soc.* 2019, 141, 13610-13618.

Chauhan, P.; Gupta, K.; Ravikumar, G.; Saini, D. K.; Chakrapani, H. Carbonyl Sulfide (COS) Donor Induced Protein Persulfidation Protects against Oxidative Stress. *Chem.: Asian J.* 2019, 14, 4717-4724.

Hamid, H. A.; Tanaka, A.; Ida, T.; Nishimura, A.; Matsunaga, T.; Fujii, S.; Morita, M.; Sawa, T.; Fukuto, J. M.; Nagy, P.; Tsutsumi, R.; Motohashi, H.; Ihara, H.; Akaike, T. Polysulfide stabilization by tyrosine and hydroxyphenyl-containing derivatives that is important for a reactive sulfur metabolomics analysis. *Redox Biol.* 2019, 21, 101096.

Cline, M. R.; Tu, C.; Silverman, D. N.; Toscano, J. P. Detection of nitroxyl (HNO) by membrane inlet mass spectrometry. *Free Radic. Biol. Med.* 2011, 50, 1274-1279.

Wang, Y.; Chun, O. K.; Song, W. O. Plasma and Dietary Antioxidant Status as Cardiovascular Disease Risk Factors: A Review of Human Studies. *Nutrients* 2013, 5, 2969-3004.

Bajic, V. P.; Van Neste, C.; Obradovic, M.; Zafirovic, S.; Radak, D.; Bajic, V. B.; Essack, M.; Isenovic, E. R. Glutathione "Redox Homeostasis" and Its Relation to Cardiovascular Disease. *Oxid. Med. Cell. Longev.* 2019, 2019, 14.

Effros, R. M.; Haider, B.; Ettinger, P. O.; Ahmed Sultan, S.; Oldewurtel, H. A.; Marold, K.; Regan, T. J. In vivo myocardial cell pH in the dog. Response to ischemia and infusion of alkali. *J. Clin. Invest.* 1975, 55, 1100-1110.

Yan, G. X.; Klêber, A. G. Changes in extracellular and intracellular pH in ischemic rabbit papillary muscle. *Circ. Res.* 1992, 71, 460-470.

Aldini, G.; Altomare, A.; Baron, G.; Vistoli, G.; Carini, M.; Borsani, L.; Sergio, F. N-Acetylcysteine as an antioxidant and disulphide breaking agent: the reasons why. *Free Radic. Res.* 2018, 52, 751-762.

Jones, L. J.; Singer, V. L. Fluorescence Microplate-Based Assay for Tumor Necrosis Factor Activity Using SYTOX Green Stain. *Anal. Biochem.* 2001, 293, 8-15.

Ishiyama, M.; Miyazono, Y.; Sasamoto, K.; Ohkura, Y.; Ueno, K. A highly water-soluble disulfonated tetrazolium salt as a chromogenic indicator for NADH as well as cell viability. *Talanta* 1997, 44, 1299-1305.

Tominaga, H.; Ishiyama, M.; Ohseto, F.; Sasamoto, K.; Hamamoto, T.; Suzuki, K.; Watanabe, M. A water-soluble tetrazolium salt useful for colorimetric cell viability assay. *Anal. Commun.* 1999, 36, 47-50.

Pagliaro, P.; Mancardi, D.; Rastaldo, R.; Penna, C.; Gattullo, D.; Miranda, K. M.; Feelisch, M.; Wink, D. A.; Kass, D. A.; Paolocci, N. Nitroxyl affords thiol-sensitive myocardial protective effects akin to early preconditioning. *Free Radic. Biol. Med.* 2003, 34, 33-43.

Bell, R. M.; Mocanu, M. M.; Yellon, D. M. Retrograde heart perfusion: The Langendorff technique of isolated heart perfusion. *J. Mol. Cell. Cardiol.* 2011, 50, 940-950.

Rossello, X.; Hall, A. R.; Bell, R. M.; Yellon, D. M. Characterization of the Langendorff Perfused Isolated Mouse Heart Model of Global Ischemia-Reperfusion Injury:Impact of Ischemia and Reperfusion Length on Infarct Size and LDH Release. *J. Cardiovasc. Pharmacol. Ther.* 2016, 21, 286-295.

Meyer, Y.; Richard, J.-A.; Delest, B.; Noack, P.; Renard, P.-Y.; Romieu, A. A comparative study of the self-immolation of para-aminobenzylalcohol and hemithioaminal-based linkers in the context of protease-sensitive fluorogenic probes. *Org. Biomol. Chem.* 2010, 8, 1777-1780.

Devine, W. G.; Diaz-Gonzalez, R.; Ceballos-Perez, G.; Rojas, D.; Satoh, T.; Tear, W.; Ranade, R. M.; Barros-Álvarez, X.; Hol, W. G. J.; Buckner, F. S.; Navarro, M.; Pollastri, M. P. From Cells to Mice to Target: Characterization of NEU-1053 (SB-443342) and Its Analogues for Treatment of Human African Trypanosomiasis. *ACS Infect. Dis.* 2017, 3, 225-236.

Bogdândi, V.; Ida, T.; Sutton, T. R.; Bianco, C.; Ditrôi, T.; Koster, G.; Henthorn, H. A.; Minnion, M.; Toscano, J. P.; van der Vliet, A.; Pluth, M. D.; Feelisch, M.; Fukuto, J. M.; Akaike, T.; Nagy, P. Speciation of reactive sulfur species and their reactions with alkylating agents: do we have any clue about what is present inside the cell? *Br. J. Pharmacol.* 2019, 176, 646-670.

Li, J.; Sha, Y. A Convenient Synthesis of Amino Acid Methyl Esters. *Molecules* 2008, 13, 1111-1119.

Hofgaard, J. P.; Sigurdardottir, K. S.; Treiman, M. Protection by 6-aminonicotinamide against oxidative stress in cardiac cells. *Pharmacol. Res.* 2006, 54, 303-310.

Sun, J.; Aponte, A. M.; Menazza, S.; Gucek, M.; Steenbergen, C.; Murphy, E. Additive cardioprotection by pharmacological postconditioning with hydrogen sulfide and nitric oxide donors in mouse heart: S-sulfhydration vs. S-nitrosylation. *Cardiovasc. Res.* 2016, 110, 96-106.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A compound of formula (I):

$$R_1\text{-S-S-C(=O)-N(R_3)-(CH_2)_n-N^+H_2-R_2 \ X^-} \quad (I)$$

wherein:
  n is an integer selected from the group consisting of 0, 1, 2, 3, 4, 5, 6, 7, and 8;
  $R_1$ is selected from the group consisting of branched or unbranched alkyl, heterocycloalkyl, aryl, heteroaryl, a cysteine residue, a N-acetylcysteine residue, a homocysteine residue, a glutathione residue, and:

$$\text{structure with } R_4, R_5, R_6, R_7 \text{ substituents and NH}$$

wherein:
  $R_4$ and $R_5$ are each independently selected from the group consisting of H, $C_1$-$C_4$ alkyl, and aryl;
  $R_6$ is $C_1$-$C_4$ alkyl or aryl;
  $R_7$ is —$OR_8$ or —$NR_9R_{10}$, wherein $R_8$, $R_9$, and $R_{10}$ are each independently selected from the group consisting of H, $C_1$-$C_4$ alkyl, and aryl;
  $R_2$ is selected from the group consisting of H, alkyl, aryl, and a functional group that responds to a stimulus selected from the group consisting of light, a redox reaction, and an enzymatic reaction;
  $R_3$ is selected from the group consisting of H, alkyl, and aryl; and
  $X^-$ is an anion.

2. The compound of claim 1, wherein n is an integer selected from the group consisting of 1, 2, and 3.

3. The compound of claim 1, wherein the compound of formula (I) is:

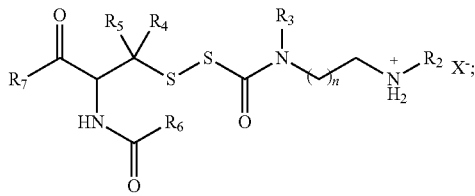

n is an integer selected from the group consisting of 1, 2, and 3;

$R_4$ and $R_5$ are each independently H or $C_1$-$C_4$ alkyl;

$R_6$ is $C_1$-$C_4$ alkyl or aryl;

$R_7$ is —$OR_8$ or —$NR_9R_{10}$, wherein $R_8$, $R_9$, and $R_{10}$ are each independently selected from the group consisting of H, $C_1$-$C_4$ alkyl, and aryl;

$R_2$ is selected from the group consisting of H, $C_1$-$C_4$ alkyl, and a functional group that responds to a stimulus selected from the group consisting of light, a redox reaction, and an enzymatic reaction;

$R_3$ is selected from the group consisting of H, alkyl, and aryl; and $X^-$ is an anion.

4. The compound of claim 3, wherein the compound of formula (I) is:

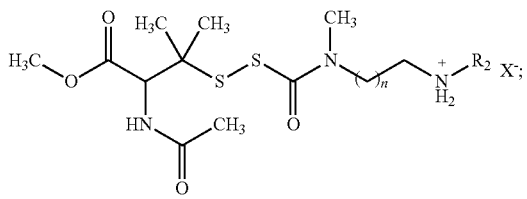

wherein:

n is 1 or 2; and $R_2$ is H or $CH_3$.

5. The compound of claim 4, wherein the compound is selected from the group consisting of:

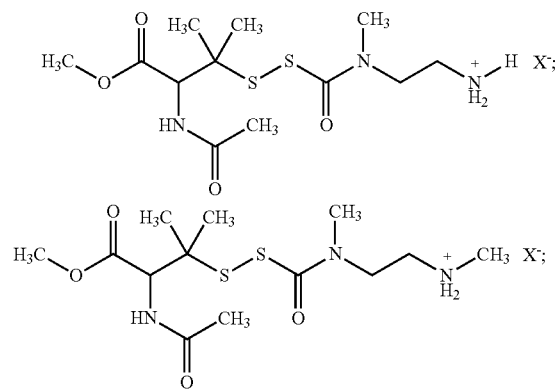

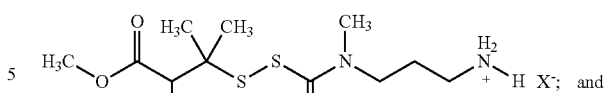

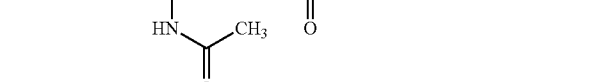

6. The compound of claim 1, wherein $X^-$ is selected from the group consisting of $Cl^-$, $Br^-$, $(PO_4)^{3-}$, $CF_3COO^-$, $CH_3COO^-$, and $C_6H_5COO^-$.

7. The compound of claim 1, wherein the functional group that responds to a stimulus selected from the group consisting of light, a redox reaction, and an enzymatic reaction is selected from the group consisting of:

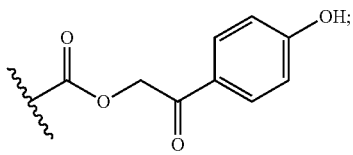

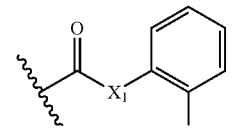

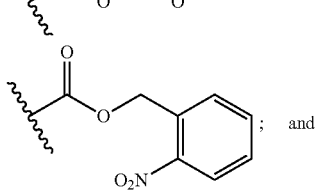

; and

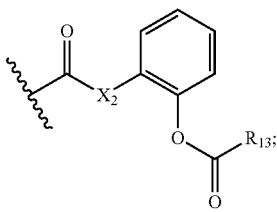

wherein:

$X_1$ and $X_2$ are each independently selected from the group consisting of O, $NR_{14}$, and $CR_{15}R_{16}$; wherein $R_{14}$, $R_{15}$, and $R_{16}$ are each independently H or branched or unbranched $C_1$-$C_4$ alkyl;

$R_{11}$ and $R_{12}$ are each independently selected from the group consisting of H, and branched or unbranched alkyl, or $R_{11}$ and $R_{12}$ together can form a cyclic alkyl or substituted cyclic alkyl; and $R_{13}$ is selected from the group consisting of branched or unbranched alkyl and aryl.

8. The compound of claim 6, wherein X⁻ is CF₃COO⁻ and the compound of formula (I) is selected from the group consisting of:
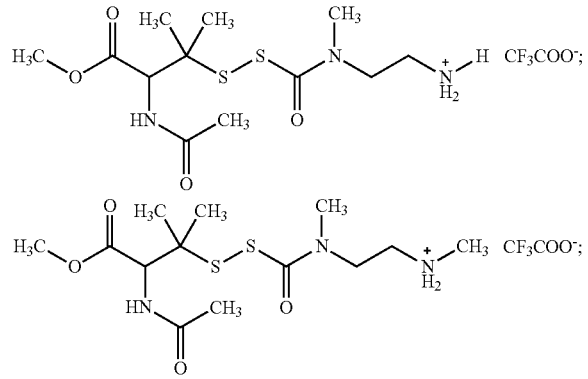
-continued
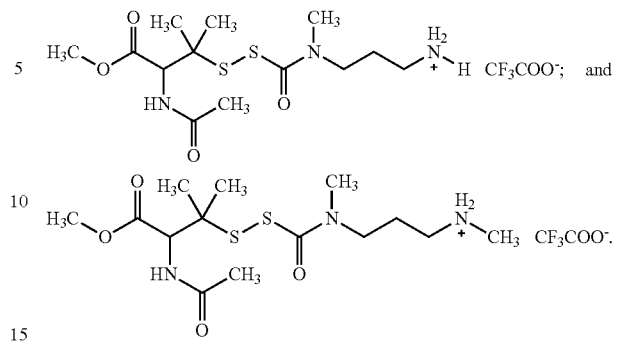
9. A pharmaceutical composition comprising a compound of claim 1 and a pharmaceutically acceptable carrier.
* * * * *